(12) United States Patent
Sampathkumar et al.

(10) Patent No.: US 12,364,756 B2
(45) Date of Patent: Jul. 22, 2025

(54) PHARMACEUTICAL COMPOSITIONS OF A PD-1 ANTIBODY AND USE OF THE SAME

(71) Applicant: MACROGENICS, INC., Rockville, MD (US)

(72) Inventors: Krishnan Sampathkumar, Rockville, MD (US); Yan Zhou, Rockville, MD (US); Stephen James Burke, Rockville, MD (US)

(73) Assignee: Macrogenics, Inc., Rockville, MD (US)

( * ) Notice: Subject to any disclaimer, the term of this patent is extended or adjusted under 35 U.S.C. 154(b) by 338 days.

(21) Appl. No.: 17/847,094

(22) Filed: Jun. 22, 2022

(65) Prior Publication Data

US 2023/0025464 A1 Jan. 26, 2023

Related U.S. Application Data

(60) Provisional application No. 63/220,006, filed on Jul. 9, 2021.

(51) Int. Cl.

| *A61K 39/395* | (2006.01) |
|---|---|
| *A61K 47/12* | (2006.01) |
| *A61K 47/26* | (2006.01) |
| *C07K 16/28* | (2006.01) |

(52) U.S. Cl.
CPC ........ *A61K 39/39591* (2013.01); *A61K 47/12* (2013.01); *A61K 47/26* (2013.01); *C07K 16/2818* (2013.01); *C07K 2317/24* (2013.01); *C07K 2317/76* (2013.01)

(58) Field of Classification Search
CPC ........... C07K 2317/94; A61P 35/00; A61K 2039/505
See application file for complete search history.

(56) References Cited

U.S. PATENT DOCUMENTS

| 7,648,702 B2 * | 1/2010 | Gombotz | A61P 19/02 424/134.1 |
|---|---|---|---|
| 2020/0147213 A1 * | 5/2020 | Sharma | C07K 16/2818 |
| 2020/0237906 A1 * | 7/2020 | Li | A61K 9/08 |
| 2022/0283167 A1 | 9/2022 | Nishikawa et al. | |

FOREIGN PATENT DOCUMENTS

| WO | WO-2017019846 A1 * | 2/2017 | ................ A61P 1/04 |
|---|---|---|---|
| WO | WO-2019171253 A1 * | 9/2019 | ....... A61K 39/39591 |
| WO | WO-2019206281 A1 * | 10/2019 | ............. A61K 47/26 |
| WO | WO-2021/022172 A1 | 2/2021 | |
| WO | WO-2021/025031 A1 | 2/2021 | |

OTHER PUBLICATIONS

Translation of WO 2019/206281, translated on Aug. 12, 2024. (Year: 2019).*
Strome et al., The Oncologist, 2007; 12:1084-95 (Year: 2007).*
Brand et al., Anticancer Res. 2006; 26:463-70 (Year: 2006).*
Maio et al, Journal of Clinical Oncology, vol. 39. No. 15 suppl Abstract 2571 3 pages, May 28, 2021 (Year: 2021).*
Emea et al., "Withdrawal Assessment Report Zynyz," 116 pages (Jun. 2021).
International Search Report and Written Opinion issued in International Patent Application No. PCT/US2022/034493, dated Oct. 17, 2022.
Cheung et al., "Fit-For-Purpose PD-L1 Biomarker Testing For Patient Selection in Immuno-Oncology: Guidelines for Clinical Laboratories From the Canadian Association of Pathologists—Association Canadienne Des Pathologistes (CAP-ACP)." Appl Immunohistochem Mol Morphol 27 (10), pp. 699-714 (2019).
WHO Drug Information, Proposed INN: List 121, 33(2)), pp. 326-327 (2019).

* cited by examiner

*Primary Examiner* — Sheela J. Huff

(74) *Attorney, Agent, or Firm* — Foley & Lardner LLP

(57) ABSTRACT

The present disclosure is provides pharmaceutical compositions, for storage and administration, comprising a human PD-1 ("hPD-1") antibody ("retifanlimab") and buffering agents. The disclosure further provides containers and kits comprising such pharmaceutical compositions. The disclosure further provides the use of such pharmaceutical compositions, containers, and kits containing retifanlimab in the treatment of a cancer, and in certain aspects treatment of a cancer expressing PD-L1.

66 Claims, 1 Drawing Sheet

Specification includes a Sequence Listing.

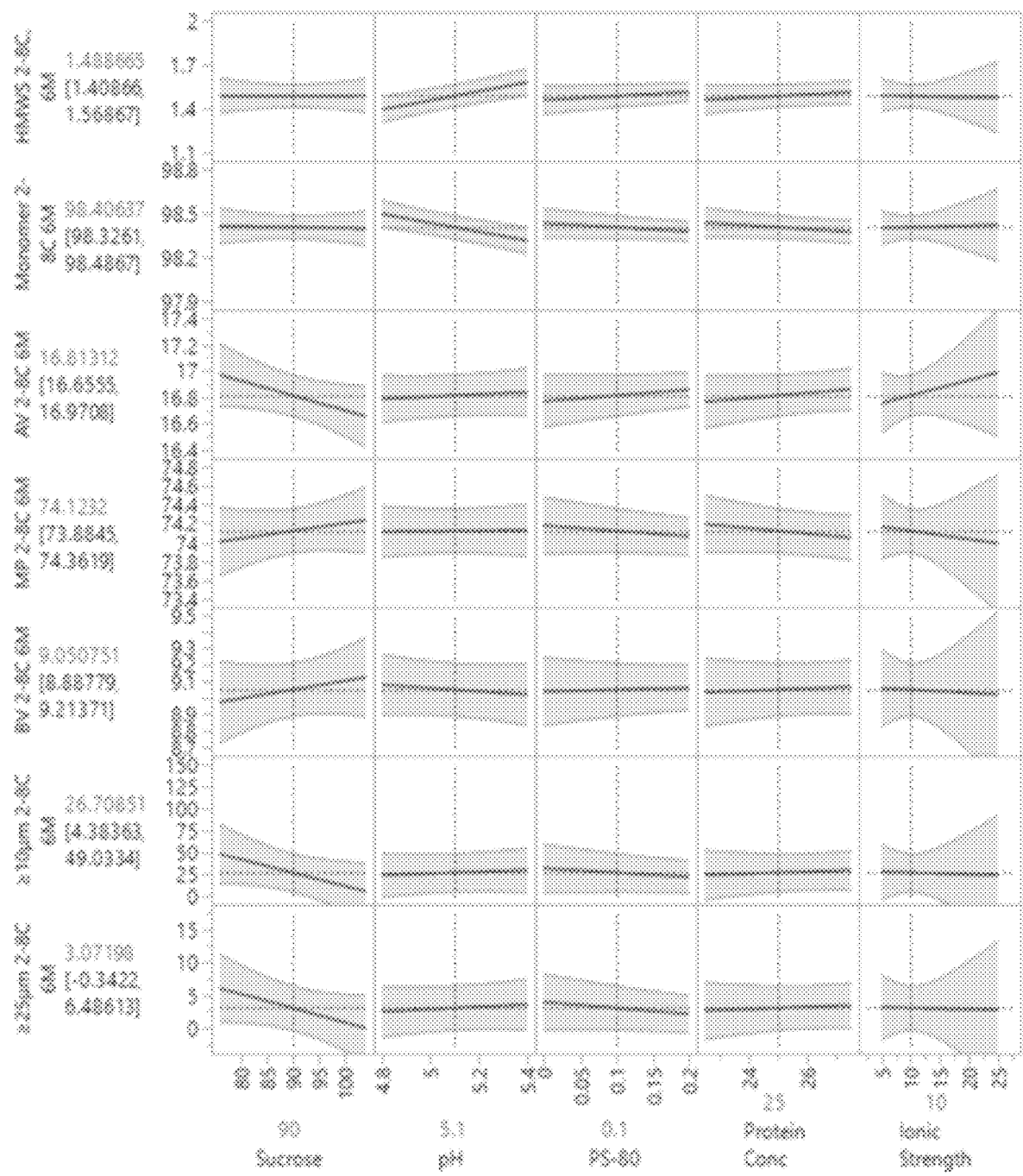

SEQUENCE LISTING

```
<160> NUMBER OF SEQ ID NOS: 10

<210> SEQ ID NO 1
<211> LENGTH: 445
<212> TYPE: PRT
<213> ORGANISM: Artificial Sequence
<220> FEATURE:
<223> OTHER INFORMATION: Heavy chain of retifanlimab

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met Asn Trp Val Arg Gln Ala Pro Gly Gln Gly Leu Glu Trp Ile
            35                  40                  45

Gly Val Ile His Pro Ser Asp Ser Glu Thr Trp Leu Asp Gln Lys Phe
        50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu His Tyr Gly Thr Ser Pro Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
            435                 440                 445

<210> SEQ ID NO 2
<211> LENGTH: 218
<212> TYPE: PRT
<213> ORGANISM: Artificial Sequence
<220> FEATURE:
<223> OTHER INFORMATION: Light chain of retifanlimab

<400> SEQUENCE: 2

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Glu Ser Val Asp Asn Tyr
             20                  25                  30

Gly Met Ser Phe Met Asn Trp Phe Gln Gln Lys Pro Gly Gln Pro Pro
         35                  40                  45

Lys Leu Leu Ile His Ala Ala Ser Asn Gln Gly Ser Gly Val Pro Ser
 50                      55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Lys
                 85                  90                  95

Glu Val Pro Tyr Thr Phe Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 5
<212> TYPE: PRT
<213> ORGANISM: Artificial Sequence
<220> FEATURE:
<223> OTHER INFORMATION: CDRH residues

<400> SEQUENCE: 3

Ser Tyr Trp Met Asn
1               5

<210> SEQ ID NO 4
<211> LENGTH: 17
<212> TYPE: PRT
<213> ORGANISM: Artificial Sequence
<220> FEATURE:
<223> OTHER INFORMATION: CDRH residues

<400> SEQUENCE: 4

Val Ile His Pro Ser Asp Ser Glu Thr Trp Leu Asp Gln Lys Phe Lys
1               5                   10                  15

Asp

<210> SEQ ID NO 5
<211> LENGTH: 10
<212> TYPE: PRT
<213> ORGANISM: Artificial Sequence
<220> FEATURE:
<223> OTHER INFORMATION: CDRH residues

<400> SEQUENCE: 5

Glu His Tyr Gly Thr Ser Pro Phe Ala Tyr
```

<210> SEQ ID NO 6
<211> LENGTH: 326
<212> TYPE: PRT
<213> ORGANISM: Artificial Sequence
<220> FEATURE:
<223> OTHER INFORMATION: Constant region

<400> SEQUENCE: 6

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 7
<211> LENGTH: 15
<212> TYPE: PRT

```
<213> ORGANISM: Artificial Sequence
<220> FEATURE:
<223> OTHER INFORMATION: CDRL residues

<400> SEQUENCE: 7

Arg Ala Ser Glu Ser Val Asp Asn Tyr Gly Met Ser Phe Met Asn
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: CDRL residues

<400> SEQUENCE: 8

Ala Ala Ser Asn Gln Gly Ser
1               5

<210> SEQ ID NO 9
<211> LENGTH: 9
<212> TYPE: PRT
<213> ORGANISM: Artificial Sequence
<220> FEATURE:
<223> OTHER INFORMATION: CDRL residues

<400> SEQUENCE: 9

Gln Gln Ser Lys Glu Val Pro Tyr Thr
1               5

<210> SEQ ID NO 10
<211> LENGTH: 107
<212> TYPE: PRT
<213> ORGANISM: Artificial Sequence
<220> FEATURE:
<223> OTHER INFORMATION: Constant region

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

PHARMACEUTICAL COMPOSITIONS OF A PD-1 ANTIBODY AND USE OF THE SAME

CROSS-REFERENCE TO RELATED APPLICATION

This application claims priority from U.S. Provisional Patent Application No. 63/220,006, filed Jul. 9, 2021. The contents of this application is incorporated herein by reference in its entirety.

REFERENCE TO SEQUENCE LISTING

This application includes one or more Sequence Listings pursuant to 37 C.F.R. 1.821 et seq., which are disclosed herein. The Sequence Listing has been submitted electronically in ASCII format and is hereby incorporated by reference in its entirety. The ASCII copy, created on Sep. 1, 2022, is named 123908_0267_Sequence_Listing.txt and is 11 kb in size.

FIELD

The present disclosure provides pharmaceutical compositions, for storage and administration, comprising an anti-human PD-1 ("hPD-1") antibody ("retifanlimab") and buffering agents. The disclosure further provides containers and kits comprising such pharmaceutical compositions. The disclosure further provides the use of such pharmaceutical compositions, containers, and kits containing retifanlimab for the treatment of a cancer, and in certain aspects treatment of a cancer expressing PD-L1.

BACKGROUND

Programmed Death-1 ("PD-1," also known as "CD279") is an immune checkpoint protein that is expressed on the surface of activated T-cells, B-cells and monocytes. PD-1 mediates its inhibition of the immune system by binding to the transmembrane protein ligands: Programmed Death-Ligand 1 ("PD-L1," also known as "B7-H1") and Programmed Death-Ligand 12 ("PD-L2," also known as "B7-DC"). In normal circumstances the immune checkpoint protein serves as the acting target for inhibiting the overactivation of T cells, and thus acts to prevent autoimmune damage. However, when its ligand is expressed by tumor cells, binding to its ligand serves to prevent immune system cells from approaching the tumor, and thus weakens the ability of the immune system to recognize and destroy tumor cells. Accordingly, the expression of PD-L1 on tumor cells is often associated with poor prognosis. The role of PD-1 ligand interactions in inhibiting T-cell activation and proliferation suggests that these biomolecules might serve as therapeutic targets for treatments of inflammation and cancer. Thus, the use of antibodies to PD-1 and its ligand, particularly PD-L1, to treat infections and tumors and up-modulate an adaptive immune response has been proposed. Antibodies capable of specifically binding to PD-1 and PD-L1 have been reported.

However, an unmet need remains to develop antibody compositions for patients whose tumors express PD-L1, including those whose tumors express low levels of PD-L1 or who have failed on other PD-1 therapies. The present disclosure directly addresses this need and others, as described below.

SUMMARY

In one embodiment, the present disclosure provides pharmaceutical compositions, for storage and administration, comprising an anti-human PD-1 ("hPD-1") antibody ("retifanlimab") and buffering agents. The disclosure further provides containers and kits comprising such pharmaceutical compositions. The disclosure further provides the use of such pharmaceutical compositions, containers, and kits containing retifanlimab for the treatment of a cancer, and in certain embodiments treatment of a cancer expressing PD-L1, for example with a therapeutically effective amount or prophylactically effective amount of retinfanlimab.

In one embodiment, the disclosure provides a pharmaceutical composition comprising retifanlimab, acetate, sucrose, polysorbate 80 ("PS80"), and water. In certain embodiments, the disclosure provides an embodiment of such pharmaceutical compositions, wherein the acetate is present at a concentration of about 5 mM to about 30 mM. The disclosure further provides an embodiment of such pharmaceutical compositions, wherein the acetate comprises sodium acetate, or wherein the acetate comprises glacial acetic acid and sodium acetate.

The disclosure additionally provides an embodiment of such pharmaceutical compositions, wherein the composition comprises:
a) about 5 mM to about 30 mM acetate, about 50 mg/mL to about 130 mg/mL of sucrose, about 0.02 mg/mL to about 0.6 mg/mL of PS80, and water, wherein the composition has a pH of about 4.0 to about 6.5; or
b) about 7.5 mM to about 20 mM acetate, about 50 mg/mL to about 130 mg/mL of sucrose, about 0.05 mg/mL to about 0.6 mg/mL of PS80, and water, wherein the composition has a pH of about 4.0 to about 6.5; or
c) about 9 mM to about 11 mM acetate, about 76 mg/mL to about 104 mg/mL of sucrose, about 0.08 mg/mL to about 0.53 mg/mL of PS80, and water, wherein the composition has a pH of about 4.5 to about 5.7; or
d) about 9 mM to about 11 mM acetate, about 80 mg/mL to about 100 mg/mL of sucrose, about 0.08 mg/mL to about 0.15 mg/mL of PS80, and water, wherein the composition has a pH of about 4.5 to about 5.7.

The disclosure provides an embodiment of such pharmaceutical compositions, wherein retifanlimab is present at a concentration of about 10 mg/mL to about 100 mg/mL. The disclosure further provides an embodiment of such pharmaceutical compositions, wherein retifanlimab is present at a concentration of about 20 mg/mL to about 30 mg/mL. The disclosure further provides an embodiment of such pharmaceutical compositions, wherein retifanlimab is present at a concentration of about 25 mg/mL.

The disclosure provides an embodiment of such pharmaceutical composition, wherein the acetate comprises glacial acetic acid at a concentration of about 0.05 mg/mL to about 0.35 mg/mL and sodium acetate trihydrate at a concentration of about 0.80 mg/mL to about 2.0 mg/mL. The disclosure further provides an embodiment of pharmaceutical compositions, wherein the acetate comprises glacial acetic acid at a concentration of about 0.18 mg/mL and sodium acetate trihydrate at a concentration of about 0.95 mg/mL.

The disclosure provides an embodiment of such pharmaceutical compositions, wherein the sucrose is present at a concentration of about 80 mg/mL to about 100 mg/mL. The disclosure further provides an embodiment of such pharmaceutical compositions, wherein the sucrose is present at a concentration of about 90 mg/mL.

The disclosure provides an embodiment of such pharmaceutical compositions, wherein the PS80 is present at a concentration of about 0.08 mg/mL to about 0.15 mg/mL.

The disclosure further provides an embodiment of such pharmaceutical compositions, wherein the concentration of PS80 is about 0.1 mg/mL.

The disclosure provides an embodiment of such pharmaceutical compositions, wherein the composition has a pH of about 4.5 to about 5.7. The disclosure further provides an embodiment of such pharmaceutical compositions, wherein the composition has a pH of about 5.1.

The disclosure provides an embodiment of such pharmaceutical compositions, wherein the composition comprises about 25 mg/mL of retifanlimab, about 0.18 mg/mL of glacial acetic acid, about 0.95 mg/mL of sodium acetate trihydrate, about 90 mg/mL of sucrose, about 0.1 mg/mL of PS80, and water, wherein the composition has a pH of about 4.8 to about 5.4.

The disclosure provides an embodiment of such pharmaceutical compositions, wherein the composition has a shelf-life of at least about 18 months at about 2° C. to about 8° C. The disclosure further provides an embodiment of such pharmaceutical compositions, wherein the composition has a shelf-life of about 24 months at about 2° C. to about 8° C. The disclosure further provides an embodiment of such pharmaceutical compositions, wherein the composition has a shelf-life of about 36 months at about 2° C. to about 8° C. The disclosure further provides an embodiment of such pharmaceutical compositions, wherein the composition has a shelf-life of about 48 months at about 2° C. to about 8° C. The disclosure further provides an embodiment of such pharmaceutical compositions, wherein the composition has a shelf-life of about 60 months at about 2° C. to about 8° C.

The disclosure provides an embodiment of such pharmaceutical compositions, wherein the composition has an osmolality of about 200 to about 400 mOsm/kg $H_2O$. The disclosure further provides an embodiment of such pharmaceutical compositions, wherein the composition has an osmolality of about 225 to about 400 mOsm/kg $H_2O$. The disclosure further provides an embodiment of such pharmaceutical compositions, wherein the composition has an osmolality of about 250 to about 375 mOsm/kg $H_2O$. The disclosure further provides an embodiment of such pharmaceutical compositions, wherein the composition has an osmolality of about 260 to about 340 mOsm/kg $H_2O$.

The disclosure provides an embodiment of such pharmaceutical compositions, wherein the composition maintains monomeric purity of the retifanlimab for about for at least about 3 months at about 25° C. The disclosure further provides an embodiment of such pharmaceutical compositions, wherein the composition maintains monomeric purity of the retifanlimab for about for at least about 18 months at about 2° C. to about 8° C.

The disclosure provides an embodiment of such pharmaceutical compositions, wherein the composition maintains the heterogeneity profile of the retifanlimab for about for at least about 3 months at 25° C. The disclosure further provides an embodiment of such pharmaceutical compositions, wherein the composition maintains the heterogeneity profile of the retifanlimab for about for at least about 18 months at about 2° C. to about 8° C.

The disclosure further provides an embodiment of any of the pharmaceutical compositions disclosed herein, wherein the water is sterile, nonpyrogenic, distilled water.

The disclosure further provides an embodiment of the pharmaceutical compositions disclosed herein, wherein the pharmaceutical composition is sterile.

The disclosure additionally provides a container comprising any of the pharmaceutical compositions disclosed herein, wherein such container comprises about 10 mL volume, about 15 mL volume, or about 20 mL of such pharmaceutical compositions.

The disclosure further provides an embodiment of such pharmaceutical compositions, wherein the pharmaceutical compositions do not comprise an antioxidant.

The disclosure provides an embodiment of such a container, wherein the about 10 mL volume of such a pharmaceutical composition comprises: (a) about 250 mg retifanlimab; (b) about 1.8 mg glacial acetic acid; (c) about 9.5 mg sodium acetate trihydrate; (d) about 900 mg sucrose; (e) about 1 mg PS80; and (f) water; and wherein such composition has a pH of about 4.8 to about 5.4.

The disclosure further provides an embodiment of such a container, wherein the about 15 mL volume of such a pharmaceutical composition comprises: (a) about 375 mg retifanlimab; (b) about 2.7 mg glacial acetic acid; (c) about 14.25 mg sodium acetate trihydrate; (d) about 1350 mg sucrose; (e) about 1.5 mg PS80; and (f) water; and wherein the composition has a pH of about 4.8 to about 5.4.

The disclosure further provides an embodiment of such a container, wherein the about 20 mL volume of such a pharmaceutical composition comprises: (a) about 500 mg retifanlimab; (b) about 3.6 mg glacial acetic acid; (c) about 19 mg sodium acetate trihydrate; (d) about 1800 mg sucrose; (e) about 2 mg PS80; and (f) water; and wherein the composition has a pH of about 4.8 to about 5.4.

The disclosure additionally provides a kit comprising any of the pharmaceutical compositions disclosed herein, or any of the containers disclosed herein, and optionally comprising instructions for administration of the pharmaceutical composition to a subject in need thereof.

The disclosure additionally provides a kit comprising a container comprising a pharmaceutical composition, the composition comprising:

a) about 21 mg/mL to about 29 mg/mL of retifanlimab, about 0.16 mg/mL to about 0.20 mg/mL of glacial acetic acid, about 0.86 mg/mL to about 1.1 mg/mL of sodium acetate trihydrate, about 76 mg/mL to about 104 mg/mL of sucrose, about 0.08 mg/mL to about 0.53 mg/mL of PS80, and water, wherein the composition has a pH of about 4.5 to about 5.7; or b) about 22.5 mg/mL to about 27.5 mg/mL of retifanlimab, about 0.16 mg/mL to about 0.20 mg/mL of glacial acetic acid, about 0.86 mg/mL to about 1.1 mg/mL of sodium acetate trihydrate, about 76 mg/mL to about 104 mg/mL of sucrose, about 0.08 mg/mL to about 0.53 mg/mL of PS80, and water, wherein the composition has a pH of about 4.5 to about 5.7; or c) about 250 mg retifanlimab, about 1.8 mg glacial acetic acid, about 9.5 mg sodium acetate trihydrate, about 900 mg sucrose, about 1 mg PS80, and wherein the composition has a pH of about 4.8 to about 5.4; or d) about 375 mg retifanlimab, about 2.7 mg glacial acetic acid, about 14.25 mg sodium acetate trihydrate, about 1350 mg sucrose, about 1.5 mg PS80, and wherein the composition has a pH of about 4.8 to about 5.4; or e) about 500 mg retifanlimab, about 3.6 mg glacial acetic acid, about 19 mg sodium acetate trihydrate, about 1800 mg sucrose, about 2 mg PS80, and wherein the composition has a pH of about 4.8 to about 5.4; and optionally comprising instructions for administration of the pharmaceutical composition to a subject in need thereof.

The disclosure provides an embodiment of such kits, wherein the composition comprises about 25 mg/mL of retifanlimab, about 0.18 mg/mL of glacial acetic acid, about 0.95 mg/mL of sodium acetate trihydrate, about 90 mg/mL of sucrose, about 0.1 mg/mL of PS80, and water, wherein the composition has a pH of about 4.8 to about 5.4.

The disclosure provides an embodiment of such kits, wherein the composition comprises about 250 mg retifanlimab, about 1.8 mg glacial acetic acid, about 9.5 mg sodium acetate trihydrate, about 900 mg sucrose, about 1 mg PS80, and wherein the composition has a pH of 4.8 to 5.4. The disclosure further provides an embodiment of such kits, wherein the composition comprises about 375 mg retifanlimab, about 2.7 mg glacial acetic acid, about 14.25 mg sodium acetate trihydrate, about 1350 mg sucrose, about 1.5 mg PS80, and wherein the composition has a pH of about 4.8 to about 5.4.

The disclosure provides an embodiment of such kits, wherein the composition comprises about 500 mg retifanlimab, about 3.6 mg glacial acetic acid, about 19 mg sodium acetate trihydrate, about 1800 mg sucrose, about 2 mg PS80, and wherein the composition has a pH of about 4.8 to about 5.4.

The disclosure additionally provides a sealed package comprising any of the pharmaceutical compositions disclosed herein, any of the containers disclosed herein, or any of the kits disclosed herein, and optionally further comprising instructions for administration of the pharmaceutical composition to a subject in need thereof.

The disclosure further provides a method of treating cancer, comprising administering retifanlimab to a subject in need thereof using any of the pharmaceutical compositions disclosed herein, any of the containers disclosed herein, and of the kits disclosed herein, or any of the sealed kits disclosed herein.

The disclosure additionally provides a method of treating cancer, comprising administering retifanlimab to a subject in need thereof using any of the pharmaceutical compositions disclosed herein, any of the containers disclosed herein, any of the sealed packages disclosed herein, or any of the kits disclosed herein, wherein such a method comprises:
  a) diluting the pharmaceutical composition in a container:
    in 0.9% sodium chloride, or
    in 5% dextrose in water (D5W),
    to obtain a dosing solution;
  b) inverting the container to mix the diluted solution; and
  c) attaching the container containing the dosing solution to a device for administration to the subject.

The disclosure also provides the use of any of the pharmaceutical compositions disclosed herein, any of the containers disclosed herein, any of the sealed packages disclosed herein, or any of the kits disclosed herein, for the treatment of cancer in a subject in need thereof.

The disclosure additionally provides the use of any of the pharmaceutical compositions disclosed herein, any of the containers disclosed herein, any of the sealed packages disclosed herein, or any of the kits disclosed herein, for the treatment of cancer in a subject in need thereof, wherein the use comprises:
  a) diluting the pharmaceutical composition in a container:
    in 0.9% sodium chloride; or
    in 5% dextrose in water (D5W),
    to obtain a dosing solution;
  b) inverting the container to mix the diluted solution; and
  c) attaching the container containing the dosing solution to a device for administration to the subject.

The disclosure further provides an embodiment of the methods or uses of the present disclosure, wherein the container is an IV bag containing 0.9% sodium chloride. The disclosure further provides an embodiment of such uses, wherein the container is an IV bag containing D5W.

The disclosure provides an embodiment any of the methods disclosed herein, or any of the uses disclosed herein, wherein the dosing solution maintains monomeric purity of the retifanlimab for about 6 hours at 25° C. or for about 24 hours at about 2° C. to about 8° C.

The disclosure provides an embodiment any of the methods disclosed herein, or any of the uses disclosed herein, wherein the administration is by IV infusion for at least 30 minutes. The disclosure further provides an embodiment any of the methods disclosed herein, or any of the uses disclosed herein, wherein the administration is by IV infusion for at least 60 minutes.

The disclosure provides an embodiment any of the methods disclosed herein, or any of the uses disclosed herein, wherein the pharmaceutical composition is diluted to obtain a flat dose of about 375 mg. The disclosure further provides an embodiment any of the methods disclosed herein or any of the uses disclosed herein, wherein the pharmaceutical composition is diluted to obtain a flat dose of about 500 mg.

The disclosure provides an embodiment any of the methods disclosed herein, or any of the uses disclosed herein, wherein administration of the dosing solution is once every 2 weeks, or once every 3 weeks, or once every 4 weeks.

The disclosure provides an embodiment any of the methods disclosed herein, or any of the uses disclosed herein, wherein the cancer expresses PD-L1.

The disclosure provides an embodiment any of the methods disclosed herein, or any of the uses disclosed herein, wherein the cancer is selected from the group consisting of: adrenal gland cancer, AIDS-associated cancer, alveolar soft part sarcoma, anal cancer, squamous cell carcinoma of the anal canal (SCAC), bladder cancer, bone cancer, brain and spinal cord cancer, breast cancer, HER2+ breast cancer or Triple-Negative Breast Cancer (TNBC), carotid body tumor, cervical cancer, HPV-related cervical cancer, chondrosarcoma, chordoma, chromophobe renal cell carcinoma, clear cell carcinoma, colon cancer, colorectal cancer, desmoplastic small round cell tumor, ependymoma, endometrial cancer, unselected endometrial cancer, MSI-high endometrial cancer, dMMR endometrial cancer, DNA polymerase ε (POLE) exonuclease domain mutation positive endometrial cancer, Ewing's sarcoma, extraskeletal myxoid chondrosarcoma, gallbladder or bile duct cancer, cholangiocarcinoma bile duct cancer, gastric cancer, gastroesophageal junction (GEJ) cancer, gestational trophoblastic disease, germ cell tumor, glioma, glioblastoma, head and neck cancer, squamous cell carcinoma of head and neck (SCCHN), a hematological malignancy, a hepatocellular carcinoma, islet cell tumor, Kaposi's Sarcoma, kidney cancer, renal cell carcinomas (RCC), clear cell RRC, papillary RCC and chromophobe RCC, leukemia, acute myeloid leukemia, liposarcoma/malignant lipomatous tumor, liver cancer, hepatocellular carcinoma liver cancer (HCC), lymphoma, diffuse large B-cell lymphoma (DLBCL), non-Hodgkin's lymphoma (NHL), lung cancer, small cell lung cancer (SCLC), non-small cell lung cancer (NSCLC), medulloblastoma, melanoma, uveal melanoma, meningioma, mesothelioma, mesothelial pharyngeal cancer, multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pharyngeal cancer, pheochromocytoma, pituitary tumor, prostate cancer, metastatic castration resistant prostate cancer (mCRPC), posterious uveal melanoma, renal metastatic cancer, rhabdoid tumor, rhabdomyosarcoma, sarcoma, skin cancer, Merkel cell carcinoma, a small round blue cell tumor of childhood, neuroblastoma, rhabdomyosarcoma, soft-tissue sarcoma, squamous cell cancer, stomach cancer, synovial sarcoma, testicular cancer, thymic carcinoma, thymoma, thyroid cancer, urothelial cancer, and uterine cancer.

The disclosure provides an embodiment any of the methods disclosed herein, or any of the uses disclosed herein, wherein the cancer is anal cancer, breast cancer, colorectal cancer, endometrial cancer, gastric cancer, GEJ cancer, head and neck cancer, kidney cancer, liver cancer, lung cancer, lymphoma, melanoma, multiple myeloma, ovarian cancer, pancreatic cancer, prostate cancer, and skin cancer, and urothelial cancer. The disclosure further provides an embodiment any of the methods disclosed herein, or any of the uses disclosed herein, wherein the cancer is SCAC, NSCLC, MSI-high endometrial cancer, dMMR endometrial cancer, POLE exonuclease domain mutation positive endometrial cancer, melanoma, Merkel cell carcinoma, SCCHN, mCRPC, RCC, clear cell RCC, or urothelial cancer.

The disclosure further provides an embodiment of any of the methods disclosed herein, or any of the uses disclosed herein, wherein the subject is a human subject.

Both the foregoing summary and the following description of the drawings and detailed description are exemplary and explanatory. They are intended to provide further details of the disclosure, but are not to be construed as limiting. Other objects, advantages, and novel features will be readily apparent to those skilled in the art from the following detailed description of the disclosure.

BRIEF DESCRIPTION OF THE FIGURES

FIG. 1 shows the prediction profiler for the formulations stored at 5±3° C. for 6 months (2-8° C. 6 M). High molecular weight species (HMWS), monomer, acidic variants (AV), main charge peak (MP), basic variants (BV), sub-visible particles (≥10 μm and ≥25 μm) are plotted (rows) over changes in sucrose concentration, pH, PS-80 concentration, retifanlimab concentration, and ionic strength (columns).

DETAILED DESCRIPTION

The present disclosure provides pharmaceutical compositions, for storage and administration, comprising a human PD-1 ("hPD-1") antibody ("retifanlimab") and buffering agents. The disclosure further provides containers and kits comprising such pharmaceutical compositions. The disclosure further provides the use of such pharmaceutical compositions, containers, and kits containing retifanlimab for the treatment of a cancer, and in certain embodiments treatment of a cancer expressing PD-L1, for example with a therapeutically effective amount or prophylactically effective amount of retinfanlimab.

Retifanlimab (also known as MGA012 and INCMGA00012; CAS Reg No. 2079108-44-2) is a humanized hinge-stabilized IgG4κ monoclonal antibody that recognizes and binds to human PD-1 expressed by T and B-lymphocytes. Retifanlimab contains a human IgG4 Fc region containing a serine to proline mutation in the hinge region (S228P) to reduce or eliminate hinge inter-chain disulfide instability, wherein the numbering of the residues in an IgG heavy chain is that of the EU index as in Kabat (Kabat, *Sequences Of Proteins Of Immunological Interest* (National Institutes of Health, Bethesda, Md., 1987 and 1991), and refers to the numbering of the human IgG4 EU antibody. The amino acid sequences of the heavy and light chains of retifanlimab are presented below (WHO Drug Information 2019, Proposed INN: List 121, 33(2)):326-327). The CDRs as defined by Kabat are underlined.

The amino acid sequence of the Heavy Chain of Retifanlimab is (SEQ ID NO:1) (CDR$_H$ residues are shown bolded and underlined; the constant region is shown with double underline, the S228P mutation is shown bolded and double underlined):

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSA

STKGPSVFPL APCSRSTSES TAALGCLVKD YFPEPVTVSW

NSGALTSGVH TFPAVLQSSG LYSLSSVVTV PSSSLGTKTY

TCNVDHKPSN TKVDKRVESK YGPPCPPCPA PEFLGGPSVF

LFPPKPKDTL MISRTPEVTC VVVDVSQEDP EVQFNWYVDG

VEVHNAKTKP REEQFNSTYR VVSVLTVLHQ DWLNGKEYKC

KVSNKGLPSS IEKTISKAKG QPREPQVYTL PPSQEEMTKN

QVSLTCLVKG FYPSDIAVEW ESNGQPENNY KTTPPVLDSD

GSFFLYSRLT VDKSRWQEGN VFSCSVMHEA LHNHYTQKSL

SLSLG
```

The amino acid sequence of the Light Chain of Retifanlimab is (SEQ ID NO:2) (CDR$_L$ residues are shown bolded and underlined; the constant region is shown with double underline):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

The pharmaceutical compositions of the disclosure comprise retifanlimab, buffering agents and stabilizers, and are also referred herein as "retifanlimab compositions".

As used herein, "about" will be understood by persons of ordinary skill in the art and will vary to some extent depending upon the context in which it is used. If there are uses of the term which are not clear to persons of ordinary skill in the art and which are not otherwise defined herein, given the context in which it is used, "about" will mean up to plus or minus 10% of the particular term.

As used herein, the singular forms "a," "an" and "the" include plural referents unless the context clearly dictates otherwise. Thus, for example, reference to "a" component includes embodiments having two or more such components, unless the context clearly indicates otherwise. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items. Moreover, terms used in the specification and claims such as have, having, include, and including should be construed to be synonymous with the terms comprise and comprising. Other elements may optionally be present other than the elements specifically identified by the "and/or" clause, whether related or unrelated to those elements specifically identified. As a non-limiting example, a reference to "X and/or Y" may refer, in one embodiment, to X only (optionally including elements other than Y); in some embodiments, to Y only (optionally including elements other than X); in yet some embodiments, to both X and Y (optionally including other elements).

As used herein, "acetate" refers to the acetate component of a pharmaceutical composition. For example, the acetate component can be made up of acetic acid, acetate salts, and/or an acetate buffer.

As used herein, the term "aqueous" refers to a water-containing solution.

As used herein, the term "stable" refers to retifanlimab substantially retaining its physical stability, chemical stability, pharmaceutical activity and/or its biological activity, upon storage.

The term "shelf-life" refers to the period of time during which the pharmaceutical compositions can be stored, in which physical stability, chemical stability, pharmaceutical activity and/or biological activity are/is substantially retained.

As will be understood by one skilled in the art, for any and all purposes, particularly in terms of providing a written description, all ranges disclosed herein also encompass any and all possible subranges and combinations of subranges thereof, inclusive of the endpoints. As such, all disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like, include the number recited and refer to ranges which may be subsequently broken down into subranges as discussed herein. Further, as will be understood by one skilled in the art, a range includes each individual member. Thus, for example, a group having 1-3 layers refers to groups having 1, 2, or 3 layers. Similarly, a group having 1-5 layers refers to groups having 1, 2, 3, 4, or 5 layers, and so forth.

The embodiments illustratively disclosed herein may suitably be practiced in the absence of any element or elements, limitation or limitations not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

Definitions that are contained in text incorporated by reference are excluded to the extent that they contradict definitions in this disclosure.

The present disclosure provides pharmaceutical compositions that substantially retain the physical and chemical stability, of retifanlimab as well as its pharmaceutical activity and/or biological activity upon storage. In one embodiment, about 90% or more, about 80% or more, about 70% or more, or about 60% or more of the physical stability, chemical stability, pharmaceutical activity and/or biological activity of retifanlimab is retained during storage of a pharmaceutical composition of the disclosure. In one embodiment, during the shelf-life time period, about 90% or more, about 85% or more, about 80% or more, about 75% or more, about 70% or more, about 65% or more, or about 60% or more of the physical stability, chemical stability, pharmaceutical activity and/or biological activity of retifanlimab is retained. The shelf-life of a pharmaceutical composition is generally selected based on the period of time a molecule is stable in such composition.

In one embodiment, the shelf-life of a pharmaceutical composition of the disclosure is at least about 1 month at about 25° C., at least about 2 months at about 25° C., at least about 3 months at about 25° C., at least about 4 months at about 25° C., at least about 6 months at about 25° C., or at least about 7, at least about 8, at least about 9, at least about 10, at least about 11, or at least about 12 months at about 25° C. In another embodiment, the shelf-life of a pharmaceutical composition of the disclosure is at least about 6 months, at least about 12 months, at least about 18 months, at least about 24 months, at least about 30 months, at least about 36 months, at least about 48 months, or at least about 60 months, all at about 2° C. to about 8° C. In one embodiment, the shelf-life of a pharmaceutical composition of the disclosure is at least about 6 months at about 25° C. In another embodiment, the shelf-life of a pharmaceutical composition of the disclosure is at least about 24 months at about 2° C. to about 8° C. In another embodiment, the shelf-life of a pharmaceutical composition of the disclosure is at least about 36 months at about 2° C. to about 8° C. In another embodiment, the shelf-life of a pharmaceutical composition of the disclosure is at least about 48 months at about 2° C. to about 8° C. In another embodiment, the shelf-life of a pharmaceutical composition of the disclosure is at least about 60 months at about 2° C. to about 8° C.

One measure of physical and chemical stability is the monomeric purity of retifanlimab in pharmaceutical compositions of the disclosure or in a dosing solution of the disclosure. The monomeric purity of retifanlimab can be determined by evaluating the amount of protein in such composition or solution having the expected molecule weight (monomeric retifanlimab), species with a molecular weight greater than the monomer (HMW), and/or species having a molecular weight lower than the monomer (LMW) by any suitable method. Thus, the loss of monomeric purity can be measured by determining the loss of retifanlimab protein having the expected molecule weight (monomer), and/or the accumulation of BMW, and/or LMW species after the indicated period of time. In certain embodiments, the percent (%) of each species (monomer, HMW, and LMW) is calculated as the percent (%) of the total protein. In one embodiment, the loss of monomeric purity of retifanlimab in a pharmaceutical composition of the disclosure or in a dosing solution of the disclosure is about 15% or less, or about 10% or less, or about 5% or less, or about 4% or less, or about 3% or less, or about 2% or less, or about 1% or less, over the indicated period of time. In one embodiment, the loss of monomeric purity of retifanlimab in a pharmaceutical composition of the disclosure or in a dosing solution of the disclosure is about 5% or less over the indicated period of time. In another embodiment, the loss of monomeric purity of retifanlimab in a pharmaceutical composition of the disclosure or in a dosing solution of the disclosure is less than about 4% over the indicated period of time. In another embodiment, the loss of monomeric purity of retifanlimab in a pharmaceutical composition of the disclosure or in a dosing solution of the disclosure is about 3% or less over the indicated period of time. In another embodiment, the loss of monomeric purity of retifanlimab in a pharmaceutical composition of the disclosure or in a dosing solution of the disclosure is about 2% or less over the indicated period of time. In certain embodiments, the amount of monomer, HMW and/or LMW species of the retifanlimab in a composition of the disclosure or in a dosing solution of the disclosure is measured via size exclusion high performance liquid chromatography (SE-HPLC). In such embodiment, the percent (%) of each species is calculated as the area of the SE-HPLC species peak (i.e., monomer, HMW, LMW), divided by the sum of all peaks, the percent (%) of the total protein.

In other embodiments, the monomeric purity of retifanlimab in a pharmaceutical composition of the disclosure is maintained for at least about 1 month at about 25° C., at least about 2 months at about 25° C., at least about 3 months at about 25° C., at least about 4 months at about 25° C., at least about 6 months at about 25° C., at least about 6 months at about 2° C. to about 8° C., at least about 12 months at about 2° C. to about 8° C., at least about 18 months at about 2° C. to about 8° C., at least about 24 months at about 2° C. to about 8° C., at least about 30 months about 2° C. to about 8° C., at least about 36 months about 2° C. to about 8° C., at least about 48 months, at least about 60 months, or more than about 60 months at about 2° C. to about 8° C. In one embodiment, monomeric purity of retifanlimab in a pharmaceutical composition of the disclosure is maintained at least about 6 months at about 25° C. In another embodiment, monomeric purity of retifanlimab in a pharmaceutical composition of the disclosure is maintained for about 36 months or more at about 2° C. to about 8° C. In another embodiment, the monomeric purity of retifanlimab in a pharmaceutical composition of the disclosure is maintained for about 48 months at about 2° C. to about 8° C. In another embodiment, the monomeric purity of retifanlimab in a pharmaceutical composition of the disclosure is maintained for about 60 months at about 2° C. to about 8° C.

Another measure of stability is the stability of the charge heterogeneity profile of retifanlimab in a pharmaceutical composition of the disclosure or in a dosing solution of the disclosure. Protein compositions may comprise a variety of variants that differ in their isoelectric point (pI). Such variants are referred to as charge variants. Thus, the heterogeneity profile can be determined by measuring the main charge peak (MCP), the acidic variants (AV), and the basic variants (BV) by any suitable method. For example, a retifanlimab composition of the disclosure can comprise MCP, AV and BV components, and changes to the heterogeneity profile can be measured by determining the loss of the MCP and/or the accumulation of AV, and/or BV after the indicated time. In one embodiment, the decrease in the MCP of retifanlimab in a pharmaceutical composition of the disclosure or in a dosing solution of the disclosure is about 15% or less, or about 10% or less, or about 5% or less, or about 4% or less, or about 3% or less, or about 2% or less, or about 1% or less, over the indicated period of time. In one embodiment, the increase in the AV of retifanlimab in a pharmaceutical composition of the disclosure or in a dosing solution of the disclosure is about 15% or less, or about 10% or less, or about 5% or less, or about 4% or less, or about 3% or less, or about 2% or less, or about 1% or less, over the indicated period of time. In another embodiment, the increase in the BV of retifanlimab in a pharmaceutical composition of the disclosure or in a dosing solution of the disclosure is about 15% or less, or about 10% or less, or about 5% or less, or about 4% or less, or about 3% or less, or about 2% or less, or about 1% or less, over the indicated period of time. In another embodiment, the decrease in the MCP of retifanlimab in a pharmaceutical composition of the disclosure or in a dosing solution of the disclosure is about 7% or less over the indicated period of time. In another embodiment, the decrease in the MCP of retifanlimab in a pharmaceutical composition of the disclosure or in a dosing solution of the disclosure is about 6% or less over the indicated period of time. In another embodiment, the decrease in the MCP of retifanlimab in a pharmaceutical composition of the disclosure or in a dosing solution of the disclosure is about 5% or less over the indicated period of time. In another embodiment, the increase in the AV of retifanlimab in a pharmaceutical composition of the disclosure or in a dosing of the disclosure is about 7% or less over the indicated period of time. In another embodiment, the increase in the AV of retifanlimab in a pharmaceutical composition of the disclosure or in a dosing solution of the disclosure is about 6% or less over the indicated period of time. In another embodiment, the increase in the AV of retifanlimab in a pharmaceutical composition of the disclosure or in a dosing solution of the disclosure is about 5% or less over the indicated period of time. In another embodiment, the increase in the BV of retifanlimab in a pharmaceutical composition of the disclosure or in a dosing solution of the disclosure is about 4% or less over the indicated period of time. In another embodiment, the increase in the BV of retifanlimab in a pharmaceutical composition of the disclosure or in a dosing solution of the disclosure is about 3% or less over the indicated period of time. In another embodiment, the increase in the BV of retifanlimab in a pharmaceutical composition of the disclosure or in a dosing solution of the disclosure is about 2% or less over the indicated period of time. In certain embodiments, the MCP, AV, and BV of the retifanlimab in a pharmaceutical composition of the disclosure or in a dosing solution of the disclosure is measured via capillary isoelectric focusing (cIEF).

In other embodiments, the heterogeneity profile of retifanlimab in a pharmaceutical composition of the disclosure is maintained for at least about 1 month at about 25° C., at least about 2 months at about 25° C., at least about 3 months at about 25° C., at least about 4 months at about 25° C., at least about 6 months at about 25° C., at least about 6 months at about 2° C. to about 8° C., at least about 12 months at about 2° C. to about 8° C., at least about 18 months at about 2° C. to about 2-8° C., at least about 24 months at about 2°

C. to about 8° C., at least about 30 months about 2° C. to about 2-8° C., at least about 36 months about 2° C. to about 2-8° C., at least about 48 months, at least about 60 months, or more than about 60 months at about 2° C. to about 8° C. In one embodiment, heterogeneity profile of retifanlimab in a pharmaceutical composition of the disclosure is maintained at least about 6 months at about 25° C. In another embodiment, heterogeneity profile of retifanlimab in a pharmaceutical composition of the disclosure is maintained for about 36 months or more at about 2° C. to about 8° C. In another embodiment, the heterogeneity profile of retifanlimab in a pharmaceutical composition of the disclosure is maintained for about 48 months at about 2° C. to about 8° C. In another embodiment, the heterogeneity profile of retifanlimab in a pharmaceutical composition of the disclosure is maintained for about 60 months at about 2° C. to about 8° C.

The components of the pharmaceutical compositions (i.e., retifanlimab compositions) of the disclosure can be supplied mixed together in unit dosage form, for example, as a liquid composition, in a hermetically sealed container such as a vial, ampoule, or sachet indicating the quantity of active agent. In one embodiment, a pharmaceutical composition of the disclosure is supplied as a liquid solution. Such liquid solution can be stored at between about 2° C. and about 8° C. in their original containers until ready to be administered, although such liquid solutions can be stored at room temperature (~25° C.) for short periods prior to administration.

In certain embodiments where a retifanlimab composition of the disclosure is to be administered by infusion, it can be dispensed, for example, with a container, bag, or infusion bottle containing sterile 0.9% sodium chloride (e.g., normal saline). In certain embodiments where a retifanlimab composition of the disclosure is administered by injection, 0.9% sodium chloride can be provided so that the ingredients can be mixed prior to administration as detailed herein. Such retifanlimab compositions can comprise a prophylactically or therapeutically effective amount of retifanlimab.

10071) In certain embodiments where a retifanlimab composition of the disclosure is to be administered by infusion, it can be dispensed with a container, bag, or infusion bottle containing sterile 5% dextrose in water ("D5W"). In certain embodiments where a retifanlimab composition of the disclosure is administered by injection, D5W can be provided so that the ingredients can be mixed prior to administration as detailed herein. Such retifanlimab compositions can comprise a prophylactically or therapeutically effective amount of retifanlimab.

In one embodiment, a pharmaceutical composition of the disclosure comprises retifanlimab, acetate, sucrose, PS80 and water. In certain embodiments, the pharmaceutical compositions of the disclosure do not comprise an antioxidant.

The acetate component can be made up of acetic acid and an acetate salt. Acceptable acetate salts include, but are not limited to: calcium acetate, magnesium acetate, potassium acetate, sodium acetate, and zinc acetate. In one embodiment, the acetate comprises glacial acetic acid, and sodium acetate.

In one embodiment, the pharmaceutical composition of the disclosure comprises retifanlimab at a concentration of about 10 mg/mL to about 100 mg/mL. In another embodiment, the pharmaceutical composition of the disclosure comprises retifanlimab at a concentration of about 20 mg/mL to about 30 mg/mL. In another embodiment, the pharmaceutical composition of the disclosure comprises retifanlimab at a concentration of about 22.5 mg/mL to about 27.5 mg/mL. In another embodiment, the pharmaceutical composition of the disclosure comprises retifanlimab at a concentration of about 25 mg/mL. Also contemplated are concentrations between any of these values, such as about 15 mg/mL, about 18 mg/mL, about 30 mg/mL, about 40 mg/mL, about 50 mg/mL, about 80 mg/mL etc.

In one embodiment, the pharmaceutical composition of the disclosure comprises about 5 mM to about 30 mM acetate. In another embodiment, the pharmaceutical composition of the disclosure comprises about 5 mM to about 25 mM acetate. In another embodiment, the pharmaceutical composition of the disclosure comprises about 7.5 mM to about 20 mM acetate. In another embodiment, the pharmaceutical composition of the disclosure comprises about 7.5 mM to about 15 mM acetate. In another embodiment, the pharmaceutical composition of the disclosure comprises about 9 mM to about 11 mM acetate. In another embodiment, the pharmaceutical composition of the disclosure comprises about 10 mM acetate. Also contemplated are concentrations between any of these values, such as about 8 mM, about 14 mM, about 18 mM, etc. In one embodiment, the acetate in the composition of the disclosure comprises glacial acetic acid and sodium acetate (e.g., sodium acetate anhydrous, sodium acetate monohydrate, and/or sodium acetate trihydrate). It will be appreciated that sodium acetate monohydrate and/or sodium acetate anhydrous and/or sodium acetate trihydrate can be used in combination with glacial acetic acid to obtain the desired acetate concentration. As provided herein, alternative forms of acetate can be used in place of sodium acetate in the acetate buffer, including but not limited to, magnesium acetate, potassium acetate, calcium acetate, and zinc acetate.

In one embodiment, the pharmaceutical composition of the disclosure comprises glacial acetic acid at a concentration of about 0.05 mg/mL to about 0.35 mg/mL. In another embodiment, the pharmaceutical composition of the disclosure comprises glacial acetic acid at a concentration of about 0.1 mg/mL to about 0.3 mg/mL. In another embodiment, the pharmaceutical composition of the disclosure comprises glacial acetic acid at a concentration of about 0.16 mg/mL to about 0.20 mg/mL. In still another embodiment, the pharmaceutical composition of the disclosure comprises glacial acetic acid at a concentration of about 0.18 mg/mL. Also contemplated are concentrations between any of these values, such as about 0.08 mg/mL, 0.15 mg/mL, 0.25 mg/mL, etc.

In one embodiment, the pharmaceutical composition of the disclosure comprises sodium acetate trihydrate at a concentration of about 0.8 mg/mL to about 2.0 mg/mL. In another embodiment, the pharmaceutical composition of the disclosure comprises sodium acetate trihydrate at a concentration of about 0.8 mg/mL to about 1.3 mg/mL. In another embodiment, the pharmaceutical composition of the disclosure comprises sodium acetate trihydrate at a concentration of about 0.86 mg/mL to about 1.1 mg/mL. In still another embodiment, the pharmaceutical composition of the disclosure comprises sodium acetate trihydrate at a concentration of about 0.95 mg/mL. Also contemplated are concentrations between any of these values, such as about 0.9 mg/mL, about 1.2 mg/mL, about 1.7 mg/mL, etc.

In one embodiment, the pharmaceutical composition of the disclosure comprises glacial acetic acid at a concentration of about 0.05 mg/mL to about 0.35 mg/mL and sodium acetate trihydrate at a concentration of about 0.5 mg/mL to about 2.0 mg/mL. In another embodiment, the pharmaceutical composition of the disclosure comprises glacial acetic acid at a concentration of about 0.1 mg/mL to about 0.3 mg/mL and sodium acetate trihydrate at a concentration of about 0.8 mg/mL to about 1.3 mg/mL. In another embodiment, the pharmaceutical composition of the disclosure comprises glacial acetic acid at a concentration of about 0.16 mg/mL to about 0.20 mg/mL and sodium acetate trihydrate at a concentration of about 0.86 mg/mL to about 1.1 mg/mL. In still another embodiment, the pharmaceutical composition of the disclosure comprises glacial acetic acid at a concentration of about 0.18 mg/mL and sodium acetate trihydrate at a concentration of about 0.95 mg/mL.

In one embodiment, the pharmaceutical composition of the disclosure comprises sucrose at a concentration of about 50 mg/mL to about 130 mg/mL sucrose. In another embodiment, the pharmaceutical composition of the disclosure comprises sucrose at a concentration of about 76 mg/mL to about 104 mg/mL. In another embodiment, the pharmaceutical composition of the disclosure comprises sucrose at a concentration of about 80 mg/mL to about 100 mg/mL. In still another embodiment, the pharmaceutical composition of the disclosure comprises sucrose at a concentration of about 90 mg/mL. Also contemplated are concentrations between any of these values, such as about 85 mg/mL, about 87 mg/mL, about 92 mg/mL, etc.

In one embodiment, the pharmaceutical composition of the disclosure comprises PS80 at a concentration of about 0.02 mg/mL to about 0.6 mg/mL. In another embodiment, the pharmaceutical composition of the disclosure comprises PS80 at a concentration of about 0.05 mg/mL to about 0.6 mg/mL. In another embodiment, the pharmaceutical composition of the disclosure comprises PS80 at a concentration of about 0.08 mg/mL to about 0.53 mg/mL. in another embodiment, the pharmaceutical composition of the disclosure comprises PS80 at a concentration of about 0.08 mg/mL to about 0.15 mg/mL. In another embodiment, the pharmaceutical composition of the disclosure comprises PS80 at a concentration about 0.1 mg/mL. Also contemplated are concentrations between any of these values, such as about 0.09 mg/mL, about 0.11 mg/mL, about 0.13 mg/mL, etc.

In one embodiment, the pharmaceutical composition of the disclosure has a pH of about 4.0 to about 6.5. In another embodiment, the pharmaceutical composition of the disclosure has a pH of about 4.5 to about 5.7. In another embodiment, the pharmaceutical composition of the disclosure has a pH of about 5.1. In another embodiment, the pharmaceutical composition of the disclosure has a pH of about 4.8 to about 5.4 (i.e., about 5.1±0.3). Also contemplated are pH amounts between any of these values, such as about 4.7, about 4.9, about 5.3, or about 5.5 pH, etc.

In one embodiment, the pharmaceutical composition of the disclosure comprises about 10 mg/mL to about 100 mg/mL of retifanlimab, about 5 mM to about 30 mM acetate, about 50 mg/mL to about 130 mg/mL of sucrose, about 0.02 mg/mL to about 0.6 mg/mL of PS80, and water, wherein the composition has a pH of about 4.0 to about 6.5. In another embodiment, the pharmaceutical composition of the disclosure comprises about 10 mg/mL to about 100 mg/mL of retifanlimab, about 7.5 mM to about 20 mM acetate, about 50 mg/mL to about 130 mg/mL of sucrose, about 0.05 mg/mL to about 0.6 mg/mL of PS80, and water, wherein the composition has a pH of about 4.0 to about 6.5. In another embodiment, the pharmaceutical composition of the disclosure comprises about 20 mg/mL to about 30 mg/mL of retifanlimab, about 9 mM to about 11 mM acetate, 76 mg/mL to about 104 mg/mL of sucrose, about 0.08 mg/mL to about 0.53 mg/mL of PS80, and water, wherein the composition has a pH of about 4.5 to about 5.7. In another embodiment, the pharmaceutical composition of the disclosure comprises about 22.5 mg/mL to about 27.5 of retifanlimab, about 9 mM to about 11 mM acetate, about 80 mg/mL to about 100 mg/mL of sucrose, about 0.08 mg/mL to about 0.15 mg/mL of PS80, and water, wherein the composition has a pH of about 4.5 to about 5.7. In another embodiment, the pharmaceutical composition of the disclosure comprises about 25 mg/mL of retifanlimab, about 10 mM acetate, 90 mg/mL of sucrose, about 0.1 mg/mL of PS80, and water, wherein the composition has a pH of about 5.1. In another embodiment, the pharmaceutical composition of the disclosure comprises about 25 mg/mL of retifanlimab, about 10 mM acetate, 90 mg/mL of sucrose, about 0.1 mg/mL of PS80, and water, wherein the composition has a pH of about 4.8 to about 5.4.

In one embodiment, the pharmaceutical composition of the disclosure comprises about 10 mg/mL to about 100 mg/mL of retifanlimab, about 0.05 mg/mL to about 0.35 mg/mL of glacial acetic acid, about 0.80 mg/mL to about 2.0 mg/mL of sodium acetate trihydrate, about 50 mg/mL to about 130 mg/mL of sucrose, about 0.02 mg/mL to about 0.6 mg/mL of PS80, and water, wherein the composition has a pH of about 4.0 to about 6.5. In another embodiment, the pharmaceutical composition of the disclosure comprises about 10 mg/mL to about 100 mg/mL of retifanlimab, about 0.1 mg/mL to about 0.3 mg/mL of glacial acetic acid, about 0.80 mg/mL to about 2.0 mg/mL of sodium acetate trihydrate, about 50 mg/mL to about 130 mg/mL of sucrose, about 0.05 mg/mL to about 0.6 mg/mL of PS80, and water, wherein the composition has a pH of about 4.0 to about 6.5. In another embodiment, the pharmaceutical composition of the disclosure comprises about 20 mg/mL to about 30 mg/mL of retifanlimab, about 0.16 mg/mL to about 0.20 mg/mL of glacial acetic acid, about 0.86 mg/mL to about 1.1 mg/mL of sodium acetate trihydrate, about 76 mg/mL to about 104 mg/mL of sucrose, about 0.08 mg/mL to about 0.53 mg/mL of PS80, and water, wherein the composition has a pH of about 4.5 to about 5.7. In one embodiment, the pharmaceutical composition of the disclosure comprises about 22.5 mg/mL to about 27.5 mg/mL of retifanlimab, about 0.16 mg/mL to about 0.20 mg/mL of glacial acetic acid, about 0.86 mg/mL to about 1.1 mg/mL of sodium acetate trihydrate, 76 mg/mL to about 104 mg/mL of sucrose, about 0.08 mg/mL to about 0.53 mg/mL of PS80, and water, wherein the composition has a pH of about 4.5 to about 5.7. In another embodiment, the pharmaceutical composition of the disclosure comprises about 22.5 mg/mL to about 27.5 mg/mL of retifanlimab, about 0.16 mg/mL to about 0.20 mg/mL of glacial acetic acid, about 0.86 mg/mL to about 1.1 mg/mL of sodium acetate trihydrate, about 80 mg/mL to about 100 mg/mL of sucrose, about 0.08 mg/mL to about 0.15 mg/mL of PS80, and water, wherein the composition has a pH of about 4.5 to about 5.7. In another embodiment, the pharmaceutical composition of the disclosure comprises about 25 mg/mL of retifanlimab, about 0.18 mg/mL glacial acetic acid, about 0.95 mg/mL sodium acetate trihydrate, about 90 mg/mL sucrose, about 0.1 mg/mL PS80, and water, wherein the composition has a pH of about 5.1. In another embodiment, the pharmaceutical composition of the disclosure comprises about 25 mg/mL of retifanlimab, about 10 mM acetate, 90 mg/mL of sucrose, about 0.1 mg/mL of PS80, and water, wherein the composition has a pH of about 4.8 to about 5.4.

In one embodiment, about 10 mL of the pharmaceutical composition of the disclosure comprises about 250 mg of retifanlimab, about 1.8 mg of glacial acetic acid, about 9.5 mg of sodium acetate trihydrate, about 900 mg of sucrose, about 1 mg of PS80, and water, and wherein the composition has a pH of about 5.1. In another embodiment, about 10 mL of the pharmaceutical composition of the disclosure comprises about 250 mg of retifanlimab, about 1.8 mg of glacial acetic acid, about 9.5 mg of sodium acetate trihydrate, about 900 mg of sucrose, about 1 mg of PS80, and water, and wherein the composition has a pH of about 4.8 to about 5.4.

In another embodiment, about 15 mL of the pharmaceutical composition of the disclosure comprises about 375 mg of retifanlimab, about 2.7 mg of glacial acetic acid, about 14.25 mg of sodium acetate trihydrate, about 1350 mg of sucrose, about 1.5 mg of PS80, and water, and wherein the composition has a pH of about 5.1. In another embodiment, about 15 mL of the pharmaceutical composition of the disclosure comprises about 375 mg of retifanlimab, about 2.7 mg of glacial acetic acid, about 14.25 mg of sodium acetate trihydrate, about 1350 mg of sucrose, about 1.5 mg of PS80, and water, and wherein the composition has a pH of about 4.8 to about 5.4.

In another embodiment, about 20 mL of the pharmaceutical composition of the disclosure comprises about 500 mg of retifanlimab, about 3.6 mg of glacial acetic acid, about 19 mg of sodium acetate trihydrate, about 1800 mg of sucrose, about 2 mg of PS80, and water, and wherein the composition has a pH of about 5.1. In another embodiment, about 20 mL of the pharmaceutical composition of the disclosure comprises about 500 mg of retifanlimab, about 3.6 mg of glacial acetic acid, about 19 mg of sodium acetate trihydrate, about 1800 mg of sucrose, about 2 mg of PS80, and water, and wherein the composition has a pH of about 4.8 to about 5.4.

In one embodiment, the pharmaceutical composition of the disclosure has an osmolality of about 200 to about 400 mOsm/kg $H_2O$ In another embodiment, the pharmaceutical composition of the disclosure has an osmolality of about 225 to about 400 mOsm/kg $H_2O$. In another embodiment, the pharmaceutical composition of the disclosure has an osmolality of about 250 to about 375 mOsm/kg. In another embodiment, the pharmaceutical composition of the disclosure has an osmolality of about 250 to about 355 mOsm/kg $H_2O$. In another embodiment, the pharmaceutical composition of the disclosure has an osmolality of about 260 to about 340 mOsm/kg $H_2O$.

In certain embodiments, the pharmaceutical composition of the disclosure is sterile. In one embodiment, the pharmaceutical composition of the disclosure is nonpyrogenic. The disclosure further provides an embodiment of such pharmaceutical compositions, sealed packages or kits wherein the water is sterile, nonpyrogenic, distilled water. In another embodiment, the water in the sealed packages, kits or pharmaceutical composition of the disclosure is Water for Injection, USP, or the equivalent.

In one embodiment, the pharmaceutical composition of the disclosure is stable for at least about 3 months at about 25° C. In another embodiment, the pharmaceutical composition of the disclosure maintains monomeric purity of retifanlimab for at least about 3 months at about 25° C. In another embodiment, the loss of monomeric purity of retifanlimab in the pharmaceutical composition of the disclosure is about 5% or less over about 3 months at about 25° C. In another embodiment, the loss of monomeric purity of retifanlimab in the pharmaceutical composition of the disclosure is about 3% or less over about 3 months at about 25° C. In another embodiment, the pharmaceutical composition of the disclosure maintains the charge heterogeneity profile of retifanlimab for at least about 3 months at about 25° C. In another embodiment, the decrease in the main charge peak (MCP) of retifanlimab in the pharmaceutical composition of the disclosure is about 20% or less over about 3 months at about 25° C. In another embodiment, the increase in the AV of retifanlimab in the pharmaceutical composition of the disclosure is about 20% or less over about 3 months at about 25° C.

In one embodiment, the pharmaceutical composition of the disclosure is stable for at least about 6 months at about 25° C. In another embodiment, the pharmaceutical composition of the disclosure maintains monomeric purity of retifanlimab for at least about 6 months at about 25° C. In another embodiment, the loss of monomeric purity of retifanlimab in the pharmaceutical composition of the disclosure is about 5% or less over about 6 months at about 25° C. In another embodiment, the loss of monomeric purity of retifanlimab in the pharmaceutical composition of the disclosure is about 3% or less over about 6 months at about 25° C. In another embodiment, the pharmaceutical composition of the disclosure maintains the charge heterogeneity profile of retifanlimab for at least about 6 months at about 25° C. In another embodiment, the decrease in the MCP of retifanlimab in the pharmaceutical composition of the disclosure is about 20% or less over about 6 months at about 25° C. In another embodiment, the increase in the AV of retifanlimab in the pharmaceutical composition of the disclosure is about 20% or less over about 6 months at about 25° C.

In one embodiment, pharmaceutical composition of the disclosure is stable for at least about 18 months at about 2° C. to about 8° C. In another embodiment the pharmaceutical composition of the disclosure maintains monomeric purity of retifanlimab for at least about 18 months at about 2° C. to about 8° C. In another embodiment, the loss of monomeric purity of retifanlimab in the pharmaceutical composition of the disclosure is about 5% or less over about 18 months at about 2° C. to about 8° C. In another embodiment, the loss of monomeric purity of retifanlimab in the pharmaceutical composition of the disclosure is about 4% or less over about 18 months at about 2° C. to about 8° C. In another embodiment, the loss of monomeric purity of retifanlimab in the pharmaceutical composition of the disclosure is about 3% or less over about 18 months at about 2° C. to about 8° C. In another embodiment the pharmaceutical composition of the disclosure maintains the charge heterogeneity profile of retifanlimab for at least about 18 months at about 2° C. to about 8° C. In another embodiment, the decrease in the MCP of retifanlimab in the pharmaceutical composition of the disclosure is about 7% or less over about 18 months at about 2° C. to about 8° C. In another embodiment, the decrease in the MCP of retifanlimab in a pharmaceutical composition of the disclosure or in a dosing solution of the disclosure is about 6% or less over about 18 months at about 2° C. to about 8° C. In another embodiment, the decrease in the MCP of retifanlimab in a pharmaceutical composition of the disclosure or in a dosing solution of the disclosure is about 5% or less over about 18 months at about 2° C. to about 8° C. In another embodiment, the increase in the AV of retifanlimab in the pharmaceutical composition of the disclosure is about 7% or less over about 18 months at about 2° C. to about 8° C. In another embodiment, the increase in the AV of retifanlimab in the pharmaceutical composition of the disclosure is about 6% or less over about 18 months at about 2° C. to about 8° C. In another embodiment, the increase in the AV of retifanlimab in the pharmaceutical composition of the disclosure is about 5% or less over about 18 months at about 2° C. to about 8° C.

In one embodiment, pharmaceutical composition of the disclosure is stable for about 24 months at about 2° C. to about 8° C. In another embodiment the pharmaceutical composition of the disclosure maintains monomeric purity of retifanlimab for about 24 months at about 2° C. to about 8° C. In another embodiment, the loss of monomeric purity of retifanlimab in the pharmaceutical composition of the disclosure is about 5% or less over about 24 months at about 2° C. to about 8° C. In another embodiment, the loss of monomeric purity of retifanlimab in the pharmaceutical composition of the disclosure is about 4% or less over about 24 months at about 2° C. to about 8° C. In another embodiment, the loss of monomeric purity of retifanlimab in the pharmaceutical composition of the disclosure is about 3% or less over about 24 months at about 2° C. to about 8° C. In another embodiment the pharmaceutical composition of the disclosure maintains the charge heterogeneity profile of retifanlimab for at least about 24 months at about 2° C. to about 8° C. In another embodiment, the decrease in the MCP of retifanlimab in the pharmaceutical composition of the disclosure is about 7% or less over about 24 months at about 2° C. to about 8° C. In another embodiment, the decrease in the MCP of retifanlimab in the pharmaceutical composition of the disclosure is about 6% or less over about 24 months at about 2° C. to about 8° C. In another embodiment, the decrease in the MCP of retifanlimab in the pharmaceutical composition of the disclosure is about 5% or less over about 24 months at about 2° C. to about 8° C. In another embodiment, the increase in the AV of retifanlimab in the pharmaceutical composition of the disclosure is about 7% or less over about 24 months at about 2° C. to about 8° C. In another embodiment, the increase in the AV of retifanlimab in the pharmaceutical composition of the disclosure is about 6% or less over about 24 months at about 2° C. to about 8° C. In another embodiment, the increase in the AV of retifanlimab in the pharmaceutical composition of the disclosure is about 5% or less over about 24 months at about 2° C. to about 8° C.

In one embodiment, pharmaceutical composition of the disclosure is stable for about 36 months at about 2° C. to about 8° C. In another embodiment the pharmaceutical composition of the disclosure maintains monomeric purity of retifanlimab for about 36 months at about 2° C. to about 8° C. In another embodiment, the loss of monomeric purity of retifanlimab in the pharmaceutical composition of the disclosure is about 5% or less over about 36 months at about 2° C. to about 8° C. In another embodiment, the loss of monomeric purity of retifanlimab in the pharmaceutical composition of the disclosure is about 4% or less over about 36 months at about 2° C. to about 8° C. In another embodiment, the loss of monomeric purity of retifanlimab in the pharmaceutical composition of the disclosure is about 3% or less over about 36 months at about 2° C. to about 8° C. In another embodiment the pharmaceutical composition of the disclosure maintains the charge heterogeneity profile of retifanlimab for at least about 36 months at about 2° C. to about 8° C. In another embodiment, the decrease in the MCP of retifanlimab in the pharmaceutical composition of the disclosure is about 7% or less over about 36 months at about 2° C. to about 8° C. In another embodiment, the decrease in the MCP of retifanlimab in the pharmaceutical composition of the disclosure is about 6% or less over about 36 months at about 2° C. to about 8° C. In another embodiment, the decrease in the MCP of retifanlimab in the pharmaceutical composition of the disclosure is about 5% or less over about 36 months at about 2° C. to about 8° C. In another embodiment, the increase in the AV of retifanlimab in the pharmaceutical composition of the disclosure is about 7% or less over about 36 months at about 2° C. to about 8° C. In another embodiment, the increase in the AV of retifanlimab in the pharmaceutical composition of the disclosure is about 6% or less over about 36 months at about 2° C. to about 8° C. In another embodiment, the increase in the AV of retifanlimab in the pharmaceutical composition of the disclosure is about 5% or less over about 36 months at about 2° C. to about 8° C.

In one embodiment, pharmaceutical composition of the disclosure is stable for about 48 months at about 2° C. to about 8° C. In another embodiment the pharmaceutical composition of the disclosure maintains monomeric purity of retifanlimab for about 48 months at about 2° C. to about 8° C. In another embodiment, the loss of monomeric purity of retifanlimab in the pharmaceutical composition of the disclosure is about 5% or less over about 48 months at about 2° C. to about 8° C. In another embodiment, the loss of monomeric purity of retifanlimab in the pharmaceutical composition of the disclosure is about 4% or less over about 48 months at about 2° C. to about 8° C. In another embodiment, the loss of monomeric purity of retifanlimab in the pharmaceutical composition of the disclosure is about 3% or less over about 48 months at about 2° C. to about 8° C. In another embodiment, the decrease in the MCP of retifanlimab in the pharmaceutical composition of the disclosure is about 7% or less over about 48 months at about 2° C. to about 8° C. In another embodiment, the decrease in the MCP of retifanlimab in the pharmaceutical composition of the disclosure is about 6% or less over about 48 months at about 2° C. to about 8° C. In another embodiment, the decrease in the MCP of retifanlimab in the pharmaceutical composition of the disclosure is about 5% or less over about 48 months at about 2° C. to about 8° C. In another embodiment, the increase in the AV of retifanlimab in the pharmaceutical composition of the disclosure is about 7% or less over about 48 months at about 2° C. to about 8° C. In another embodiment, the increase in the AV of retifanlimab in the pharmaceutical composition of the disclosure is about 6% or less over about 48 months at about 2° C. to about 8° C. In another embodiment, the increase in the AV of retifanlimab in the pharmaceutical composition of the disclosure is about 5% or less over about 48 months at about 2° C. to about 8° C.

In one embodiment, pharmaceutical composition of the disclosure is stable for about 60 months at about 2° C. to about 8° C. In another embodiment the pharmaceutical composition of the disclosure maintains monomeric purity of retifanlimab for about 60 months at about 2° C. to about 8° C. In another embodiment, the loss of monomeric purity of retifanlimab in the pharmaceutical composition of the disclosure is about 5% or less over about 60 months at about 2° C. to about 8° C. In another embodiment, the loss of monomeric purity of retifanlimab in the pharmaceutical composition of the disclosure is about 4% or less over about 60 months at about 2° C. to about 8° C. In another embodiment, the loss of monomeric purity of retifanlimab in the pharmaceutical composition of the disclosure is about 3% or less over about 60 months at about 2° C. to about 8° C. In another embodiment, the decrease in the MCP of retifanlimab in the pharmaceutical composition of the disclosure is about 7% or less over about 60 months at about 2° C. to about 8° C. In another embodiment, the decrease in the MCP of retifanlimab in the pharmaceutical composition of the disclosure is about 6% or less over about 60 months at about 2° C. to about 8° C. In another embodiment, the decrease in the MCP of retifanlimab in the pharmaceutical composition of the disclosure is about 5% or less over about 60 months at about 2° C. to about 8° C. In another embodiment, the increase in the AV of retifanlimab in the pharmaceutical composition of the disclosure is about 7% or less over about 60 months at about 2° C. to about 8° C. In another embodiment, the increase in the AV of retifanlimab in the pharmaceutical composition of the disclosure is about 6% or less over about 60 months at about 2° C. to about 8° C. In another embodiment, the increase in the AV of retifanlimab in the pharmaceutical composition of the disclosure is about 5% or less over about 60 months at about 2° C. to about 8° C.

The disclosure also provides containers comprising a pharmaceutical composition of the disclosure. The disclosure further provides pharmaceutical packs or kits comprising one or more containers containing a pharmaceutical composition of the disclosure. In one embodiment, such container is a vial (e.g., a single-dose vial). In one embodiment, such pharmaceutical pack or kit of the disclosure contains a vial (e.g., single-dose vial). In another embodiment, such pharmaceutical pack or kit of the disclosure contains more than one vial. In another embodiment, such vials contain about 10 mL of a pharmaceutical composition of the disclosure comprising about 250 mg of retifanlimab such that the concentration of retifanlimab is about 25 mg/mL per vial. In another embodiment, such vials contain about 15 mL of a pharmaceutical composition of the disclosure comprising about 375 mg of retifanlimab such that the concentration of retifanlimab is about 25 mg/mL per vial. In another embodiment, such vials contain about 20 mL of a pharmaceutical composition of the disclosure comprising about 500 mg of retifanlimab such that the concentration of retifanlimab is about 25 mg/mL per vial. It will be appreciated that such vials may comprise an overfill volume of such pharmaceutical composition of the disclosure to ensure sufficient volume for withdrawal of 10 mL (250 mg), 15 mL (375 mg), and 20 mL (500 mg) of retifanlimab for dose delivery.

Additionally, one or more other prophylactic or therapeutic agents useful for the treatment of a disease can also be included in the pharmaceutical pack or kit of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration. Optionally associated with such container(s) is a product label describing the indication(s) and/or instructions for preparation and administration of a dosing solution comprising the retifanlimab composition.

The present disclosure provides kits that comprise a pharmaceutical composition of the disclosure that can be used in the methods of the disclosure. In such kits, the pharmaceutical composition of the disclosure is generally packaged in hermetically sealed containers, such as ampoules, vials, sachets, or other suitable containers, for example that can indicate the quantity of the component(s) contained therein. The container can be formed of any pharmaceutically acceptable material, such as glass, resin, plastic or other suitable material. In one embodiment, the container is borosilicate glass vial. In another embodiment, the container is single-dose 10 mL USP Type I borosilicate glass vial. In another embodiment, the 10 mL container contains about 250 mg retifanlimab in a 10 mL volume. In another embodiment, the container is single-dose 20 mL USP Type I borosilicate glass vial. In another embodiment, the 20 mL container contains about 375 mg retifanlimab in a 15 mL volume. In another embodiment, the 20 mL container contains about 500 mg retifanlimab in a 20 mL volume. In one embodiment, the container is aseptically filled. In one embodiment, the pharmaceutical compositions of the disclosure comprising such kits are supplied as a liquid solutions. Such liquid solutions can be stored at between about 2° C. and about 8° C. in the original containers until ready to be administered. However, such solutions can be stored at room temperature (~25° C.) for short periods of time. In one embodiment, such pharmaceutical compositions have a shelf-life of at least about 18 months at about 2° C. to about 8° C. In one embodiment, such pharmaceutical compositions have a shelf-life of at least about 24 months at about 2° C. to about 8° C. In one embodiment, such pharmaceutical compositions have a shelf-life of about 36 months at about 2° C. to about 8° C. In one embodiment, such pharmaceutical compositions of the disclosure have a shelf-life of at least about 48 months at about 2° C. to about 8° C. In one embodiment, such pharmaceutical compositions of the disclosure have a shelf-life of at least about 60 months at about 2° C. to about 8° C. In other embodiments, such pharmaceutical compositions of the disclosure have a shelf-life of at least about 3 months at about 25° C. In other embodiments, such pharmaceutical compositions of the disclosure have a shelf-life of at least about 6 months at about 25° C. The kit can further comprise one or more other prophylactic and/or therapeutic agents useful for the treatment of cancer, in one or more containers; and/or the kit can further comprise one or more antibodies, for example cytotoxic antibodies, that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

In one embodiment, a kit of the disclosure comprises:
a) a container comprising a pharmaceutical composition, the composition comprising about 10 mg/mL to about 100 mg/mL of retifanlimab, about 5 mM to about 30 mM acetate, about 50 mg/mL to about 130 mg/mL of sucrose, about 0.02 mg/mL to about 0.6 mg/mL of PS80, and water, wherein the composition has a pH of about 4.0 to about 6.5; and optionally
b) instructions for administration of the pharmaceutical composition to a subject in need thereof.

In one embodiment, a kit of the instant disclosure comprises:
a) a container comprising a pharmaceutical composition, the composition comprising about 10 mg/mL to about 100 mg/mL of retifanlimab, about 7.5 mM to about 20 mM acetate, about 50 mg/mL to about 130 mg/mL of sucrose, about 0.05 mg/mL to about 0.6 mg/mL of PS80, and water, wherein the composition has a pH of about 4.0 to about 6.5; and optionally
b) instructions for administration of the pharmaceutical composition to a subject in need thereof.

In one embodiment, a kit of the instant disclosure comprises:
a) a container comprising a pharmaceutical composition, the composition comprising about 20 mg/mL to about 30 mg/mL of retifanlimab, about 9 mM to about 11 mM acetate, 76 mg/mL to about 104 mg/mL of sucrose, about 0.08 mg/mL to about 0.53 mg/mL of PS80, and water, wherein the composition has a pH of about 4.5 to about 5.7; and optionally
b) instructions for administration of the pharmaceutical composition to a subject in need thereof.

In one embodiment, such container can comprise about 25 mg/mL of retifanlimab, about 10 mM acetate, 90 mg/mL of sucrose, about 0.1 mg/mL of PS80, and water, wherein the composition has a pH of about 5.1. In another embodiment, such container can comprise about 25 mg/mL of retifanlimab, about 10 mM acetate, 90 mg/mL of sucrose, about 0.1 mg/mL of PS80, and water, wherein the composition has a pH of 4.8 to 5.4.

In one embodiment, a kit of the instant disclosure comprises:
  a) a container comprising a pharmaceutical composition, the composition comprising about 10 mg/mL to about 100 mg/mL of retifanlimab, about 0.05 mg/mL to about 0.35 mg/mL of glacial acetic acid, about 0.80 mg/mL to about 2.0 mg/mL of sodium acetate trihydrate, about 50 mg/mL to about 130 mg/mL of sucrose, about 0.02 mg/mL to about 0.6 mg/mL of PS80, and water, wherein the composition has a pH of about 4.0 to about 6.5; and optionally
  b) instructions for administration of the pharmaceutical composition to a subject in need thereof.

In one embodiment, a kit of the instant disclosure comprises:
  a) a container comprising a pharmaceutical composition, the composition comprising about 10 mg/mL to about 100 mg/mL of retifanlimab, about 0.1 mg/mL to about 0.3 mg/mL of glacial acetic acid, about 0.80 mg/mL to about 2.0 mg/mL of sodium acetate trihydrate, about 50 mg/mL to about 130 mg/mL of sucrose, about 0.05 mg/mL to about 0.6 mg/mL of PS80, and water, wherein the composition has a pH of about 4.0 to about 6.5; and optionally
  b) instructions for administration of the pharmaceutical composition to a subject in need thereof.

In one embodiment, a kit of the instant disclosure comprises:
  a) a container comprising a pharmaceutical composition, the composition comprising about 20 mg/mL to about 30 mg/mL of retifanlimab, about 0.16 mg/mL to about 0.20 mg/mL of glacial acetic acid, about 0.86 mg/mL to about 1.1 mg/mL of sodium acetate trihydrate, 76 mg/mL to about 104 mg/mL of sucrose, about 0.08 mg/mL to about 0.53 mg/mL of PS80, and water, wherein the composition has a pH of about 4.5 to about 5.7; and optionally
  b) instructions for administration of the pharmaceutical composition to a subject in need thereof.

In one embodiment, a kit of the disclosure comprises:
  a) a container comprising a pharmaceutical composition, the composition comprising about 22.5 mg/mL to about 27.5 mg/mL of retifanlimab, about 0.16 mg/mL to about 0.20 mg/mL of glacial acetic acid, about 0.86 mg/mL to about 1.1 mg/mL of sodium acetate trihydrate, 76 mg/mL to about 104 mg/mL of sucrose, about 0.08 mg/mL to about 0.53 mg/mL of PS80, and water, wherein the composition has a pH of about 4.5 to about 5.7; and optionally
  b) instructions for administration of the pharmaceutical composition to a subject in need thereof.

In one embodiment, such container can comprise about 25 mg/mL of retifanlimab, about 0.18 mg/mL glacial acetic acid, about 0.95 mg/mL sodium acetate trihydrate, about 90 mg/mL sucrose, about 0.1 mg/mL PS80, and water, wherein the composition has a pH of about 5.1. In another embodiment, such container can comprise about 25 mg/mL of retifanlimab, about 0.18 mg/mL glacial acetic acid, about 0.95 mg/mL sodium acetate trihydrate, about 90 mg/mL sucrose, about 0.1 mg/mL PS80, and water, wherein the composition has a pH of 4.8 to 5.4.

The water in such compositions, containers, and kits of the disclosure can be sterile, nonpyrogenic, distilled water, and can be Water for Injection, USP, or the equivalent.

In one embodiment, pharmaceutical kits of the disclosure can include instructional material. The included instructional material of the pharmaceutical kits of the disclosure may instruct that the provided pharmaceutical composition is to be administered in combination with an additional agent which can be provided in the same pharmaceutical kit or in a separate pharmaceutical kit. Such instructional material may instruct that the provided pharmaceutical composition is to be administered once about every 2 weeks, once about every 3 weeks, once about every 4 weeks, or more or less often at regular or irregular intervals. Such instructional material may instruct that a provided container of pharmaceutical composition comprises about 25 mg/mL (e.g., 250 mg/10 mL; 375 mg/15 mL; or 500 mg/20 mL) of retifanlimab. Such instructional material may instruct that the provided pharmaceutical composition is to be administered at a weight-based treatment dose of about 3 mg/kg to about 10 mg/kg, about 3 mg/kg, or about 10 mg/kg or at a flat dose of about 375 mg, about 500 mg, or about 750 mg. Such instructional material may instruct that the provided pharmaceutical composition is to be diluted (e.g., in 0.9% sodium chloride or D5W) prior to administration. The included instructional material of the pharmaceutical kits of the disclosure may combine any set of such information (e.g., it may instruct that a retifanlimab pharmaceutical composition is to be diluted in 0.9% sodium chloride or D5W and administered at a weight-based treatment dose of about 3 mg/kg, or about 10 mg/kg or at a flat dose of about 375 mg, about 500 mg, or about 750 mg, and that such dose is to be administered once about every 2 weeks; once about every 3 weeks; about every 4 weeks, or more or less often at regular or irregular intervals). Such instructional material may instruct regarding the mode of administration of the provided pharmaceutical composition, for example that it is to be administered by intravenous (IV) infusion. The included instructional material of the pharmaceutical kits of the disclosure may instruct regarding the duration or timing of such administration, for example that the provided pharmaceutical composition is to be administered by intravenous (IV) infusion over about 30 minutes, or over about 60 minutes, or for longer or shorter durations.

In one embodiment, the instructional material of the pharmaceutical kits of the disclosure instructs that the provided pharmaceutical composition is diluted in 0.9% sodium chloride to obtain a dosing solution. In another embodiment, the instructional material of the pharmaceutical kits of the disclosure instructs that the provided pharmaceutical composition is diluted in D5W to obtain a dosing solution.

In one embodiment, the instructional material of the pharmaceutical kits of the disclosure provides a method of administering a pharmaceutical composition of the disclosure to a subject in need thereof, wherein in the method comprises:
  a) diluting the pharmaceutical composition in a container in 0.9% sodium chloride to obtain a dosing solution;
  b) inverting the container to mix the diluted solution; and
  c) attaching the container containing the dosing solution to a device for administration to the subject.

In one embodiment, the instructional material of the pharmaceutical kits of the disclosure provides a method of administering a pharmaceutical composition of the disclosure to a subject in need thereof, wherein in the method comprises:
  a) diluting the pharmaceutical composition in a container in D5W to obtain a dosing solution;
  b) inverting the container to mix the diluted solution; and
  c) attaching the container containing the dosing solution to a device for administration to the subject.

In one embodiment, the container is an IV bag containing 0.9% sodium chloride. In another embodiment, the container is an IV bag containing D5W.

In one embodiment, the administration of the dosing solution is by intravenous (IV) infusion over a period of about 30 minutes to about 120 minutes, about 30 minutes or about 60 minutes.

In one embodiment, the pharmaceutical composition of the disclosure is diluted to obtain a weight-based treatment dose of about 3 mg/kg of retifanlimab in the dosing solution. In another embodiment, the pharmaceutical composition of the disclosure is diluted to obtain a weight-based treatment dose of about 10 mg/kg of retifanlimab in the dosing solution.

In one embodiment, the pharmaceutical composition of the disclosure is diluted to obtain a flat dose of about 375 mg of retifanlimab in the dosing solution. In another embodiment, the pharmaceutical composition of the disclosure is diluted to obtain a flat dose of about 500 mg of retifanlimab in the dosing solution. In another embodiment, the pharmaceutical composition of the disclosure is diluted to obtain a flat dose of about 750 mg of retifanlimab in the dosing solution.

The included instructional material of the pharmaceutical kits of the disclosure may instruct regarding the appropriate or desired use of the included pharmaceutical composition, for example instructing that the provided pharmaceutical composition is to be administered for the treatment of cancer, for example in a prophylactically effective amount or therapeutically effective amount. Such cancer is selected from the group consisting of: adrenal gland cancer, AIDS-associated cancer, alveolar soft part sarcoma, anal cancer (including squamous cell carcinoma of the anal canal (SCAC)), bladder cancer, bone cancer, brain and spinal cord cancer, breast cancer (including, HER2+ breast cancer or Triple-Negative Breast Cancer (TNBC)), carotid body tumor, cervical cancer (including, HPV-related cervical cancer), chondrosarcoma, chordoma, chromophobe renal cell carcinoma, clear cell carcinoma, colon cancer, colorectal cancer, desmoplastic small round cell tumor, ependymoma, endometrial cancer (including, unselected endometrial cancer, MSI-high endometrial cancer, dMMR endometrial cancer, and/or DNA polymerase ε (POLE) exonuclease domain mutation positive endometrial cancer), Ewing's sarcoma, extraskeletal myxoid chondrosarcoma, gallbladder or bile duct cancer (including, cholangiocarcinoma bile duct cancer), gastric cancer, gastroesophageal junction (GEJ) cancer, gestational trophoblastic disease, germ cell tumor, glioma, glioblastoma, head and neck cancer (including, squamous cell carcinoma of head and neck (SCCHN)), a hematological malignancy, a hepatocellular carcinoma, islet cell tumor, Kaposi's Sarcoma, kidney cancer (including, renal cell carcinomas (RCC), clear cell RRC, papillary RCC and chromophobe RCC), leukemia (including, acute myeloid leukemia), liposarcoma/malignant lipomatous tumor, liver cancer (including, hepatocellular carcinoma liver cancer (HCC)), lymphoma (including, diffuse large B-cell lymphoma (DLBCL), non-Hodgkin's lymphoma (NHL)), lung cancer (including, small cell lung cancer (SCLC), non-small cell lung cancer (NSCLC)), medulloblastoma, melanoma (including, uveal melanoma), meningioma, mesothelioma (including, mesothelial pharyngeal cancer), multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pharyngeal cancer, pheochromocytoma, pituitary tumor, prostate cancer (including, metastatic castration resistant prostate cancer (mCRPC)), posterious uveal melanoma, renal metastatic cancer, rhabdoid tumor, rhabdomyosarcoma, sarcoma, skin cancer (including Merkel cell carcinoma), a small round blue cell tumor of childhood (including neuroblastoma and rhabdomyosarcoma), soft-tissue sarcoma, squamous cell cancer, stomach cancer, synovial sarcoma, testicular cancer, thymic carcinoma, thymoma, thyroid cancer, urothelial cancer, and uterine cancer.

The included instructional material of the pharmaceutical kits of the disclosure may instruct that such pharmaceutical composition is to be administered for a cancer selected from the group consisting of: anal cancer, breast cancer, cervical cancer, chromophobe renal cell carcinoma, colorectal cancer, endometrial cancer, gastric cancer, GEJ cancer, glioma, head and neck cancer, kidney cancer, liver cancer, lung cancer, lymphoma, melanoma, multiple myeloma, renal metastatic cancer, ovarian cancer, pancreatic cancer, prostate cancer, skin cancer, urothelial cancer, and a uterine cancer.

In one embodiment, included instructional material of the pharmaceutical kits of the disclosure instructs that such pharmaceutical composition is to be administered for the treatment of anal cancer. In another embodiment, the anal cancer is SCAC.

In one embodiment, included instructional material of the pharmaceutical kits of the disclosure instructs that such pharmaceutical composition is to be administered for the treatment of lung cancer. In another embodiment, the lung cancer is NSCLC.

In one embodiment, included instructional material of the pharmaceutical kits of the disclosure instructs that such pharmaceutical composition is to be administered for the treatment of endometrial cancer. In another embodiment, the endometrial cancer is MSI-high endometrial cancer, dMMR endometrial cancer, and/or POLE exonuclease domain mutation positive endometrial cancer.

In one embodiment, included instructional material of the pharmaceutical kits of the disclosure instructs that such pharmaceutical composition is to be administered for the treatment of skin cancer. In another embodiment, the skin cancer is Merkel cell carcinoma.

In one embodiment, included instructional material of the pharmaceutical kits of the disclosure instructs that such pharmaceutical composition is to be administered for the treatment of head and neck cancer. In another embodiment, the head and neck cancer is SCCHN.

In one embodiment, included instructional material of the pharmaceutical kits of the disclosure instructs that such pharmaceutical composition is to be administered for the treatment of prostate cancer. In another embodiment, the prostate cancer is mCRPC.

In one embodiment, included instructional material of the pharmaceutical kits of the disclosure instructs that such pharmaceutical composition is to be administered for the treatment of kidney cancer. In another embodiment, the kidney cancer is an RCC. In another embodiment, the kidney cancer is a clear cell RCC.

In one embodiment, included instructional material of the pharmaceutical kits of the disclosure instructs that such pharmaceutical composition is to be administered for the treatment of melanoma.

In one embodiment, included instructional material of the pharmaceutical kits of the disclosure instructs that such pharmaceutical composition is to be administered for treatment of urothelial cancer.

In one embodiment, included instructional material of the pharmaceutical kits of the disclosure instructs that such pharmaceutical composition is to be administered for the treatment of squamous cell cancer.

In one embodiment, included instructional material of the pharmaceutical kits of the disclosure instructs that such pharmaceutical composition is to be administered for the treatment of glioma.

In one embodiment, included instructional material of the pharmaceutical kits of the disclosure instructs that such pharmaceutical composition is to be administered for the treatment of cervical cancer.

In one embodiment, included instructional material of the pharmaceutical kits of the disclosure instructs that such pharmaceutical composition is to be administered for the treatment of kidney cancer.

In one embodiment, included instructional material of the pharmaceutical kits of the disclosure instructs that such pharmaceutical composition is to be administered for the treatment of a chromophobe renal cell carcinoma In one embodiment, included instructional material of the pharmaceutical kits of the disclosure instructs that such pharmaceutical composition is to be administered for the treatment of a renal metastatic cancer.

In one embodiment, included instructional material of the pharmaceutical kits of the disclosure instructs that such pharmaceutical composition is to be administered for the treatment of uterine cancer.

The included instructional material of the pharmaceutical kits of the disclosure may instruct that the pharmaceutical composition is to be administered for treatment of such cancer wherein such cancer is a metastatic cancer. In some embodiments, the included instructional material of the pharmaceutical kits of the disclosure may instruct that the pharmaceutical composition is to be administered for treatment of such cancer wherein such cancer is a primary cancer.

In some embodiments, the included instructional material of the pharmaceutical kits of the disclosure may instruct that the pharmaceutical composition is to be administered for treatment of such cancer before, during, or after another treatment for such cancer. In certain of such embodiments, such instructional material may instruction that the pharmaceutical composition is to be administered as a neoadjuvant therapy for treatment of such cancer. In other of such embodiments such instructional material may instruction that the pharmaceutical composition is to be administered as an adjuvant therapy for treatment of such cancer. In other of such embodiments such instructional material may instruction that the pharmaceutical composition is to be administered as a component of a combination therapy for treatment of such cancer.

In some embodiments, the included instructional material of the pharmaceutical kits of the disclosure may instruct that the pharmaceutical composition is to be administered for treatment of such cancer expressing PD-L1. The instructional material may further specify a particular PD-L1 expression measurement and score, for example a Tumor Proportion Score (TPS) of ≥1%, or a Combined Positive Score (CPS) of ≥1. The instructional material may further specify that such PD-L1 expression score is determined by a test approved for use by a regulatory agency (e.g., FDA-approved). Such tests have been described, for example FDA-approved tests are listed on the FDA website:fda.gov/CompanionDiagnostics, and include for example PD-L1 IHC 22C3 pharmDx, additional tests are described by Cheung et al., (2019), "Fit-For-Purpose PD-L1 Biomarker Testing For Patient Selection in Immuno-Oncology: Guidelines For Clinical Laboratories From the Canadian Association of Pathologists-Association Canadienne Des Pathologistes (CAP-ACP)." Appl Immunohistochem Mol Morphol 27 (10):699-714.

The pharmaceutical compositions of the disclosure of the present disclosure can be provided for the treatment, prophylaxis, and amelioration of one or more symptoms associated with a disease, disorder or infection by administering to a subject a therapeutically effective amount or prophylactically effective amount of retifanlimab. In one embodiment, such pharmaceutical compositions are substantially purified (i.e., substantially free from substances that limit its effect or produce undesired side effects) as determined by any suitable method. In another embodiment, the subject is an animal, including a mammal such as non-primate (e.g., bovine, equine, feline, canine, rodent, etc.) or a primate (e.g., monkey such as, a cynomolgus monkey, human, etc.). In one embodiment, the subject is a human. The terms "subject" and "patient" are used herein interchangeably.

Methods of administering a pharmaceutical composition (i.e., a retifanlimab composition) of the disclosure include, but are not limited to, parenteral administration (e.g., intravenous). In one embodiment, the pharmaceutical composition (i.e., a retifanlimab composition) of the disclosure is administered intravenously. The pharmaceutical compositions of the disclosure may be administered together with other pharmaceutically active agents, such as chemotherapeutic agents, including but not limited to, antimetabolite chemotherapeutics (including pemetrexed), platinum-based chemotherapeutics (including for example, cisplatin and carboplatin), and taxane-based chemotherapeutics (including for example paclitaxel, and nab-paclitaxel), biologic agents, including but not limited to antibodies, and antibody-like molecules including those that bind a cancer antigen. Such cancer antigens include, but are not limited to, 5T4, B7-H3, CD19, CD20, CD51, CD123, DR5, EGFR, EpCam, GD2, gpA33, HER2, ROR-1, TAG-72, VEGF-A and/or VEGFR2. Numerous antibody and antibody-like molecules that bind to such cancer antigens have been described and include but are not limited to, bevacizumab, cetuximab, enoblituzumab, flotetuzumab, margetuximab, ofatumumab, panitumumab, rituximab, trastuzumab, and others.

In one embodiment, the amount of the pharmaceutical composition (i.e., a retifanlimab composition) of the disclosure is determined using a weight-based dose of retifanlimab. The term "weight-based dose" as used herein, refers to a discrete amount of retifanlimab to be administered per a unit of patient weight, for example milligrams of retifanlimab per kilograms of a subject's body weight (mg/kg body weight, abbreviated herein as "mg/kg"). The calculated dose will be administered based on the subject's body weight at baseline. Typically, a significant (for example at least about a plus or minus 10%) change in body weight from baseline or established plateau weight will prompt recalculation of dose. Single or multiple doses may be given.

In certain embodiments, retifanlimab is administered to a subject in need thereof at a weight-based dose of from about 3 mg/kg to about 10 mg/kg. In certain embodiments, retifanlimab is administered to a subject in need thereof at a dose of about 3 mg/kg or about 10 mg/kg. With respect to weight-based doses, the term "about" is intended to denote a range that is ±10% of a recited dose, such that for example, a dose of about 10 mg/kg will be between 9 mg/kg and 11 mg/kg.

In one embodiment, the amount of the pharmaceutical composition (i.e., a retifanlimab composition) of the disclosure is determined using a flat dose of retifanlimab. The term "flat dose" as used herein, refers to a dose that is independent of the weight of the patient, and includes physically discrete units of retifanlimab that are suited as a unitary dose for the subjects to be treated; for example wherein each unit contains a predetermined quantity of retifanlimab (e.g., calculated to produce a desired therapeutic effect) in association with a pharmaceutical carrier, and optionally, in association with a further agent. Single or multiple flat doses may be given.

Retifanlimab can be administered as a weight-based dose (e.g., a mg/kg patient weight dose) or as a flat dose (e.g., a 375 mg dose). Generally, doses of retifanlimab (and optionally a further pharmaceutically active agent) can be used in order to provide a subject with the retinfanlimab in therapeutically effective amounts or prophylactically effective amounts. As used herein, the term "dose" refers to a specified amount of medication taken at one time. The term "dosage" refers to the administering of a specific amount, and frequency of doses over a specified period of time; the term dosage thus includes chronological features, such as periodicity.

As used herein, "a therapeutically effective amount" of retifanlimab in a pharmaceutical composition of the disclosure when used for the treatment of a cancer is an amount which can slow the progression of the cancer; reduce the number of cancer cells in fluids (e.g., blood, peripheral cells or lymphatic fluids), tissue or organs (cytoxic); allow the number of cancer cells to remain relatively constant (cytostatic); reduce tumor size, inhibit metastasis, inhibit tumor growth and/or ameliorate one or more of the symptoms of the cancer. Therapeutically effective amounts of retifanlimab for use in formulating the pharmaceutical compositions of the disclosure are provide herein and/or can be determined, for example, by a health care professional taking into account certain factors such as the type of cancer treated, the route of delivery, the age, weight, severity of the subject's symptoms and response pattern of the subject. As used herein, a "prophylactically effective amount" of retifanlimab in a pharmaceutical composition of the disclosure when used for the prophylaxis of a cancer is an amount which can prevent or reduce the risk of occurrence or recurrence of the cancer. As used herein, treatment of a cancer with the pharmaceutical compositions, containers, kits or methods of the disclosure, for example, can comprise or can comprise administering a therapeutically effective amount or prophylactically effective amount of retifanlimab to subject in need thereof.

In certain embodiments, retifanlimab is administered to a subject in need thereof at a flat dose of from about 375 mg. In certain embodiments, retifanlimab is administered to a subject in need thereof at a flat dose of about 500 mg. In certain embodiments, retifanlimab is administered to a subject in need thereof at a flat dose of about 750 mg. With respect to flat doses, the term "about" is intended to denote a range that is ±10% of a recited dose, such that for example, a dose of about 500 mg/kg will be between 450 mg and 550 mg.

A dose of the pharmaceutical compositions of the disclosure (i.e., a dose of a retifanlimab composition) can be administered at periodic intervals over a period of time sufficient to encompass at least 2 doses, at least 4 doses, at least 6 doses, at least 12 doses, or at least 24 doses, or more than 24 doses. Such administration of pharmaceutical compositions of the disclosure at periodic intervals over a period of time can be considered a "course of treatment". For example, a dosage can be administered e.g., once every two weeks ("Q2W"), once every three weeks ("Q3W"), once every four weeks ("Q4W"), or for shorter or longer periods of time. Such periodic administration may continue for a period of time e.g., for between about 1 to 52 weeks, or for more than about 52 weeks. Such course of treatment can be divided into increments, each referred to herein as a "cycle," of varying shorter intervals, e.g., between 2 to 8 weeks, during which a set number of doses are administered. The dose and/or the frequency of administration can be the same or different during each cycle. Factors that may influence the dosage and timing required to effectively treat a subject, include, e.g., the severity of the disease or disorder, formulation, route of delivery, previous treatments, the general health and/or age of the subject, and the presence of other diseases in the subject. Moreover, treatment of a subject with a therapeutically effective amount of a compound can include a single treatment or can include a series of treatments.

A "dosing regimen" is a dosage administration in which a patient is administered a predetermined dose (or set of such predetermined doses) at a predetermined frequency (or set of such frequencies) for a predetermined periodicity (or periodicities). One dosing regimen of the disclosure comprises administration of a retifanlimab composition of the disclosure at a dose of about 1 mg/kg administered Q2W. Another dosing regimen of the disclosure comprises administration of a retifanlimab composition of the disclosure at a dose of about 3 mg/kg administered Q2W or Q4W. Another dosing regimen of the disclosure comprises administration of a retifanlimab composition of the disclosure at a dose of about 10 mg/kg administered Q2W or Q4W. Another dosing regimen of the disclosure comprises administration of a retifanlimab composition of the disclosure at a flat dose of about 375 mg administered Q3W. Another dosing regimen of the disclosure comprises administration of a retifanlimab composition of the disclosure at a flat dose of about 500 mg administered Q4W. Another dosing regimen of the disclosure comprises administration of a retifanlimab composition of the disclosure at a flat dose of about 750 mg administered Q4W.

It is specifically contemplated that in certain embodiments of the disclosure, administration of the pharmaceutical composition occurs at a predetermined frequency or periodicity, or within about 1-3 days of such scheduled interval, such that administration occurs 1-3 day before, 1-3 days after, or on the day of a scheduled dose, e.g., once every 3 weeks (±3 days). In such embodiments, the retifanlimab composition of the disclosure can be administered by IV infusion. In certain embodiments, the pharmaceutical compositions of the disclosure are administered IV infusion which can be continuous intravenous infusion, or discontinuous intravenous infusion. In certain embodiments, the retifanlimab composition of the disclosure is administered by IV infusion according to any of the dosing regimens of the disclosure for a duration of at least about 1 month or more, at least about 3 months or more, at least about 4 months or more, at least about 6 months or more, or at least about 12 months or more than about 12 months. A treatment duration of at least about 6 months or more, or for at least about 12 months or more than about 12 months, or until reduction or remission of disease, stable disease, or unmanageable toxicity is observed. In certain embodiments, treatment continues for a period of time after reduction or remission of disease or stable disease is observed. In certain embodiments, treatment can be paused due to illness, adverse event, etc., and is resumed upon resolution, reduction or amelioration of such illness, adverse event, etc.

In certain embodiments of the methods of the disclosure, the pharmaceutical composition (i.e., the retifanlimab composition) is diluted into an infusion bag comprising a suitable diluent, e.g., 0.9% sodium chloride or D5W, for administration by IV infusion. Since infusion or allergic reactions may occur, premedication for the prevention of such infusion reactions can be utilized and precautions for anaphylaxis can be observed during the antibody administration. In one embodiment, the IV infusion is administered to the subject over about 30 minutes to about 120 minutes, about 30 minutes to about 90 minutes, about 30 minutes to about 60 minutes, about 30 minutes, about 60 minutes, or about 120 minutes. In certain embodiments, the IV infusion is administered to the subject over about 30 minutes or about 60 minutes. In other embodiments, the IV infusion is administered to the subject over about 30 minutes.

A dosing solution that comprises a pharmaceutical composition (such as a retifanlimab composition of the disclosure) is suitable for intravenous administration, for example by gravity or using a stationary infusion pump. A retifanlimab composition of the disclosure can be combined with 0.9% sodium chloride or D5W to obtain a retifanlimab dosing solution. In certain embodiments, the administration of the therapeutic dosage is over at least 30 minutes or at least 60 minutes.

In some embodiments, a weight-based dose of about 3 mg/kg to about 10 mg/kg is administered to the patient or subject. In one embodiment, a weight-based dose of about 3 mg/kg is administered to the patient or subject. In another embodiment, a weight-based dose of about 10 mg/kg is administered to the patient or subject. In another specific embodiment, a weight-based dose of about 3 mg/kg to about 10 mg/kg is administered Q2W. In other embodiments, a weight-based dose of about 3 mg/kg is administered Q2W. In other embodiments, a weight-based dose of about 10 mg/kg is administered Q2W. In other embodiments, a weight-based dose of about 3 mg/kg to about 10 mg/kg is administered Q3W. In other embodiments, a weight-based dose of about 3 mg/kg is administered Q3W. In other embodiments, a weight-based dose of about 10 mg/kg is administered Q3W. In other embodiments, a weight-based dose of about 3 mg/kg to about 10 mg/kg is administered Q4W. In other embodiments, a weight-based dose of about 10 mg/kg is administered Q4W.

In one embodiment, a flat dose of about 375 mg is administered to the patient or subject. In one embodiment, a flat dose of about 500 mg is administered to the patient or subject. In one embodiment, a flat dose of about 750 mg is administered to the patient or subject. In other embodiments, a flat dose of about 375 mg is administered Q2W. In other embodiments, a flat dose of about 500 mg is administered Q2W. In other embodiments, a flat dose of about 750 mg is administered Q2W. In other embodiments, a flat dose of about 375 mg is administered Q3W. In other embodiments, a flat dose of about 500 mg is administered Q3W. In other embodiments, a flat dose of about 750 mg is administered Q3W. In other embodiments, a flat dose of about 375 mg is administered Q4W. In other embodiments, a flat dose of about 500 mg is administered Q4W. In other embodiments, a flat dose of about 750 mg is administered Q4W.

In one embodiment, the administration of such doses is over at least about 30 minutes or over at least about 120 minutes. In another embodiment, the administration of such doses is over at least about 30 minutes or over at least about 90 minutes. In another embodiment, the administration of such doses is over at least about 30 minutes or over at least about 60 minutes. In another embodiment, the administration of the retifanlimab dosing solution is by continuous infusion for at least about 30 minutes. In another embodiment, the administration of the retifanlimab dosing solution is by continuous infusion for at least about 60 minutes.

To form a dosing solution, the pharmaceutical composition (i.e., a retifanlimab composition of the disclosure) can be added to a container, such as an IV bag, containing for example 0.9% sodium chloride or D5W (nominal volume 100 mL or 250 mL). In one embodiment, the pharmaceutical composition of the disclosure is swirled gently prior to being added to a container containing 0.9% sodium chloride or D5W. In one embodiment, the container is an IV bag. In one embodiment, the IV bag is a polyvinyl chloride (PVC) bag, a polyolefin copolymer (polypropylene and polyethylene) bag, a PVC bag containing a Di-2-ethyhexyl phthalate (DEHP), a polyolefin bag with polyamide coating, or an ethylene vinyl acetate (EVA) bag. In one embodiment, an in-line filter is used during administration. In one embodiment, the filter has a pore size of 0.2 μm, 5 μm or 15 μm. In another embodiment, a 0.2 μm pore size line-line filter is used. In another embodiment, the filter is a polyvinylidene fluoride or cellulose acetate filter. In another embodiment, the filter is a polyethersulfone (PES) filter. In some embodiments, the desired volume of the pharmaceutical composition of the disclosure is added to the IV bag and can, for example, be gently inverted to mix the dosing solution.

In one embodiment, the prepared dosing solution is used immediately. In another embodiment, the prepared dosing solution is stored at about 25° C. for about 6 hours or at about 2-8° C. for up to about 24 hours. In another embodiment, the prepared dosing solution that is stored at about 2-8° C. for up to about 24 hours is stored at room temperature for a 4 hour equilibration period prior to administration.

The pharmaceutical compositions, containers, and kits of the disclosure can be used in methods for the treatment of a cancer, and in certain embodiments, for treatment of a cancer expressing PD-L1, for example in a therapeutically effective amount or a prophylactically effective amount. In some embodiments, the methods of the disclosure comprise the step of administering a pharmaceutical composition of the disclosure to a subject in need thereof for the treatment of cancer, for example in a therapeutically effective amount or a prophylactically effective amount. In some embodiments, cancers to be treated with pharmaceutical compositions, containers, and kits of the disclosure are selected from the group consisting of: adrenal gland cancer, AIDS-associated cancer, alveolar soft part sarcoma, anal cancer (including squamous cell carcinoma of the anal canal (SCAC)), bladder cancer, bone cancer, brain and spinal cord cancer, breast cancer (including, HER2+ breast cancer or Triple-Negative Breast Cancer (TNBC)), carotid body tumor, cervical cancer (including, HPV-related cervical cancer), chondrosarcoma, chordoma, chromophobe renal cell carcinoma, clear cell carcinoma, colon cancer, colorectal cancer, desmoplastic small round cell tumor, ependymoma, endometrial cancer (including, unselected endometrial cancer, MSI-high endometrial cancer, dMMR endometrial cancer, and/or DNA polymerase (POLE) exonuclease domain mutation positive endometrial cancer), Ewing's sarcoma, extraskeletal myxoid chondrosarcoma, gallbladder or bile duct cancer (including, cholangiocarcinoma bile duct cancer), gastric cancer, gastroesophageal junction (GEJ) cancer, gestational trophoblastic disease, germ cell tumor, glioma, glioblastoma, head and neck cancer (including, squamous cell carcinoma of head and neck (SCCHN)), a hematological malignancy, a hepatocellular carcinoma, islet cell tumor, Kaposi's Sarcoma, kidney cancer (including, renal cell carcinomas (RCC), clear cell RRC, papillary RCC and chromophobe RCC), leukemia (including, acute myeloid leukemia), liposarcoma/malignant lipomatous tumor, liver cancer (including, hepatocellular carcinoma liver cancer (HCC)), lymphoma (including, diffuse large B-cell lymphoma (DLBCL), non-Hodgkin's lymphoma (NHL)), lung cancer (including, small cell lung cancer (SCLC), non-small cell lung cancer (NSCLC)), medulloblastoma, melanoma (including, uveal melanoma), meningioma, mesothelioma (including, mesothelial pharyngeal cancer), multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pharyngeal cancer, pheochromocytoma, pituitary tumor, prostate cancer (including, metastatic castration resistant prostate cancer (mCRPC)), posterious uveal melanoma, renal metastatic cancer, rhabdoid tumor, rhabdomyosarcoma, sarcoma, skin cancer (including Merkel cell carcinoma), a small round blue cell tumor of childhood (including neuroblastoma and rhabdomyosarcoma), soft-tissue sarcoma, squamous cell cancer, stomach cancer, synovial sarcoma, testicular cancer, thymic carcinoma, thymoma, thyroid cancer, urothelial cancer, and uterine cancer.

In one embodiment, a pharmaceutical composition of the disclosure is to be used for the treatment of a cancer selected from the group consisting of: anal cancer, breast cancer, cervical cancer, chromophobe renal cell carcinoma, colorectal cancer, endometrial cancer, gastric cancer, GEJ cancer, glioma, head and neck cancer, kidney cancer, liver cancer, lung cancer, lymphoma, melanoma, multiple myeloma, ovarian cancer, pancreatic cancer, prostate cancer, renal metastatic cancer, skin cancer, urothelial cancer, and a uterine cancer.

In one embodiment, a pharmaceutical composition of the disclosure is used for the treatment of anal cancer. In another embodiment, the anal cancer is SCAC.

In one embodiment, a pharmaceutical composition of the disclosure is used for the treatment of lung cancer. In another embodiment, the lung cancer is NSCLC.

In one embodiment, a pharmaceutical composition of the disclosure is used for the treatment of endometrial cancer. In another embodiment, the endometrial cancer is MSI-high endometrial cancer, dMMR endometrial cancer, and/or POLE exonuclease domain mutation positive endometrial cancer.

In one embodiment, a pharmaceutical composition of the disclosure is used for the treatment of skin cancer. In another embodiment, the skin cancer is Merkel cell carcinoma.

In one embodiment, a pharmaceutical composition of the disclosure is used for the treatment of head and neck cancer. In another embodiment, the head and neck cancer is SCCHN.

In one embodiment, a pharmaceutical composition of the disclosure is used for the treatment of prostate cancer. In another embodiment, the prostate cancer is mCRPC.

In one embodiment, a pharmaceutical composition of the disclosure is used for the treatment of kidney cancer. In another embodiment, the kidney cancer is a RCC. In another embodiment, the kidney cancer is a clear cell RCC.

In one embodiment, a pharmaceutical composition of the disclosure is used for the treatment of melanoma.

In one embodiment, a pharmaceutical composition of the disclosure is used for the treatment of urothelial cancer.

In one embodiment, a pharmaceutical composition of the disclosure is used for the treatment of squamous cell cancer.

In one embodiment, a pharmaceutical composition of the disclosure is used for the treatment of glioma.

In one embodiment, a pharmaceutical composition of the disclosure is used for the treatment of cervical cancer.

In one embodiment, a pharmaceutical composition of the disclosure is used for the treatment of kidney cancer.

In one embodiment, a pharmaceutical composition of the disclosure is used for the treatment of a chromophobe renal cell carcinoma In one embodiment, a pharmaceutical composition of the disclosure is used for the treatment of a renal metastatic cancer.

In one embodiment, a pharmaceutical composition of the disclosure is used for the treatment of uterine cancer.

In some embodiments, a pharmaceutical composition of the disclosure is used for treatment of such cancer wherein such cancer is a metastatic cancer. In some embodiments, a pharmaceutical composition of the disclosure is used for treatment of such cancer wherein such cancer is a metastatic cancer.

In certain of such embodiments, a pharmaceutical composition of the disclosure is used as a neoadjuvant therapy for treatment of such cancer. In certain of such embodiments, a pharmaceutical composition of the disclosure is used as an adjuvant therapy for treatment of such cancer. In other of such embodiments, a pharmaceutical composition of the disclosure is used as a component of a combination therapy for treatment of such cancer.

In certain embodiments, a pharmaceutical composition of the disclosure is used for treatment of such cancer, wherein such cancer expresses PD-L1. Methods and tests approved by regulatory agencies for identifying a cancer expressing PD-L1 have been described (see, e.g., FDA website:fda.gov/CompanionDiagnostics, and include for example PD-L1 IHC 22C3 pharmDx, additional tests are described by Cheung et al., (2019), "Fit-For-Purpose PD-L1 Biomarker Testing For Patient Selection in Immuno-Oncology: Guidelines For Clinical Laboratories From the Canadian Association of Pathologists-Association Canadienne Des Pathologistes (CAP-ACP)." Appl Immunohistochem Mol Morphol 27 (10):699-714).

EXAMPLES

Having now generally described the disclosure, the same will be more readily understood through reference to the following examples, which are provided by way of illustration and are not intended to be limiting of the present disclosure.

Example 1

Development of a Pharmaceutical Composition Containing Retifanlimab

Stable, antioxidant-free, pharmaceutical composition comprising retifanlimab ("the retifanlimab drug product (DP) composition") in a liquid composition in vials was prepared. As disclosed herein, retifanlimab comprises a PD-1 Binding Domain comprising a Heavy Chain having the amino acid sequence of SEQ ID NO:1 and a Light Chain having the amino acid sequence of SEQ ID NO: 2. The Light Chain comprises a Variable Domain ($VL_{PD-1}$) comprising the CDRL1, CDRL2 and CDRL3 of retifanlimab and the Heavy Chain comprises a Variable Domain (VHPD-1) comprising the CDRH1, CDRH2 and CDRH3 of retifanlimab.

1.1. Target Product Profile of Exemplary Retifanlimab DP Composition

The target product profile of the exemplary retifanlimab DP composition, for 250 mg, 375 mg, and 500 mg vials, is shown below in Table 1.

TABLE 1

Target Product Profile of an Exemplary Retifanlimab DP Composition (250 mg, 375 mg and 500 mg vials)

| Product Attribute | Target |
|---|---|
| Dosage form | Injection: Sterile aqueous solution |
| Protein content per vial | ≥250 mg, ≥375 mg, or ≥500 mg |
| Dose | 250 mg, 375 mg, or 500 mg |
| Protein Concentration | ≥25 mg/mL |
| Shelf life | ≥24 months at 2-8° C. |
| Degradants/impurities | Below safety threshold |
| Aggregates | <5% |

1.2. Summary of the Development of the Exemplary Retifanlimab Drug Product (DP) Composition Initially, the protein concentration of 10 mg/mL was chosen to determine the effects of pH, excipients and surfactant. Retifanlimab product stability was evaluated under different storage temperatures, agitation stress at room temperature, and under freeze thaw conditions. Once the optimum formulation buffer was selected, retifanlimab product stability at 25 mg/mL was evaluated under different storage temperatures, agitation stress at room temperature, and under freeze-thaw conditions.

In in these studies, retifanlimab was formulated without the use of antioxidants (e.g., histidine, methionine). The stability of retifanlimab was compared between pH 5 (10 mM sodium acetate buffer) and pH 6 (10 mM phosphate buffer) in the presence of sucrose, sodium chloride and polysorbate 80 (PS80). As described below, retifanlimab precipitated and formed visible particles in sodium phosphate buffer at pH 6 even in the presence of stabilizers. Retifanlimab was observed to be more stable in acetate buffer at pH 5 against different stress conditions and presence of sucrose further stabilized the protein. Thus, in this example, 10 mM sodium acetate buffer (3 mM glacial acetic acid, 7 mM sodium acetate) pH 5 was selected as the formulation buffer for further development.

To achieve a tonicity suitable for intravenous (i.v.) administration, the non-ionic osmolyte sucrose was evaluated alone and in combination with the ionic osmolyte sodium chloride for influence on retifanlimab in this exemplary pharmaceutical formulation. Addition of a surfactant, PS80, was also evaluated to determine if stability is enhanced. Based on the study results, 9% sucrose, 0.01% polysorbate 80 in 10 mM sodium acetate (also referred to herein as 10 mM acetate) pH 5 was selected as formulation buffer for further evaluation in this example. The studies and results are described in more detail below.

1.3. Evaluation of Stability of 10 mg/mL Protein Concentration

1.3.1. Freeze Thaw Study

A freeze/thaw study was performed to assess the impact of freezing at −80° C. and thawing at 25° C. for five cycles on stability of retifanlimab in the four exemplary formulations screened. The samples were analyzed at initial and after 1, 3, and 5 cycles for appearance, sub-visible particles by high accuracy liquid particle counting ("HIAC"), size exclusion high-performance liquid chromatography ("SE-HPLC") and reduced and non-reduced capillary electrophoresis-sodium dodecyl sulfate ("CE-SDS"). The appearance of solutions at all conditions were clear and colorless solution without visible particles. The additional analytical results are summarized in Table 2.

TABLE 2

Freeze-Thaw Cycles Study Results for HIAC, SE-HPLC and Reduced and Non-Reduced CE-SDS Results for 10 mg/mL Retifanlimab Solution in 10 mM Acetate, pH 5*

| Tests Particle size | 9% Sucrose | 9% Sucrose, 0.01% PS80 | 50 mM NaCl, 6% Sucrose | 50 mM NaCl, 6% Sucrose, 0.01% PS80 |
|---|---|---|---|---|
| | | Cumulative Particle Count/mL | | |
| Initial | | | | |
| ≥2 μm | 16,305 | 6,238 | 124,760 | 3,105 |
| ≥5 μm | 638 | 505 | 10,096 | 267 |
| ≥10 μm | 114 | 67 | 1,336 | 57 |
| ≥25 μm | 0 | 0 | 0 | 10 |
| 5 cycles | | | | |
| ≥2 μm | 36,152 | 2,467 | 49,332 | 129,124 |
| ≥5 μm | 16,829 | 248 | 4,952 | 1,981 |
| ≥10 μm | 10,038 | 57 | 1,144 | 105 |
| ≥25 μm | 1,552 | 0 | 0 | 10 |
| SE-HPLC | | % HMWS | | |
| Initial | 2.3 | 2.3 | 2.4 | 2.4 |
| Cycle 1 | 2.4 | 2.3 | 2.4 | 2.4 |
| Cycle 3 | 2.5 | 2.3 | 2.5 | 2.4 |
| Cycle 5 | 2.6 | 2.3 | 2.5 | 2.2 |

TABLE 2-continued

Freeze-Thaw Cycles Study Results for HIAC, SE-HPLC
and Reduced and Non-Reduced CE-SDS Results for 10
mg/mL Retifanlimab Solution in 10 mM Acetate, pH 5*

| Reduced CE -SDS | Main Peak % (HC + LC) | | | |
|---|---|---|---|---|
| Initial | 96.7 | 96.6 | 96.3 | 97.7 |
| Cycle 5 | 97.5 | 96.7 | 97.5 | 97.1 |

| Non-Reduced CE-SDS | Main Peak (%) | | | |
|---|---|---|---|---|
| Initial | 98.4 | 98.3 | 98.0 | 97.3 |
| Cycle 5 | 97.6 | 97.8 | 97.8 | 97.0 |

*Abbreviations used in Table 2:
HMWS = high molecular weight species;
HC = heavy chain;
LC = light chain.

The results obtained show that significantly more sub-visible particles formed in the absence of PS80 in the sucrose alone condition after multiple freeze thaw and presence of PS80 resulted in significant reduction in sub-visible particles. However, in the presence of 50 mM sodium chloride with or without PS80 more sub-visible particles were observed at the initial condition and after 5 freeze thaw cycles. No significant change in HMW species, or purity by reduced and non-reduced CE-SDS were observed after five freeze/thaw cycles for any of the four formulations. From the freeze/thaw study, 9% sucrose, 0.01% PS80, 10 mM acetate pH 5 was the most stable of the exemplary formulations for retifanlimab.

1.3.2. Agitation Study

An agitation study at 250 rpm at 25° C. for 5 days was performed to evaluate stability in all four exemplary formulations during screening. The samples were analyzed at T=0 (no agitation), 1, 3, and 5 days for HIAC, SE-HPLC, reduced and non-reduced CE-SDS. The results are summarized in Table 3.

TABLE 3

Agitation Study Results for HIAC, SE-HPLC and Reduced and non-Reduced
CE-SDS for 10 mg/mL Retifanlimab Solution in 10 mM Acetate, pH 5*

| Tests Particle size | 9% Sucrose | 9% Sucrose 0.01% PS80 | 50 mM NaCl 6% Sucrose | 50 mM NaCl, 6% Sucrose 0.01% PS80 |
|---|---|---|---|---|
| | | Cumulative Particle Count/mL | | |
| Initial (No Agitation) | | | | |
| ≥2 µm | 16,305 | 6238 | 124,760 | 3,105 |
| ≥5 µm | 638 | 505 | 10,096 | 267 |
| ≥10 µm | 114 | 67 | 1,336 | 57 |
| ≥25 µm | 0 | 0 | 0 | 10 |
| Agitated for 5 days | | | | |
| ≥2 µm | 4,286 | 4,229 | 84,572 | 2,905 |
| ≥5 µm | 238 | 486 | 9,716 | 248 |
| ≥10 µm | 0 | 124 | 2476 | 77 |
| ≥25 µm | 0 | 10 | 192 | 0 |
| SE-HPLC | % HMWS | | | |
| Initial (no agitation) | 2.3 | 2.3 | 2.4 | 2.4 |
| T = 1 day | 2.2 | 2.2 | 2.2 | 2.2 |
| T = 3 days | 2.0 | 2.0 | 2.2 | 2.2 |
| T = 5 days | 2.0 | 2.0 | 2.0 | 2.1 |
| Reduced CE | Main Peak % (HC + LC) | | | |
| Initial (no agitation) | 96.7 | 96.6 | 96.3 | 97.7 |
| T = 5 days | 97.3 | 96.9 | 97.1 | 97.3 |

TABLE 3-continued

Agitation Study Results for HIAC, SE-HPLC and Reduced and non-Reduced
CE-SDS for 10 mg/mL Retifanlimab Solution in 10 mM Acetate, pH 5*

| Non-Reduced CE | Main Peak (%) | | | |
|---|---|---|---|---|
| Initial (no agitation) | 98.4 | 98.3 | 98.0 | 97.3 |
| T = 5 days | 96.3 | 96.8 | 98.5 | 96.3 |

*Abbreviations used in Table 3:
HMWS = high molecular weight species;
HC = heavy chain;
LC = light chain.

Sub-visible particles content was higher in the sucrose alone condition (without PS80) as compared to sucrose plus PS80 condition at the initial time point. The sub-visible particle content was significantly elevated in the presence of sodium chloride and absence of PS80. Presence of PS80 in the salt condition reduced the sub-visible particles and levels were comparable to the initial and after 5 days of shaking. No significant change in BMW species, or purity by reduced and non-reduced CE-SDS were observed after five days of shaking for any of the four formulations.

1.3.3. Accelerated and Stressed Thermal Study

Retifanlimab in the four exemplary 10 mg/mL acetate compositions was stored at an accelerated condition of 25° C. and stressed condition of 40° C. for three weeks. The samples were analyzed at initial, 1, 2, and 3-week time points for appearance and SE-HPLC to determine stability. Appearance analysis showed that all samples were clear and colorless solutions without visible particles at all time points. The SE-HPLC results for accelerated and stressed conditions are shown in Table 4.

TABLE 4

SE-HPLC Results for 10 mg/mL Solution in 10 mM Acetate
pH 5 at Accelerated and Stressed Conditions*

| Tests SE-HPLC | 9% Sucrose | 9% Sucrose, 0.01% PS80 | 50 mM NaCl, 6% Sucrose | 50 mM NaCl, 6% Sucrose, 0.01% PS80 |
|---|---|---|---|---|
| | | % HMWS | | |
| Initial | 2.3 | 2.3 | 2.4 | 2.4 |
| T = 1 w @25° C. | 1.8 | 1.8 | 1.8 | 1.8 |
| T = 2 w @25° C. | 1.6 | 1.6 | 1.6 | 1.7 |
| T = 3 w @25° C. | 1.6 | 1.6 | 1.6 | 1.6 |
| T = 1 w @40° C. | 1.3 | 1.3 | 1.5 | 1.5 |
| T = 2 w @40° C. | 1.4 | 1.5 | 1.8 | 1.8 |
| T = 3 w @40° C. | 1.6 | 1.6 | 2.0 | 2.1 |

*Abbreviations used in Table 4:
T = time;
w = week;
HMWS = high molecular weight species.

The results show that the all four acetate compositions were stable for 3 weeks at 25° C., however, HMW species of retifanlimab formed more rapidly when stored at 40° C. in the presence of sodium chloride when compared with formulations in the absence of sodium chloride. These results demonstrate a good stability profile at stressed condition as further evidence that 9% sucrose, 0.01% PS80 in 10 mM acetate pH 5 is a suitable formulation buffer for retifanlimab.

Retifanlimab in 10 mM acetate, 9% sucrose and 0.01% PS80 was evaluated as a suitable DP composition and samples stored from the accelerated (25° C.) stability study were evaluated to determine if any change in charge heterogeneity was observed after 1 month storage. The cIEF shown in Table 5 confirms the acceptable charge variant stability profile.

TABLE 5 cIEF Results for 10 mg/mL Solution in 10 mM Acetate
pH 5 at Accelerated and Stressed Conditions*

| Tests | 9% Sucrose, 0.01% PS80 | | |
|---|---|---|---|
| cIEF | % AV | % MCP | % BV |
| Initial | 24.0 | 71.2 | 4.8 |
| T = 1 M @25° C. | 24.6 | 70.0 | 5.4 |

*Abbreviations used in Table 5:
T = time;
M = month;
AV = Acidic Charge Variants;
MCP = Main Charge Peak;
BV = Basic Charge Variants.

1.4. Evaluation of Stability at the Selected Protein Concentration (25 mg/mL)

A protein concentration was selected to be 25 mg/mL based on the clinical dosing planned for dose escalation and expansion studies during early clinical studies, as well as convenience to handle less volume with higher protein concentration and accommodation of a smaller vial size per given strength. Thus, the stability of the exemplary DP composition (10 mM acetate, pH 5, 9% sucrose, 0.01% polysorbate 80, pH 5.1) was evaluated at 25 mg/mL in a similar manner as the 10 mg/mL studies. Studies performed included a freeze/thaw study (freezing at −80° C. and thawing at 25° C. for five cycles; Table 6), an agitation study (250 rpm at 25° C. for 5 days; Table 7) and an accelerated storage study (25° C. accelerated storage condition for 1 month; Table 8).

TABLE 6

Freeze-Thaw Study Results for Subvisible Particle, SE-HPLC, CE and ciEF at 25 mg/mL Retifanlimab*

| Study | Subvisible Particle Count (count/mL) Particle Size | | | | SE-HPLC | | CE | | ciEF | | |
|---|---|---|---|---|---|---|---|---|---|---|---|
| | ≥2 µm | ≥5 µm | ≥10 µm | ≥25 µm | M % | HMW % | Non-R % | R % | AV % | MCP % | BV % |
| Initial | 339 | 25 | 11 | 2 | 98.8 | 1.1 | 97.2 | 95.3 | 23.4 | 71.7 | 4.9 |
| F/T 1 cycles | NT | NT | NT | NT | 98.6 | 1.3 | 97.5 | 95.3 | 23.2 | 72.0 | 4.8 |
| F/T 3 cycles | NT | NT | NT | NT | NT | NT | 97.2 | 94.4 | 25.1 | 69.8 | 5.0 |
| F/T 5 cycles | 884 | 119 | 35 | 6 | 98.7 | 1.3 | 97.4 | 94.9 | 23.7 | 71.6 | 4.7 |

TABLE 7

Agitation Study Results for Subvisible Particle, SE-HPLC, CE and ciEF at 25 mg/mL Retifanlimab*

| Study | Subvisible Particle Count (count/mL) Particle Size | | | | SE-HPLC | | CE | | ciEF | | |
|---|---|---|---|---|---|---|---|---|---|---|---|
| | ≥2 µm | ≥5 µm | ≥10 µm | ≥25 µm | M % | HMW % | Non-R % | R % | AV % | MCP % | BV % |
| Initial (no agitation) | 339 | 25 | 11 | 2 | 98.8 | 1.1 | 97.2 | 95.3 | 23.4 | 71.7 | 4.9 |
| Agitation T = 1 day | NT | NT | NT | NT | 97.0 | 1.6 | 97.2 | 95.0 | 25.2 | 69.8 | 5.1 |
| Agitation T = 3 day | NT | NT | NT | NT | NT | NT | 97.2 | 95.8 | 25.5 | 69.7 | 4.9 |
| Agitation T = 5 day | 202 | 36 | 18 | 4 | 98.4 | 1.6 | 97.2 | 95.0 | 24.1 | 70.5 | 5.3 |

TABLE 8

Subvisible Particle, SE-HPLC, CE and ciEF at 25 mg/mL Retifanlimab during Storage at 25° C.*

| Study | Subvisible Particle Count (count/mL) Particle Size | | | | SE-HPLC | | CE | | ciEF | | |
|---|---|---|---|---|---|---|---|---|---|---|---|
| | ≥2 µm | ≥5 µm | ≥10 µm | ≥25 µm | M % | HMW % | Non-R % | R % | AV % | MCP % | BV % |
| Initial | 339 | 25 | 11 | 2 | 98.8 | 1.1 | 97.2 | 95.3 | 23.4 | 71.7 | 4.9 |
| T = 1 M @ 25° C. | 192 | 28 | 12 | 1 | 98.5 | 1.4 | NT | NT | 25.5 | 69.2 | 5.2 |

*Abbreviations used in Tables 6-8:
CE = capillary electrophoresis;
M = monomer;
HMW = high molecular weight species;
Non-R = non-reduced;
R = reduced;
T = time;
1 M = 1 month;
M = monomer;
AV = acidic variants;
BV = basic variants;
MCP = main charge peak;
F/T = freeze/thaw.

* Abbreviations used in Tables 6-8: CE=capillary electrophoresis: M=monomer: HMV=high molecular weight species: Non-R=non-reduced: R=reduced: T=time; 1M=1 month: M=monomer: AV=acidic variants: BV=basic variants: MCP=main charge peak: F/T=freeze/thaw.

As shown in Tables 6-8, the formulation demonstrated no significant increase in subvisible particles by HIAC light obscuration analysis. Additionally, no significant changes were observed in HMW species by SE-HPLC, fragments by non-reduced and reduced CE-SDS and charge heterogeneity by cIEF. The results demonstrate acceptable stability of 25 mg/mL retifanlimab in the formulation.

A retifanlimab DP composition was formulated at 25 mg/mL retifanlimab in 10 mM sodium acetate (0.95 mg/mL sodium acetate trihydrate, 0.18 mg/mL glacial acetic acid), 90 mg/mL sucrose, and 0.1 mg/mL polysorbate 80, at pH 5.1. The components of the selected retifanlimab DP composition are shown below in Table 9. The retifanlimab DP composition was provided in 10 mL or 20 mL Type 1 borosilicate vials as shown in Table 9: 250 mg/10 mL (10 mL vial), 375 mg/15 mL (20 mL vial) or 500 mg/20 mL (20 mL vial).

TABLE 9

Retifanlimab DP Composition (250 mg, 375 mg, and 500 mg vials)

| Components | DP Composition | Each mL | 10 mL/vial | 15 mL/vial | 20 mL/vial |
|---|---|---|---|---|---|
| Retifanlimab monoclonal antibody | 25 mg/mL in formulation buffer | 25 mg | 250 mg | 375 mg | 500 mg |
| Glacial acetic acid | 0.18 mg/mL | 0.18 mg | 1.8 mg | 2.7 mg | 3.6 mg |
| Sodium acetate trihydrate^ | 0.95 mg/mL | 0.95 mg | 9.5 mg | 14.25 mg | 19 mg |
| Sucrose | 90 mg/mL | 90 mg | 900 mg | 1350 mg | 1800 mg |
| Polysorbate 80 ("PS80") | 0.10 mg/mL | 0.10 mg | 1.0 mg | 1.5 mg | 2 mg |
| Water for Injection | q.s. to 1 mL | q.s. to volume | q.s. to volume | q.s. to volume | q.s. to volume |

^it will be appreciated that sodium acetate monohydrate and/or sodium acetate anhydrous and/or sodium acetate trihydrate may be used in quantities required to obtain a final concentration of about 7 mM of acetate (e.g. 0.57 mg/mL of sodium acetate anhydrous, or 0.7 mg/mL sodium acetate monohydrate)

1.5. Retifanlimab Composition Characterization and Robustness Study Using Design of Experiments A Design of Experiments (DoE) study was then performed to verify the robustness of the exemplary retifanlimab DP composition for use and to develop a control strategy for a retifanlimab DP composition manufacturing process. The DoE study was used to demonstrate the robustness of the exemplary retifanlimab DP composition over a range of composition parameters beyond the target composition, and the retifanlimab DP composition was evaluated at the recommended storage temperature of 2-8° C. for 24 months and at accelerated temperature condition of 25° C. for 6 months.

Ranges of five composition parameters were investigated as shown in Table 10 and Table 11. In addition to all the formulations designed for the DoE study design (F1-F16), center point formulations (F9 and F16), and low (21 mg/mL, F1, F4, F6, F7, F12, and F15) and high (29 mg/mL, F2, F3, F5, F8, F13 and F14) protein concentration formulations were evaluated. All the formulation parameters evaluated in this study were intended to be beyond the upper and lower limits of their respective concentrations during manufacturing. For example, the range for PS80 was varied from 0.02 mg/mL to 0.53 mg/mL. In this particular case, the values being tested were substantially wider than the desired range during manufacturing. DoE study pH was evaluated within the pH 4.5 to pH 5.7. The protein concentration range evaluated was target ±15%.

TABLE 10

Target Formulation and DoE Study Ranges Evaluated

| Parameter | Target Value | DoE Study Range |
|---|---|---|
| Protein concentration | 25 mg/mL | 21-29 mg/mL |
| Combined concentration of acetate (acetic acid and sodium acetate trihydrate) | 10 mM | 5-25 mM |
| pH | 5.1 | 4.5-5.7 |
| Sucrose | 90 g/L | 76-104 g/L |
| PS80 | 0.1 g/L | 0.02-0.53 g/L |

TABLE 11

Fractional Factorial Experimental Design for Retifanlimab Formulation Robustness Study

| Formulation No. | Sucrose (g/L) | pH | PS80 (g/L)[a] | Protein Concentration (g/L) | Buffer Salt Concentration (mM) |
|---|---|---|---|---|---|
| F1 | 76 | 4.5 | 0.19 | 21 | 10 |
| F2 | 76 | 4.5 | 0.51 | 29 | 10 |
| F3 | 76 | 5.7 | 0.25 | 29 | 10 |
| F4 | 76 | 5.7 | 0.53 | 21 | 10 |
| F5 | 104 | 4.5 | 0.21 | 29 | 10 |
| F6 | 104 | 4.5 | 0.46 | 21 | 10 |
| F7 | 104 | 5.7 | 0.18 | 21 | 10 |
| F8 | 104 | 5.7 | 0.53 | 29 | 10 |
| F9 | 90 | 5.1 | 0.08 | 25 | 10 |
| F10 | 90 | 5.1 | 0.43 | 25 | 5 |
| F11 | 90 | 5.1 | 0.41 | 25 | 25 |
| F12 | 76 | 4.5 | 0.03 | 21 | 10 |
| F13 | 76 | 5.7 | 0.03 | 29 | 10 |
| F14 | 104 | 4.5 | 0.02 | 29 | 10 |
| F15 | 104 | 5.7 | 0.03 | 21 | 10 |
| F16 | 90 | 5.1 | 0.08 | 25 | 10 |

[a]The actual PS80 concentrations are listed, which were quantitated after formulations were prepared.

After the designated formulations were prepared via tangential flow filtration, product stability was assessed for up to 48 months at the intended long-term storage condition (2-8° C.) and for 6 months under an accelerated condition (25° C.) (see Example 3).

At each time point, the impact of formulation variables on drug product quality was evaluated using the following assays: visual appearance, high performance size exclusion chromatography (SE-HPLC), capillary isoelectric focusing (cIEF), protein concentration ($Abs_{280}$), sub-visible particle counting (HIAC), pH, and PD-1 Binding ELISA.

The statistical significance of each formulation variable on the product quality was evaluated by performing a multivariate analysis (MVA). Prediction profilers were generated to understand the relationship between individual formulation parameters and product quality as well as the importance of each formulation factor.

1.5.1. Results from Formulation Robustness Stability Study Using Design of Experiment The experimental design and the statistical analysis provide an understanding of the relationship between the product quality attributes and the chosen formulation parameters as well as the storage conditions. The prediction profilers for the formulation samples stored at 5±3° C. and 25° C. for 6 months are shown in FIG. 1. The results from the formulation robustness stability study for different product quality attributes are discussed in the sections below.

1.5.1.1. Results of % Monomer, % HMW and % LMW Species Monitored by SE-HPLC

SE-HPLC studies demonstrated that for both the % monomer (M) and % HMW, the formulated samples stored at 2-8° C. were stable for 6 months with the data trend showing no major changes in stability. For monomer content, no decrease above 0.3% was detected after 6 months of storage at 2-8° C., regardless of the pH level. Under the accelerated storage condition at 25° C., the monomer purity showed a drop of 0.1-2.6% over 6 months. Correspondingly, the % HMW increased 0.1-2.2% over 6 months in all 16 formulations.

These stability data demonstrate that variations in the pH, excipients and buffer conditions of the retifanlimab formulation result in no major changes, within the ranges evaluated, in the % monomer, % HMW and % LMW species as a function of storage time at the recommended 2-8° C. storage temperature.

1.5.1.2. Charge Heterogeneity Changes Monitored by cIEF

The charge heterogeneity of all the exemplary formulations was monitored via cIEF by measuring the acidic variants ("AV"), the main charge peak ("MCP"), and the basic variants ("BV").

Within the range of excipients and pH conditions tested, the storage at the intended temperature (2-8° C.) results in only minor changes in charge heterogeneity, and no statistically significant impact from any of the formulation parameters was found on the charge variants for the formulations stored at 2-8° C. More pronounced changes were observed after 6 months' storage at 25° C. The pH and PS80 have a statistically significant impact on the charge heterogeneity for the exemplary formulations at 25° C.

At 2-8° C., only a slight increase of AV was detected after 6 months, which was no more than 1.2%. After 6 months storage at 25° C., the AV level increased by an average of 13.2% and 14.4% for the formulation at pH 5.7 and pH 4.5, respectively. In addition, an increase of 12.8% in the AV was observed for the target formulation at pH 5.1.

Correspondingly, slight variations in the cIEF MCP results were observed for all 16 formulations after storing for 6 months at the long-term condition (2-8° C.). The drop of MCP level was no more than 0.6%. However, under the accelerated condition at 25° C., the MCP level decreased up to 14.5%.

At 2-8° C., a slight drop of BV was detected and the decrease was no more than 0.9%. Even more pronounced changes in BV levels occurred for the samples stored at 25° C. for up to 6 months, the decrease was no more than 4.9%.

The results of the stability study showed that pH=5.1±0.3 is the pH range where the degradants are the lowest at the recommended 2-8° C. storage. These formulation robustness stability studies demonstrate that the pH of the excipients and buffer conditions of the retifanlimab formulation results in only minor changes in the charge heterogeneity profile, within the ranges evaluated, during storage at the recommended storage temperature of 2-8° C. These minor changes in the charge heterogeneity variants did not translate to major changes in the relative potency of retifanlimab.

1.5.1.3. Visual Appearance and Subvisible Particles

The appearance of all the formulations with respect to clarity and visible particles was determined. Notably, a higher opalescence with precipitates was observed for formulation F13 relative to other formulations, especially for the samples stored at 2-8° C. Without wishing to be bound by a particular theory, such physical instability is attributed to the combination effect of each individual formulation parameter being at its worst edge condition: the lowest PS80 content, the lowest sucrose content, the highest pH, coupled with the highest protein concentration, which caused the protein precipitation. Based on the visual appearance results and subvisible particle data, the PS80 levels evaluated were effective in stabilizing the retifanlimab DP composition against particle formation.

1.6. Formulation Development Summary

Based on the formulation development studies, the exemplary antioxidant-free DP composition (25 mg/mL retifanlimab, 10 mM acetate, 9% sucrose, and 0.01% PS80 at pH 5.1), provided good stability and resulted in an optimal composition of retifanlimab at a concentration of 25 mg/mL, and higher retifanlimab concentrations are contemplated and supported by these studies. As a subsequent step, a formulation robustness study was intended to establish the robustness of the exemplary retifanlimab DP composition by varying a series of formulation parameters. In agreement with the historical stability profile of retifanlimab DP, more pronounced chemical degradation effects were observed under accelerated storage conditions at an elevated temperature (25° C.) than the long-term storage conditions (2-8° C.). At 2-8° C., pH is the only formulation parameter that had a statistically significant effect on product stability, however the observed changes are not practically significant because the actual values are well within the specifications for the quality attributes and, in some cases, within the assay variability.

Under the accelerated storage condition (25° C.), the different pH and PS80 levels had an impact on aggregates formation (SE-HPLC) and charge heterogeneity (cIEF) over time. Ionic strength and protein concentration were also observed to have an impact on basic variants and HMW %, respectively. However, the actual values for all the quality attributes are still well within the specifications.

In summary, the data collected from the formulation robustness study support the pH, PS80, sucrose, and buffer salt concentration specifications of the DP composition. In contrast to other described antibody compositions, the DP composition provides a stable composition of retifanlimab without the addition of antioxidants.

1.7. How the Retifanlimab Composition is Supplied in Vials

Retifanlimab DP composition is supplied as a sterile buffered aqueous solution and presented in USP and Ph. Eur. conforming Type I borosilicate 10 mL (250 mg/vial) or 20 mL (375 mg/vial and 500 mg/vial) glass vials capped with a 20 mm FluroTec® and B2-40 coated butyl rubber stoppers. The components of the retifanlimab DP composition are provided in Table 9. The nominal content of each retifanlimab DP composition vial was 10 mL, 15 mL or 20 mL. Each vial was filled with a 0.6 mL overfill of liquid. An overfill was included to ensure sufficient volume for withdrawal of 10 mL (250 mg), 15 mL (375 mg), and 20 mL (500 mg) of retifanlimab for dose delivery. The target fill volume, deliverable volume and vial/syringe hold up volumes were determined by extractable volume testing. Retifanlimab DP composition is a colorless to pale yellow, clear to opalescent solution that is practically free from visible particles. Retifanlimab DP composition supplied as described in this section was used in the Administration Compatibility and Long-Term and Accelerated Stability Studies described below.

Example 2

Retifanlimab IV Administration Compatibility Studies

Retifanlimab DP composition is available in a single-dose vial (see Example 1.7) and is administered as an intravenous (IV) infusion following dilution in normal saline (0.9% Sodium Chloride Injection, USP) or D5W (Dextrose 5% in Water, USP). The dilution is calculated based upon the amount to be administered, for example a flat dose of 375 mg (it will be understood that for a weight-based dose the patient's body weight and the dose are used to calculate the amount). To prepare the infusion, solution dilution of retifanlimab is performed in a commercially available IV administration bag containing normal saline or D5W. The infusion solution is administered to the patient from the dose-prepared 0.9% sodium chloride, or D5W, IV bag with a commercially available IV pump and IV administration tubing set. As described in more detail below, stability and compatibility studies were performed with the dilution and storage of dose-prepared retifanlimab at 25° C. (up to 6 hours) and up to 24 hours at 2-8° C. and IV administration of retifanlimab using unfiltered and filtered IV infusion sets for 30 minute and 60 minute IV infusion periods.

In the initial compatibility studies, retifanlimab DP composition was diluted in IV bags of the same composition as those commonly used in the clinic, i.e., polyolefin copolymer (polypropylene and polyethylene), PVC containing DEHP, polyolefin with polyamide coating, and EVA which were held at 25° C. The dilution scheme in the test IV bags followed a bracketing approach, whereby multiple drug concentrations (1.4 mg/mL, 4.5 mg/mL and 10 mg/mL) were tested for each IV bag type, representing high and low dose concentrations. Structural integrity of retifanlimab was maintained under all conditions and time points as assessed by size exclusion chromatography (SE-HPLC) and protein concentration recovery. These studies support the stability of retifanlimab and its compatibility for clinical administration when pharmaceutical compositions of the disclosure are diluted in 0.9% sodium chloride or D5W in PVC, polyolefin, and polyolefin copolymer IV bags.

2.1. Overview of In-Use Compatibility Studies with Retifanlimab

One compatibility study of retifanlimab was conducted using normal saline as a diluent. A second compatibility study of retifanlimab was conducted using D5W as the diluent. A third compatibility study was performed to implement the filtered extension sets to reduce any subvisible proteinaceous particles. These studies were performed to demonstrate the compatibility and stability of an exemplary retifanlimab DP composition with an IV infusion set with a 0.2 µm, 5 µm, or 15 µm pore size filter. A fourth study was conducted to evaluate the temperature cycling and shaking study of the IV solution for the short-term stability of an exemplary retifanlimab dosing solution preparations to simulate transport of prepared IV bag from a clinical pharmacy to a satellite site for administration.

The types of IV bags, infusion sets and filters that were tested are summarized in Tables 12-14.

TABLE 12

IV Bags Tested (Normal Saline and D5W)

| Contact Material | Volume per Bag | Normal Saline | D5W |
|---|---|---|---|
| Polyvinyl chloride (PVC) and Di-2-ethylhexyl phthalate (DEHP) | 100 mL and 250 mL | √ | √ |
| Polyolefin Copolymer | 100 mL and 250 mL | √ | √ |
| Polyolefin with Polyamide | 100 mL and 250 mL | √ | √ |
| Ethylene Vinyl Acetate (EVA) | 100 mL and 250 mL | √ | √ |

TABLE 13

Administration Sets Tested

| Description | Contact Material |
|---|---|
| Administration Set, with 0.2 µm in line polyethersulfone (PES) filter eg. Alaris ® from Becton & Dickinson | Polyethylene (PE) |
| Administration Set, with 0.2 µm in-line PES filter, eg., Infusomat ® from B. Braun | Polyurethane (PUR) |
| Administration Set with 0.2 µm in-line PES filter, eg. Continu-Flo ® from Baxter | Polyvinyl chloride (PVC) and Di-2-ethylhexyl phthalate (DEHP) |

TABLE 14

Add-On Filters Tested

| Description | Contact Material |
|---|---|
| 15 µm Mesh Filter | Mesh Membrane |
| 5.0 µm Membrane Filter | Polyethersulfone (PES) |
| 0.2 µm Membrane Filter | Polyvinylidene Fluoride (PVDF) |
| 0.2 µm Membrane Filter | Cellulose Acetate (CA) |

2.2. Evaluation of Retifanlimab In-Use Compatibility with 0.9% Normal Saline

The compatibility of retifanlimab in the exemplary retifanlimab DP composition (at concentrations of 1.4 mg/mL, 4.5 mg/mL, and 10 mg/mL) with normal saline in different size IV bags (100 mL and 250 mL) composed of different type of materials (Table 12), different administration sets (Table 13) and in-line 0.2 µm PES membrane sterile filter were evaluated.

2.2.1. Study Design

Retifanlimab in the exemplary retifanlimab DP composition, was diluted with normal saline at concentrations 1.4 mg/mL, 4.5 mg/mL, and 10 mg/mL in either 100 mL or 250 mL IV bags containing normal saline (Table 12). For concentration of 1.4 mg/mL retifanlimab IV solution preparation, a 250 mL IV bag was used and for 4.5 mg/mL and 10 mg/mL concentrations, 100 mL bags were used. IV bags were then stored at room temperature for 6 hours and at 2-8° C. for 24 hours. The bags stored at 2-8° C. were always followed by a room temperature equilibration period of 4 hours. Samples were collected from each bag upon completion of dose preparation (T=0) and after the incubation period was completed (Pre-infusion sample).

After completion of the incubation periods, the bags were connected to the corresponding IV administration set with in-line filter (low protein binding 0.2 µm PES membrane filter). The entire contents of the bag were infused (by simulation) over 25 minutes (in anticipation of the "worst-case scenario" for the target 30 minutes target infusion time) and "post-infusion" samples were collected and tested.

2.2.2. Results

The results of these studies demonstrate that there were no significant changes observed in protein concentration, pH, appearance and size distribution (SE-HPLC), charge distribution (cIEF), and potency by ELISA for all testing groups. The percent protein recovery of retifanlimab for all concentrations after storage of IV bags at two conditions: 6-hour incubation at room temperature and 24-hour at refrigerated temperature, followed by infusion for 30 minutes showed no significant change relative to protein concentration at T=0 for each condition.

The infusion solutions in normal saline had elevated subvisible particles at the pre-infusion time point. However, the in-line filter infusion sets were able to reduce subvisible particulates as shown by the post-infusion subvisible particles results. Representative results of the in-use compatibility studies with normal saline as administrative mixture with the use of PVC+DEHP IV Bag and PE Infusion Set, for low-dose (1.4 mg/mL; Table 15) and high-dose (10 mg/mL; Table 16) retifanlimab are shown below.

TABLE 15

Compatibility of Retifanlimab in Normal Saline in (PVC + DEHP) IV Bag and PE Infusion Set at 1.4 mg/mL Concentration*

| Test | Results Reported | 6 Hours at RT | | | 24 Hours at 2-8° C. | | |
|---|---|---|---|---|---|---|---|
| | | T = 0 | Pre Infusion | Post Infusion | T = 0 | Pre Infusion | Post Infusion |
| Concentration | mg/mL | 1.4 | 1.4 | 1.4 | 1.3 | 1.4 | 1.3 |
| | % $T_0$ Conc. | NA | 100 | 100 | NA | 107.7 | 100 |
| pH | pH | 5.3 | 5.2 | 5.2 | 5.2 | 5.3 | 5.2 |
| Appearance | Clarity | C | C | C | C | C | C |
| | Color | L | L | L | L | L | L |
| | Particulates | FNP, FPP | FNP, FPP | FNP, FPP | FNP, FPP | FNP, FPP | FNP, FPP |
| Sub-visible Particle Count (per mL) | ≥2 µm | 1,389 | 1,059 | 696 | 734 | 1,016 | 153 |
| | ≥10 µm | 71 | 48 | 53 | 28 | 53 | 1 |
| | ≥25 µm | 3 | 5 | 1 | 2 | 4 | 0 |
| SE-HPLC | % Monomer | 98.7 | 98.7 | 98.7 | 98.7 | 98.7 | 98.7 |
| | % HMWS | 1.2 | 1.2 | 1.2 | 1.2 | 1.2 | 1.2 |
| | % LMWS | 0.2 | 0.2 | 0.2 | 0.2 | 0.2 | 0.2 |
| cIEF | % Main Charge Peak | 74.8 | NT | 74.6 | 74.8 | NT | 74.3 |
| | % Acidic Variants | 17.5 | NT | 16.8 | 17.5 | NT | 17.8 |
| | % Basic Variants | 7.8 | NT | 8.6 | 7.8 | NT | 8.0 |
| ELISA | Relative Potency (%) | 104 | NT | 98 | 104 | NT | 96 |

TABLE 16

Compatibility of Retifanlimab in Normal Saline in PVC + DEHP IV Bag and PE Infusion Set at 10 mg/mL Concentration*

| Test | Results Reported | 6 Hours at RT | | | 24 Hours at 2-8° C. | | |
|---|---|---|---|---|---|---|---|
| | | $T_0$ | Pre Infusion | Post Infusion | $T_0$ | Pre Infusion | Post Infusion |
| Concentration | mg/mL | 10.4 | 10.3 | 10.4 | 10.3 | 10.3 | 10.3 |
| | % $T_0$ Conc. | NA | 99 | 100 | NA | 100 | 100 |
| pH | pH | 5.2 | 5.2 | 5.1 | 5.1 | 5.2 | 5.2 |
| Appearance | Clarity | C | C | C | C | C | C |
| | Color | L | L | L | L | L | L |
| | Particulates | FP | FP | FP | FP | FP | FP |

TABLE 16-continued

Compatibility of Retifanlimab in Normal Saline in
PVC + DEHP IV Bag and PE Infusion Set at 10 mg/mL Concentration*

| | | | 6 Hours at RT | | | 24 Hours at 2-8° C. | |
|---|---|---|---|---|---|---|---|
| Test | Results Reported | $T_0$ | Pre Infusion | Post Infusion | $T_0$ | Pre Infusion | Post Infusion |
| Sub-visible Particle Count (per mL) | ≥2 μm | 1,658 | 1,651 | 114 | 937 | 1,919 | 128 |
| | ≥10 μm | 28 | 37 | 4 | 12 | 42 | 4 |
| | ≥25 μm | 2 | 0 | 0 | 1 | 1 | 0 |
| SE-HPLC | % Monomer | 98.3 | 98.4 | 98.4 | 98.3 | 98.4 | 98.4 |
| | % HMWS | 1.6 | 1.5 | 1.5 | 1.6 | 1.5 | 1.5 |
| | % LMWS | 0.1 | 0.1 | 0.1 | 0.1 | 0.1 | 0.1 |
| CIEF | % Main Charge Peak | NT | NT | 73.2 | NT | NT | 73.6 |
| | % Acidic Variants | NT | NT | 17.5 | NT | NT | 17.3 |
| | % Basic Variants | NT | NT | 9.3 | NT | NT | 9.0 |
| ELISA | Relative Potency (%) | NT | NT | 112 | NT | NT | 115 |

*Abbreviations used in Tables 15-16:
T = time;
NA = not applicable;
NT = not tested;
HMWS = high molecular weight species;
LMWS = low molecular weight species;
FP = free of particles;
FNP = essentially free of visible particles;
FPP = essentially free of proteinaceous particles;
C = clear;
L = colorless.

* Abbreviations used in Tables 15-16: T=time; NA=not applicable: NT=not tested; HMWS=high molecular weight species; LMWS=low molecular weight species; FP=free of particles; FNP=essentially free of visible particles; FPP=essentially free of proteinacceous particles; C=clear; L=colorless.

2.3. Evaluation of Retifanlimab In-Use Compatibility with D5W

The compatibility of retifanlimab in the exemplary retifanlimab DP composition (at concentrations 1.4 mg/mL, 4.5 mg/mL, and 10 mg/mL) with D5W in different size IV bags (100 mL and 250 mL) composed of different type of materials (Table 12), different administration sets (Table 13) and in-line 0.2 μm PES membrane sterile filter were evaluated.

2.3.1. Study Design

Retifanlimab was diluted with D5W at concentrations 1.4 mg/mL, 4.5 mg/mL, and 10 mg/mL in either 100 mL or 250 mL IV bags containing D5W (Table 12). For concentration of 1.4 mg/mL retifanlimab IV solution preparation, a 250 mL IV bag was used and for 4.5 mg/mL and 10 mg/mL concentrations, 100 mL bags were used. IV bags were then stored at room temperature for 6 hours and at 2-8° C. for 24 hours. The bags stored at 2-8° C. were always followed by a room temperature equilibration period of 4 hours. Samples were collected from each bag upon completion of dose preparation (T=0) and after the incubation period was completed (Pre-infusion sample).

After completion of the incubation periods, the bags were connected to the corresponding IV administration set with in-line filter (low protein binding 0.2 μm PES membrane filter). The entire contents of the bag were infused (by simulation) over 25 minutes (in anticipation of the "worst-case scenario" for the target 30 minutes target infusion time) and "post-infusion" samples were collected and tested.

2.3.2. Results

The results of these studies demonstrate that there were no significant changes observed in protein concentration, pH, appearance and size distribution (SE-HPLC), charge distribution (cIEF), and potency by ELISA for all testing groups. The percent protein recovery of retifanlimab for all concentrations after storage of IV bags at two conditions: 6-hour incubation at room temperature and 24-hour at refrigerated temperature, followed by infusion for 30 minutes showed no significant change relative to protein concentration at T=0 for each condition.

The infusion solutions with D5W had less sub-visible particle formation at the pre-infusion time point than when normal saline was used as admixture. Moreover, the in-line filter infusion sets were able to reduce subvisible particulates as shown by the post-infusion sub-visible particles results. Representative results of the in-use compatibility studies with D5W as administrative mixture with the use of PVC+ DEHP IV Bag and PE Infusion Set, for low-dose (1.4 mg/mL; Table 17) and high-dose (10 mg/mL; Table 18) retifanlimab are shown below.

TABLE 17

Compatibility of Retifanlimab in Dextrose in PVC + DEHP IV Bag and PUR
Infusion Set at 1.4 mg/mL Concentration*

| | | | 6 Hours at RT | | | 24 Hours at 2-8° C. | |
|---|---|---|---|---|---|---|---|
| Test | Results Reported | $T_0$ | Pre Infusion | Post Infusion | $T_0$ | Pre Infusion | Post Infusion |
| Concentration | mg/mL | 1.5 | 1.5 | 1.4 | 1.4 | 1.4 | 1.3 |
| | % $T_0$ Conc. | NA | 100 | 93.3 | NA | 100 | 92.9 |

TABLE 17-continued

Compatibility of Retifanlimab in Dextrose in PVC + DEHP IV Bag and PUR Infusion Set at 1.4 mg/mL Concentration*

| Test | Results Reported | 6 Hours at RT | | | 24 Hours at 2-8° C. | | |
|---|---|---|---|---|---|---|---|
| | | $T_0$ | Pre Infusion | Post Infusion | $T_0$ | Pre Infusion | Post Infusion |
| pH | pH | 5.1 | 5.1 | 5.1 | 5.1 | 5.2 | 5.2 |
| Appearance | Clarity | C | C | C | C | C | C |
| | Color | L | L | L | L | L | L |
| | Particulates | FNP, FPP | FNP, FPP | FNP, FPP | FNP, FPP | FNP, FPP | FNP, FPP |
| Sub-visible Particle Count (per mL) | ≥2 μm | 157 | 142 | 170 | 380 | 127 | 21 |
| | ≥10 μm | 5 | 2 | 12 | 5 | 5 | 2 |
| | ≥25 μm | 1 | 1 | 0 | 0 | 0 | 1 |
| SE-HPLC | % Monomer | 98.6 | 98.6 | 98.7 | 98.6 | 98.6 | 98.6 |
| | % HMWS | 1.2 | 1.2 | 1.2 | 1.3 | 1.2 | 1.2 |
| | % LMWS | 0.2 | 0.2 | 0.2 | 0.2 | 0.2 | 0.2 |
| cIEF | % Main Charge Peak | 74.8 | NT | 73.6 | 74.8 | NT | 74.7 |
| | % Acidic Variants | 17.5 | NT | 18.8 | 17.5 | NT | 18.8 |
| | % Basic Variants | 7.8 | NT | 7.7 | 7.8 | NT | 6.5 |
| ELISA | Relative Potency (%) | 104 | NT | 69 | 104 | NT | 92 |

TABLE 18

Compatibility of Retifanlimab in Dextrose in PVC + DEHP Bag and PUR Infusion Set at 10 mg/mL Concentration*

| Test | Results Reported | 6 Hours at RT | | | 24 Hours at 2-8° C. | | |
|---|---|---|---|---|---|---|---|
| | | $T_0$ | Pre Infusion | Post Infusion | $T_0$ | Pre Infusion | Post Infusion |
| Concentration | mg/mL | 10.3 | 10.2 | 10.2 | 10.3 | 10.4 | 10.3 |
| | % $T_0$ Conc. | NA | 99 | 99 | NA | 101 | 100 |
| pH | pH | 5.1 | 5.1 | 5.1 | 5.1 | 5.1 | 5.1 |
| Appearance | Clarity | C | C | C | C | C | C |
| | Color | L | L | L | L | L | L |
| | Particulates | FP | FP | FP | FP | FP | FP |
| Sub-visible Particle Count (per mL) | ≥2 μm | 410 | 201 | 94 | 428 | 262 | 97 |
| | ≥10 μm | 5 | 6 | 1 | 16 | 2 | 2 |
| | ≥25 μm | 0 | 0 | 0 | 1 | 0 | 0 |
| SE-HPLC | % Monomer | 98.4 | 98.4 | 98.4 | 98.4 | 98.4 | 98.4 |
| | % HMWS | 1.5 | 1.5 | 1.5 | 1.5 | 1.5 | 1.5 |
| | % LMWS | 0.1 | 0.1 | 0.1 | 0.1 | 0.1 | 0.1 |
| CIEF | % Main Charge Peak | NT | NT | 73.1 | NT | NT | 72.9 |
| | % Acidic Variants | NT | NT | 18.1 | NT | NT | 18.4 |
| | % Basic Variants | NT | NT | 8.8 | NT | NT | 8.7 |
| ELISA | Relative Potency (%) | NT | NT | 93 | NT | NT | 99 |

*Abbreviations used in Tables 17-18:
T = time;
NA = not applicable;
NT = not tested;
HMWS = high molecular weight species;
LMWS = low molecular weight species;
FP = free of particles;
FNP = essentially free from visible particles;
FPP = essentially free of proteinaceous particles;
C = clear;
L = colorless.

* Abbreviations used in Tables 17-18: T=time; NA=not applicable; NT=not tested; HMWS=high molecular weight species; LMWS=low molecular weight species; FP=free of particles; FNP=essentially free from visible particles; FPP=essentially free of proteinaceous particles; C=clear; L=colorless.

2.4. Evaluation of In-Use Compatibility of Retifanlimab DP Composition with Different Types Filter Membranes and Pore Sizes In early in-use compatibility studies of the exemplary retifanlimab DP composition, some visible and subvisible particulates were observed with normal saline only by visual inspection after incubation at two storage conditions: for 6 hours at 25° C. and 24 hours at 2-8° C. Characterization of the visible particulates by Raman microspectroscopy confirmed the proteinaceous nature of the particles. The IV infusion set with 0.2 μm low protein binding in-line filter was able to eliminate visible particulates and reduce subvisible particulates in the post-infusion samples. A more comprehensive study was performed to evaluate the compatibility and capability of filters of different membrane materials (Polyvinylidene Fluoride (PVDF), Polyethersulfone (PES) and Cellulose Acetate (CA) and sizes (0.2 μm, 5 μm and 15 μm)) to remove proteinaceous subvisible and visible particles.

2.4.1. Study Design

Retifanlimab doses at three concentrations (1.4 mg/mL, 4.5 mg/mL, and 10 mg/mL) diluted with normal saline were prepared from the exemplary retifanlimab DP composition. Since visible particle formation was more observed with normal saline as admixture compared to D5W, only normal saline was used for IV solution preparations. After completion of dose preparations, IV bags were stored at 2-8° C. overnight followed by a 4-hour equilibration period at room temperature the following day, representing the "worst-case scenario" for generation of particles. The samples were taken at the time of dose preparation (T=0), at T=24 hours at 2-8° C. followed by a 4 hour equilibration period at room temperature (post-hold), and from the final dispensed pool after simulated infusion ("post-infusion") and tested.

2.4.2. Results

All add-on filters of all sizes were able to reduce subvisible particles. Overall, there is no product quality impact on post-infusion samples when in-line or add-on filters are used after 6-hour storage at room temperature and 24-hour storage at 2-8° C. with all materials tested. Representative results of the in-use compatibility studies with 0.2 μm Polyvinylidene Fluoride (PVDF) and Cellulose Acetate (CA) filters, for low-dose (1.4 mg/mL; Table 19) and high-dose (10 mg/mL; Table 20) retifanlimab in normal saline are shown below.

TABLE 19

Test Results for 0.2 μm Polyvinylidene Fluoride (PVDF) and Cellulose Acetate (CA) Filters at 1.4 mg/mL Retifanlimab Concentration in Normal Saline*

| Quality Attribute | Attribute/Unit | 0.2 μm Polyvinylidene Fluoride (PVDF) Filter | | | 0.2 μm Cellulose Acetate (CA) Filter | | |
|---|---|---|---|---|---|---|---|
| | | T = 0 | Post Hold | Post Infusion | T = 0 | Post Hold | Post Infusion |
| Appearance | Clarity | C | C | C | C | C | C |
| | Color | L | L | L | L | L | L |
| | Particulates | FNP, FPP | FNP, FPP | FNP, FPP | FNP, FPP | FNP, FPP | FNP, FPP |
| Concentration | mg/mL | 1.37 | 1.38 | 1.39 | 1.40 | 1.40 | 1.39 |
| | % initial | NA | 100.7 | 101.5 | NA | 100 | 99.3 |
| pH | pH | 5.4 | 5.1 | 5.2 | 5.1 | 5.1 | 5.1 |
| SE-HPLC | % Monomer | 98.7 | 98.7 | 98.7 | 98.7 | 98.7 | 98.7 |
| | % Total HMWS | 1.3 | 1.3 | 1.3 | 1.3 | 1.3 | 1.3 |
| | % Total LMWS | 0.1 | 0.1 | 0.1 | 0.1 | 0.1 | 0.1 |
| Subvisible Particulates (per mL) | ≥2 μm | 396 | 468 | 6 | 314 | 488 | 14 |
| | ≥10 μm | 11 | 34 | 1 | 14 | 36 | 4 |
| | ≥25 μm | 0 | 4 | 0 | 2 | 3 | 0 |
| cIEF | % Main Charge Peak | 74.8 | NT | 75.1 | 74.8 | NT | 75.7 |
| | % Acidic Variants | 17.5 | NT | 16.3 | 17.5 | NT | 15.9 |
| | % Basic Variants | 7.8 | NT | 8.6 | 7.8 | NT | 8.4 |
| ELISA Binding | Relative Potency (%) | 104 | NT | 93 | 104 | NT | 105 |

TABLE 20

Test Results for 0.2 μm Polyvinylidene Fluoride (PVDF) and Cellulose Acetate (CA) Filters at 10 mg/mL Retifanlimab Concentration in Normal Saline*

| Quality Attribute | Attribute/Unit | 0.2 μm Polyvinylidene Fluoride (PVDF) Filter | | | 0.2 μm Cellulose Acetate (CA) Filter | | |
|---|---|---|---|---|---|---|---|
| | | T = 0 | Post Hold | Post Infusion | T = 0 | Post Hold | Post Infusion |
| Appearance | Clarity | C | C | C | C | C | C |
| | Color | L | L | L | L | L | L |
| | Particulates | FNP, FPP | FNP, FPP | FNP, FPP | FNP, FPP | FNP, FPP | FNP, FPP |
| Concentration | mg/mL | 10.17 | 10.15 | 10.17 | 10.26 | 10.20 | 10.16 |
| | % initial | NA | 99.8 | 100 | NA | 99.4 | 99.0 |
| pH | pH | 5.1 | 5.2 | 5.2 | 5.1 | 5.1 | 5.1 |
| SE-HPLC | % Monomer | 98.4 | 98.3 | 98.3 | 98.3 | 98.3 | 98.3 |
| | % Total HMWS | 1.6 | 1.4 | 1.5 | 1.4 | 1.4 | 1.5 |
| | % Total LMWS | 0.1 | 0.3 | 0.2 | 0.2 | 0.3 | 0.3 |
| Subvisible Particulates | ≥2 μm | 1,196 | 1,641 | 711 | 487 | 1,452 | 189 |
| | ≥10 μm | 66 | 15 | 30 | 10 | 35 | 20 |

TABLE 20-continued

Test Results for 0.2 µm Polyvinylidene Fluoride (PVDF) and
Cellulose Acetate (CA) Filters at 10 mg/mL Retifanlimab Concentration in Normal Saline*

| Quality Attribute | Attribute/Unit | 0.2 µm Polyvinylidene Fluoride (PVDF) Filter | | | 0.2 µm Cellulose Acetate (CA) Filter | | |
|---|---|---|---|---|---|---|---|
| | | T = 0 | Post Hold | Post Infusion | T = 0 | Post Hold | Post Infusion |
| (per mL) | ≥25 µm | 0 | 0 | 1 | 0 | 2 | 1 |
| CIEF | % Main Charge Peak | 73.4 | NT | 74.1 | 73.4 | NT | 74.1 |
| | % Acidic Variants | 17.6 | NT | 16.5 | 17.6 | NT | 16.7 |
| | % Basic Variants | 9.0 | NT | 9.4 | 9.0 | NT | 9.2 |
| ELISA Binding | Relative Potency (%) | 111 | NT | 91 | 111 | NT | 98 |

*Abbreviations used in Tables 19-20:
T = time;
NA = not applicable;
NT = not tested;
HMWS = high molecular weight species;
LMWS = low molecular weight species;
FP = free of particles;
FNP = essentially free from visible particles;
FPP = essentially free of proteinaceous particles;
C = clear;
L = colorless.

* Abbreviations used in Tables 19-20: T=time; NA=not applicable; NT=not tested; HMWS=high molecular weight species; LMWS=low molecular weight species; FP=free of particles; FNP=essentially free from visible particles; FPP=essentially free of proteinaceous particles; C=clear; L=colorless.

2.5. Temperature Cycling and Shaking Study of IV Administration Bag Preparation

The Temperature Cycling and Shaking study of the IV administration solution assessed the short-term stability of exemplary retifanlimab dosing solution preparations to simulate transport of the prepared IV bags from the clinical pharmacy to a satellite site for administration. Two concentration levels, 1.4 mg/mL (low dose) and 10 mg/mL (high dose), were evaluated to bracket the concentration range of retifanlimab after being diluted in IV bags. Normal saline was selected as the diluent for the study. Both high and low concentrations of retifanlimab IV preparations were prepared in diluent and held at room temperature for 6 hours, then held at 2-8° C. overnight, then held at room temperature for an additional 6 hours, representing potential "worst-case" hold time scenario of in-use compatibility. Following this temperature cycling, the samples were shaken to simulate potential shaking that could occur during the transport of the IV bags to the administration site.

2.5.1. Study Design

IV administration solution concentrations were prepared by using an exemplary 375 mg retifanlimab DP composition in a 250 mL saline IV bag (low dose) and an exemplary 1,000 mg retifanlimab DP composition in a 100 mL saline IV bag (high dose). The range covers the effective retifanlimab dose of 500 mg Q4W. IV bags were prepared by removing either 15 mL (for a low concentration of 1.4 mg/mL) or 50 mL (for a high concentration of 10 mg/mL) of normal saline from the bag prior to addition of the retifanlimab DP composition. Detailed dose preparation and final retifanlimab concentrations in IV bags are described below in Table 21.

TABLE 21

Retifanlimab Dose Preparation in IV Bags for Temperature Cycling and Shaking Study

| Dose (mg) | Listed IV Bag Volume (mL) | Nominal IV Bag Fill Volume (mL) | Volume Diluent Removed (mL) | Volume DP Added to IV Bag (mL) | Final Dosing Solution Concentration (mg/mL) | Administration Rate (infusion time) |
|---|---|---|---|---|---|---|
| 375 | 250 | 270 ± 10 | 15.0 | 15.0 | 1.4 ± 0.1 | 10.8 min/mL (23 min) |
| 1,000 | 100 | 110 ± 5 | 50.0 | 40.0 (2 DP Vials Required) | 10.0 ±0.5 | 4.0 min/mL (25 min) |

Upon completion of dose preparation, a 15 mL sample was collected from the bags (T=0) in a 30 mL polyethylene terephthalate glycol-modified ("PETG") bottle. After sample collection, the bags were stored at room temperature for 6 hours followed by an overnight hold at 2-8° C., which was followed by a second 6-hour equilibration period at room temperature.

After temperature cycling, a second 15 mL sample was collected from the bags prior to placing the bags on an orbital shaker programmed to shake at 100 RPM for 60 minutes. This orbital shaking was applied to simulate transport of the prepared IV bag from the clinical pharmacy to a satellite site for administration.

Upon completion of shaking, samples were taken directly from the bag for analytical testing. This was followed by sampling after infusion through an administration set containing a 0.2 µm in-line filter. The study design is described in Table 22. Table 23 lists analytical test methods performed at different stages of the study.

TABLE 22

Overview of Study Design

Diluent: Normal Saline

| IV Bag Material | Retifanlimab Concentration in IV Bag Preparation | Sampling Points |
|---|---|---|
| Polyolefin (Polypropylene and Polyethylene Copoloymer) | 1.4 mg/mL (375 mg in a 250 mL IV bag) 10 mg/mL (1000 mg in a 100 mL IV bag) | Immediately after preparation (T = 0) Post Temperature Cycle (RT for 6 Hours → 2-8° C. Overnight → RT for 6 Hours) Post Shaking (60 min @ 100 RPM) Post infusion through IV line containing 0.2 µm in-line filter |

TABLE 23

Analytical Tests Performed for Temperature Cycling and Shaking Study

| Test | T = 0 | Post Temperature Cycling | Post Shaking | Post In-line Filter Infusion (If Required) |
|---|---|---|---|---|
| Concentration (A280) | X | X | X | X |
| pH | X | X | X | Not Tested |
| Appearance | X | X | X | X |
| Subvisible Particles (HIAC) | X | X | X | X |
| SE-HPLC | X | X | X | Not Tested |
| Potency (ELISA) | X | Not Tested | X | Not Tested |
| cIEF | X | Not Tested | X | Not Tested |

2.5.2. Results

The IV Bag Temperature Cycling and Shaking Study results are shown in Table 24. In summary, solution pH and concentration did not change after temperature cycling and shaking for both doses, as expected. The concentration of post-infusion samples remained unchanged and consistent for both doses. The visual appearance results confirmed the presence of visible particles in the post-shaking samples. These observations were confirmed by the HIAC results which showed significant increase in subvisible particles after both temperature cycling and shaking. Infusion of the IV bags through administration sets containing 0.2 µm in-line filters successfully reduced the number of subvisible particles. The Reverse Osmosis Deionized ("RODI") water blank showed significant number of ≥2 µm particles in HIAC, therefore the reported sample results are adjusted to subtract the RODI blank counts. The SE-HPLC results showed no change in the monomer peak and % HMW species percentage for both doses. The cIEF results showed similar charge profiles among samples for both doses and remained within acceptance criteria. In addition, the potency results for the T=0 and post-shaking samples were consistent and remained within acceptance criteria for both doses.

TABLE 24

IV Bag Temperature Cycling and Shaking Study Test Results for High Dose and Low Dose*

| Test | Attribute/ Units | Low Dose (1.4 mg/mL) | | | | High Dose (10 mg/mL) | | | |
|---|---|---|---|---|---|---|---|---|---|
| | | Time T = 0 | PTC | PS | PI | Time T = 0 | PTC | PS | PI |
| Visual Appearance | Clarity | C | C | SO | SO | SO | SO | SO | SO |
| | Color | L | L | L | L | L | L | L | L |
| | Particles | MP | MP | CP | FP | MP | MP | CP | FP |
| Conc. (A280) | mg/mL | 1.4 | 1.4 | 1.4 | 1.4 | 9.8 | 9.8 | 9.7 | 9.6 |
| pH | pH | 5.2 | 5.2 | 5.1 | NT | 5.2 | 5.1 | 5.2 | NT |
| SE-HPLC | % Monomer | 98.6 | 98.6 | 98.3 | NT | 98.4 | 98.4 | 97.4 | NT |
| | % Total HMWS | 1.3 | 1.3 | 1.6 | | 1.6 | 1.6 | 2.5 | |
| | % Total LMWS | 0.1 | 0.1 | 0.1 | | 0.1 | 0.1 | 0.1 | |
| Subvisible Particles (HIAC)[a] | ≥2 µm | 1,547 | 16,336 | 14,436 | 10,088 | 10,858 | 9,501 | 6,092 | 6,016 |
| | ≥10 µm | 1 | 347 | 516 | 0 | 534 | 322 | 2,997 | 0 |
| | ≥25 µm | 3 | 46 | 315 | 1 | 41 | 17 | 2,452 | 0 |
| cIEF | % Main Charge Peak | 75.2 | NT | 75.1 | NT | 73.3 | NT | 73.7 | NT |
| | % Acidic Variants | 16.9 | | 16.8 | | 17.5 | | 17.3 | |
| | % Basic Variants | 7.9 | | 8.1 | | 9.2 | | 9.1 | |

TABLE 24-continued

IV Bag Temperature Cycling and Shaking Study Test Results for High Dose and Low Dose*

| Test | Attribute/ Units | Low Dose (1.4 mg/mL) | | | | High Dose (10 mg/mL) | | | |
|---|---|---|---|---|---|---|---|---|---|
| | | Time T = 0 | PTC | PS | PI | Time T = 0 | PTC | PS | PI |
| Potency (ELISA) | Relative Potency (%) | 82 | NT | 84 | NT | 85 | NT | 92 | NT |

<sup>a</sup>RODI water blank showed significant number of ≥2 μm particles in HIAC. Results tabulated here are measured particle counts, from which the RODI blank counts were subtracted. RODI blank counts: ≥2 μm = 3,183; ≥5 μm = 45; ≥10 μm = 13; ≥25 μm = 0.

*Abbreviations used in Table 24:
Conc. = concentration;
PTC = Dost temperature cycling;
PS = post shaking;
PI = post infusion;
C = clear;
SO = slightly opalescent;
L = colorless;
MP = May contain visible particles;
CP = contains particles;
FP = free of particles;
NT = not tested.

2.6. Microbial Challenge Test

A microbial challenge test was performed to ensure patient safety in case of an accidental contamination upon clinical in-use handling during preparation of the diluted exemplary retifanlimab solution. In this study, the exemplary retifanlimab DP composition was diluted in normal saline or D5W at two concentration levels, 1.4 mg/mL and 10 mg/mL, to bracket the concentration range of retifanlimab after being diluted in IV bags. The microbial challenge test was performed in duplicates by inoculating approximately 10-100 CFU/mL of the following five microorganisms plus a typical skin contaminant into the diluted retifanlimab preparation (Table 25).

TABLE 25

Microorganisms Used for Microbial Challenge Test

| Tested Microorganisms | Types |
|---|---|
| Staphylococcus aureus | Gram-positive bacteria |
| Pseudomonas aeruginosa | Gram-negative bacteria |
| Escherichia coli | Gram-negative bacteria |
| Candida albicans | Yeast |
| Aspergillus brasiliensis | Mould |
| Staphylococcus epidermidis | Gram-positive bacteria |

The suitability of the microbial count method (membrane filtration method) in combination with retifanlimab and the microorganisms was demonstrated before performing the microbial challenge test. Absence of microbial growth was defined as not more than 0.5 $\log_{10}$ CFU/mL increase compared to the T0 value.

The microbial growth was evaluated under two different storage conditions, each with a distinct set of diluted retifanlimab preparations. The first condition was to store the IV bags containing diluted retifanlimab at 2-8° C. for 48 hours immediately followed by room temperature (20-25° C.) for 12 hours, resulting in a total storage time of 60 hours. The other condition was to store the prepared IV bags at room temperature (20-25° C.) for 16 hours. At each time point, the diluted retifanlimab preparations were evaluated for their bacteriostatic/fungistatic properties and relative resistance to microbial proliferation. For the samples stored at 2-8° C. followed by room temperature incubation, the test results for the retifanlimab solution diluted in normal saline at 1.4 mg/mL (Table 26 and Table 27) and 10 mg/mL (Table 28 and Table 29) are shown below. For the retifanlimab DP composition diluted in D5W, the test results are summarized in Table 30 and Table 31 (1.4 mg/mL) and Table 32 and Table 33 (10 mg/mL).

TABLE 26

Microbial Challenge Test Results of Diluted Retifanlimab Drug Product (1.4 mg/mL) in 0.9% Normal Saline (2-8° C.)*

Microbial Count (CFU/mL) and log10 Unit Change Compared to T = 0
2-8° C.

| Test Microorganism | T0 | | 12 h | | 24 h | | 36 h | | 48 h | |
|---|---|---|---|---|---|---|---|---|---|---|
| | CFU/mL | $\log_{10}$ | CFU/mL | $\log_{10}$ | CFU/mL | $\log_{10}$ | CFU/mL | $\log_{10}$ | CFU/mL | $\log_{10}$ |
| S. aureus | 82 | NA | 76 | 0 | 61 | −0.1 | 51 | −0.2 | 49 | −0.2 |
| P. aeruginosa | 55 | NA | 51 | 0 | 49 | 0 | 41 | −0.1 | 41 | −0.1 |
| E. coli | 45 | NA | 41 | −0.1 | 29 | −0.2 | 25 | −0.3 | 29 | −0.2 |
| C. albicans | 41 | NA | 39 | 0 | 36 | 0 | 35 | −0.1 | 37 | −0.2 |
| A. brasiliensis | 17 | NA | 15 | 0 | 10 | −0.2 | 11 | −0.2 | 11 | −0.2 |
| S. epidermidis | 53 | NA | 42 | −0.1 | 27 | −0.3 | 19 | −0.4 | 16 | −0.5 |

TABLE 27

Microbial Challenge Test Results of Diluted Retifanlimab Drug Product (1.4 mg/mL) in 0.9% Normal Saline (20-25° C.)*

| | Microbial Count (CFU/mL) and log10 Unit Change Compared to T = 0 20-25° C. | | | | | |
|---|---|---|---|---|---|---|
| Test | 52 h | | 56 h | | 60 h | |
| Microorganism | CFU/mL | log$_{10}$ | CFU/mL | log$_{10}$ | CFU/mL | log$_{10}$ |
| S. aureus | 51 | −0.2 | 49 | −0.2 | 43 | −0.3 |
| P. aeruginosa | 41 | −0.1 | 22 | −0.4 | 23 | −0.3 |
| E. coli | 27 | −0.3 | 16 | −0.5 | 17 | −0.5 |
| C. albicans | 26 | −0.2 | 21 | −0.3 | 11 | −0.6 |
| A. brasiliensis | 10 | −0.2 | 10 | −0.2 | 10 | −0.2 |
| S. epidermidis | 13 | −0.6 | 0 | −1.7 | 0 | −1.7 |

TABLE 28

Microbial Challenge Test Results of Diluted Retifanlimab Drug Product (10 mg/mL) in 0.9% Normal Saline (2-8° C.)*

| | Microbial Count (CFU/mL) and log10 Unit Change Compared to T = 0 2-8° C. | | | | | | | | | |
|---|---|---|---|---|---|---|---|---|---|---|
| | T0 | | 12 h | | 24 h | | 36 h | | 48 h | |
| Test microorganism | CFU/mL | log$_{10}$ | CFU/mL | log$_{10}$ | CFU/mL | log$_{10}$ | CFU/mL | log$_{10}$ | CFU/mL | log$_{10}$ |
| S. aureus | 86 | NA | 77 | 0 | 79 | 0 | 71 | 0 | 71 | 0 |
| P. aeruginosa | 57 | NA | 49 | −0.1 | 47 | −0.1 | 46 | −0.1 | 44 | −0.2 |
| E. coli | 49 | NA | 41 | −0.1 | 39 | −0.1 | 25 | −0.3 | 25 | −0.3 |
| C. albicans | 49 | NA | 48 | 0 | 47 | 0 | 46 | 0 | 35 | −0.2 |
| A. brasiliensis | 19 | NA | 16 | −0.1 | 14 | −0.2 | 14 | −0.2 | 14 | −0.2 |
| S. epidermidis | 55 | NA | 51 | 0 | 40 | −0.1 | 37 | −0.1 | 32 | −0.2 |

TABLE 29

Microbial Challenge Test Results of Diluted Retifanlimab Drug Product (10 mg/mL) in 0.9% Normal Saline (20-25° C.)*

| | Microbial Count (CFU/mL) and log10 Unit Change Compared to T = 0 20-25° C. | | | | | | | |
|---|---|---|---|---|---|---|---|---|
| | 48 h | | 52 h | | 56 h | | 60 h | |
| Test microorganism | CFU/mL | log$_{10}$ | CFU/mL | log$_{10}$ | CFU/mL | log$_{10}$ | CFU/mL | log$_{10}$ |
| S. aureus | 71 | 0 | 68 | −0.1 | 64 | −0.1 | 61 | −0.1 |
| P. aeruginosa | 44 | −0.2 | 41 | −0.2 | 38 | −0.2 | 40 | −0.2 |
| E. coli | 25 | −0.3 | 21 | −0.4 | 21 | −0.4 | 17 | −0.5 |
| C. albicans | 35 | −0.2 | 32 | −0.2 | 23 | −0.3 | 14 | −0.6 |
| A. brasiliensis | 14 | −0.2 | 11 | −0.3 | 10 | −0.3 | 10 | −0.3 |
| S. epidermidis | 32 | −0.2 | 25 | −0.3 | 10 | −0.7 | 9 | −0.7 |

TABLE 30

Microbial Challenge Test Results of Diluted Retifanlimab Drug Product (1.4 mg/mL) in D5W (2-8° C.)*

| | Microbial Count (CFU/mL) and log10 Unit Change Compared to T = 0 2-8° C. | | | | | | | | | |
|---|---|---|---|---|---|---|---|---|---|---|
| | T0 | | 12 h | | 24 h | | 36 h | | 48 h | |
| Test Microorganism | CFU/mL | log$_{10}$ | CFU/mL | log$_{10}$ | CFU/mL | log$_{10}$ | CFU/mL | log$_{10}$ | CFU/mL | log$_{10}$ |
| S. aureus | 83 | NA | 52 | −0.2 | 16 | −0.7 | 5 | −1.2 | 2 | −0.5 |
| P. aeruginosa | 57 | NA | 41 | −0.2 | 23 | −0.4 | 10 | −0.8 | 7 | −1.0 |

TABLE 30-continued

Microbial Challenge Test Results of Diluted Retifanlimab Drug Product (1.4 mg/mL) in D5W (2-8° C.)*

| Test Microorganism | Microbial Count (CFU/mL) and log10 Unit Change Compared to T = 0 2-8° C. | | | | | | | | |
|---|---|---|---|---|---|---|---|---|---|
| | T0 | | 12 h | | 24 h | | 36 h | | 48 h | |
| | CFU/mL | $\log_{10}$ | CFU/mL | $\log_{10}$ | CFU/mL | $\log_{10}$ | CFU/mL | $\log_{10}$ | CFU/mL | $\log_{10}$ |
| E. coli | 44 | NA | 26 | −0.3 | 16 | −0.5 | 17 | −1.5 | 9 | −0.7 |
| C. albicans | 43 | NA | 38 | 0.0 | 32 | −0.1 | 17 | −0.4 | 15 | −0.4 |
| A. brasiliensis | 15 | NA | 11 | −0.2 | 10 | −0.2 | 10 | −0.2 | 11 | −0.2 |
| S. epidermidis | 57 | NA | 48 | −0.1 | 2 | −1.5 | 0 | −1.8 | 0 | −1.8 |

TABLE 31

Microbial Challenge Test Results of Diluted Retifanlimab Drug Product (1.4 mg/mL) in D5W (20-25° C.)*

| Test Microorganism | Microbial Count (CFU/mL) and log10 Unit Change Compared to T = 0 20-25° C. | | | | | |
|---|---|---|---|---|---|---|
| | 52 h | | 56 h | | 60 h | |
| | CFU/mL | $\log_{10}$ | CFU/mL | $\log_{10}$ | CFU/mL | $\log_{10}$ |
| S. aureus | 0 | −1.9 | 0 | −1.9 | 0 | −1.9 |
| P. aeruginosa | 3 | −1.3 | 0 | −1.8 | 1 | −1.8 |
| E. coli | 2 | −1.4 | 1 | −1.7 | 2 | −1.4 |
| C. albicans | 13 | −0.5 | 14 | −1.5 | 9 | −0.6 |
| A. brasiliensis | 10 | −0.2 | 10 | −0.2 | 10 | −0.2 |
| S. epidermidis | 0 | −1.8 | 0 | −1.8 | 0 | −1.8 |

TABLE 32

Microbial Challenge Test Results of Diluted Retifanlimab Drug Product (10 mg/mL) in D5W (2-8° C.)*

| Test Microorganism | Microbial Count (CFU/mL) and log10 Unit Change Compared to T = 0 2-8° C. | | | | | | | | | |
|---|---|---|---|---|---|---|---|---|---|---|
| | T0 | | 12 h | | 24 h | | 36 h | | 48 h | |
| | CFU/mL | $\log_{10}$ | CFU/mL | $\log_{10}$ | CFU/mL | $\log_{10}$ | CFU/mL | $\log_{10}$ | CFU/mL | $\log_{10}$ |
| S. aureus | 92 | NA | 53 | −0.3 | 48 | −0.3 | 18 | −0.7 | 13 | −0.9 |
| P. aeruginosa | 66 | NA | 53 | −0.1 | 31 | −0.3 | 32 | −0.3 | 29 | −0.3 |
| E. coli | 57 | NA | 38 | −0.2 | 24 | −0.4 | 26 | −0.4 | 14 | −0.7 |
| C. albicans | 41 | NA | 37 | 0 | 31 | −0.1 | 29 | −0.2 | 27 | −0.2 |
| A. brasiliensis | 16 | NA | 14 | −0.1 | 13 | −0.1 | 11 | −0.2 | 11 | −0.2 |
| S. epidermidis | 56 | NA | 38 | −0.1 | 28 | −0.3 | 0 | −1.7 | 0 | −1.7 |

TABLE 33

Microbial Challenge Test Results of Diluted Retifanlimab Drug Product (10 mg/mL) in D5W (20-25° C.)*

Microbial Count (CFU/mL) and log10 Unit Change Compared to T = 0
20-25° C.

| Test Microorganism | 52 h CFU/mL | log₁₀ | 56 h CFU/mL | log₁₀ | 60 h CFU/mL | log₁₀ |
|---|---|---|---|---|---|---|
| S. aureus | 5 | −1.3 | 0 | −2.0 | 0 | −2.0 |
| P. aeruginosa | 19 | −0.5 | 7 | −1.0 | 8 | −0.9 |
| E. coli | 15 | −0.6 | 13 | −0.7 | 3 | −1.3 |
| C. albicans | 25 | −0.2 | 16 | −0.4 | 11 | −0.6 |
| A. brasiliensis | 11 | −0.2 | 10 | −0.2 | 10 | −0.2 |
| S. epidermidis | 0 | −1.7 | 0 | −1.7 | 0 | −1.7 |

For the study conducted at room temperature (20-25° C.), the test results of the retifanlimab solution diluted in normal saline are summarized in Table 34 (1.4 mg/mL) and Table 35 (10 mg/mL). For the retifanlimab solution diluted in D5W, the test results are summarized in Table 36 (1.4 mg/mL) and Table 37 (10 mg/mL).

TABLE 34

Microbial Challenge Test Results of Diluted Retifanlimab Drug Product (1.4 mg/mL) in 0.9% Normal Saline (20-25° C.)*

Microbial Count (CFU/mL) and log10 Unit Change Compared to T = 0

| Test Microorganism | T0 CFU/mL | log₁₀ | 6 h CFU/mL | log₁₀ | 8 h CFU/mL | log₁₀ | 12 h CFU/mL | log₁₀ | 16 h CFU/mL | log₁₀ |
|---|---|---|---|---|---|---|---|---|---|---|
| S. aureus | 96 | NA | 89 | −0.1 | 91 | 0 | 90 | 0 | 91 | 0 |
| P. aeruginosa | 77 | NA | 73 | 0 | 70 | −0.1 | 66 | −0.1 | 65 | −0.1 |
| E. coli | 76 | NA | 54 | −0.2 | 61 | −0.1 | 57 | −0.1 | 56 | −0.2 |
| C. albicans | 15 | NA | 16 | 0 | 14 | −0.1 | 16 | 0 | 16 | 0 |
| A. brasiliensis | 16 | NA | 16 | 0 | 15 | 0 | 15 | 0 | 15 | 0 |
| S. epidermidis | 46 | NA | 48 | 0 | 47 | 0 | 46 | 0 | 32 | −0.2 |

TABLE 35

Microbial Challenge Test Results of Diluted Retifanlimab Drug Product (10 mg/mL) in 0.9% Normal Saline (20-25° C.)*

Microbial Count (CFU/mL) and log10 Unit Change Compared to T = 0

| Test Microorganism | T0 CFU/mL | log₁₀ | 6 h CFU/mL | log₁₀ | 8 h CFU/mL | log₁₀ | 12 h CFU/mL | log₁₀ | 16 h CFU/mL | log₁₀ |
|---|---|---|---|---|---|---|---|---|---|---|
| S. aureus | 96 | NA | 86 | −0.1 | 77 | −0.1 | 92 | 0 | 92 | 0 |
| P. aeruginosa | 75 | NA | 73 | 0 | 70 | −0.1 | 75 | 0 | 73 | 0 |
| E. coli | 67 | NA | 57 | 0 | 53 | −0.1 | 53 | −0.1 | 53 | −0.1 |
| C. albicans | 14 | NA | 17 | 0.1 | 17 | 0.1 | 14 | 0 | 14 | 0 |
| A. brasiliensis | 15 | NA | 15 | 0 | 16 | 0 | 15 | 0 | 16 | 0 |
| S. epidermidis | 45 | NA | 39 | −0.1 | 42 | −0.1 | 50 | 0 | 29 | −0.2 |

TABLE 36

Microbial Challenge Test Results of Diluted Retifanlimab Drug Product (1.4 mg/mL) in D5W (20-25° C.)*

Microbial Count (CFU/mL) and log10 Unit Change Compared to T = 0

| Test Microorganism | T0 CFU/mL | T0 $\log_{10}$ | 6 h CFU/mL | 6 h $\log_{10}$ | 8 h CFU/mL | 8 h $\log_{10}$ | 12 h CFU/mL | 12 h $\log_{10}$ | 16 h CFU/mL | 16 h $\log_{10}$ |
|---|---|---|---|---|---|---|---|---|---|---|
| S. aureus | 96 | NA | 56 | −0.3 | 18 | −0.7 | 13 | −0.9 | 4 | −1.4 |
| P. aeruginosa | 78 | NA | 74 | 0 | 71 | 0 | 69 | −0.1 | 75 | 0 |
| E. coli | 68 | NA | 48 | −0.1 | 56 | −0.1 | 52 | −0.1 | 50 | −0.1 |
| C. albicans | 19 | NA | 17 | −0.1 | 16 | −0.1 | 13 | −0.2 | 15 | −0.1 |
| A. brasiliensis | 16 | NA | 16 | 0 | 16 | 0 | 15 | 0 | 15 | 0 |
| S. epidermidis | 60 | NA | 39 | −0.2 | 28 | −0.4 | 31 | −0.3 | 36 | −0.2 |

TABLE 37

Microbial Challenge Test Results of Diluted Retifanlimab Drug Product (10 mg/mL) in D5W (20-25° C.)*

Microbial Count (CFU/mL) and log10 Unit Change Compared to T = 0

| Test Microorganism | T0 CFU/mL | T0 $\log_{10}$ | 6 h CFU/mL | 6 h $\log_{10}$ | 8 h CFU/mL | 8 h $\log_{10}$ | 12 h CFU/mL | 12 h $\log_{10}$ | 16 h CFU/mL | 16 h $\log_{10}$ |
|---|---|---|---|---|---|---|---|---|---|---|
| S. aureus | 93 | NA | 79 | −0.1 | 52 | −0.3 | 26 | −0.6 | 17 | −0.8 |
| P. aeruginosa | 77 | NA | 71 | 0 | 78 | 0 | 80 | 0 | 73 | 0 |
| E. coli | 61 | NA | 47 | −0.1 | 46 | −0.1 | 51 | −0.1 | 52 | −0.1 |
| C. albicans | 15 | NA | 15 | 0 | 14 | −0.1 | 17 | 0 | 15 | 0 |
| A. brasiliensis | 17 | NA | 15 | 0 | 15 | 0 | 15 | 0 | 15 | 0 |
| S. epidermidis | 53 | NA | 50 | 0 | 37 | −0.1 | 44 | −0.1 | 23 | −0.3 |

*Abbreviations used in Tables 26-37:
CFU = colony forming units;
NA = not applicable;
T = time.

For the retifanlimab DP composition diluted in 0.9% normal saline at both concentrations, no increase in microbial counts (i.e., not more than 0.5 log 10 CFU/mL increase compared to the T=0 value) was observed for any of the six tested organisms within the tested time duration and at both temperature conditions. For the retifanlimab DP composition diluted in D5W, none of the tested microorganisms showed any growth over time in any of the test samples at both concentration levels and both storage conditions. For some of the retifanlimab dilutions, the microbial counts of certain microorganisms showed a decrease with time. Such a phenomenon is more prominent for the samples inoculated with the two gram-positive bacteria, S. aureus and S. epidermidis. In summary, in both 0.9% normal saline and D5W, none of the combinations of diluted retifanlimab solutions exhibited any increase over time in the number of microorganisms.

2.7. Conclusions of Retifanlimab Administration Compatibility Studies

The retifanlimab pharmaceutical compositions of the disclosure were shown to be compatible with normal saline and D5W solutions in IV bags of different construction materials at concentrations of 1.4 mg/mL, 4.5 mg/mL, and 10 mg/mL, and were also compatible with all different administration sets used. The results support a retifanlimab IV solution administration time of 30 min and storage of IV bag preparation for up to 6 hours at room temperature and 24 hours at 2-8° C. Additionally, all tested in-line or add-on filters of different materials and pore sizes were compatible with retifanlimab.

The results of the Temperature Cycling and Shaking Study show that under "worst-case" storage and shaking simulation conditions at both 1.4 mg/mL and 10 mg/mL concentrations an increase in visible and sub-visible particles (≥10 and 25 μm) was observed with no other product quality impact. However, after infusion through an in-line filter no visible particles remained, and subvisible particles were significantly reduced.

The microbial challenge test was performed to ensure patient safety upon in-use handling during preparation of the retifanlimab IV infusion solution. To reflect a potential clinical storage of the IV preparation in a refrigerator and at room temperature, the retifanlimab IV preparations diluted in normal saline and 5% dextrose solutions were stored at two different conditions: 2-8° C. for 48 hours followed by an additional 12 hours storage at room temperature, and at room temperature for 12 hours. The results of the microbial challenge study also support proposed storage of retifanlimab IV bag preparations for up to 6 hours at room temperature and 24 hours at 2-8° C.

Example 3

Long-Term and Accelerated Stability Studies

Long-term and accelerated stability studies of the exemplary retifanlimab DP composition in stoppered 10 mL or 20 mL glass vials were performed. The stability was evaluated for a retifanlimab DP composition stored in the recommended condition of 2-8° C. for up to 60 months and stored in the accelerated condition of 25° C. for up to 6 months.

3.1. Experimental Plan

A summary of the tests used and the intervals generally evaluated in the 2-8° C. and 25° C. storage conditions are presented in Tables 38A and 38B, respectively. These studies were performed on 12 different lots of the exemplary retifanlimab DP composition. The majority of the studies were conducted with the vials inverted and at least one was conducted with the vials upright.

TABLE 38A

Stability Testing Time Points Stored at 2-8° C.

| Test Description | \multicolumn{10}{c}{Testing Interval (Months)} |
|---|---|---|---|---|---|---|---|---|---|---|
| | 0 | 1 | 3 | 6 | 9 | 12 | 18 | 24 | 36 | 48 | 60 |
| Protein Concentration by $A_{280}$ | X | X | X | X | X | X | X | X | X | X | X |
| Potency; PD-1 Binding ELISA | X | X | X | X | X | X | X | X | X | X | X |
| SE-HPLC | X | X | X | X | X | X | X | X | X | X | X |
| Reduced CE-LDS | X | X | X | X | X | X | X | X | X | X | X |
| Non-Reduced CE-LDS | X | X | X | X | X | X | X | X | X | X | X |
| cIEF | X | X | X | X | X | X | X | X | X | X | X |
| Appearance | X | X | X | X | X | X | X | X | X | X | X |
| pH | X | X | X | X | X | X | X | X | X | X | X |
| Osmolality | X | NS | NS | X | NS | X | NS | X | X | X | X |
| Subvisible Particulates | X | NS | NS | X | NS | X | NS | X | X | X | X |

TABLE 38B

Stability Testing at 25 ± 2° C.

| Test Description [a] | Testing Interval (Months) | | | | |
|---|---|---|---|---|---|
| | 0 | 1 | 3 | 5 | 6 |
| Protein Concentration by $A_{280}$ | X | X | X | X | X |
| Potency; PD-1 Binding ELISA | X | X | X | X | X |
| SE-HPLC | X | X | X | X | X |
| Reduced CE-LDS | X | X | X | X | X |
| Non-Reduced CE-LDS | X | X | X | X | X |
| cIEF | X | X | X | X | X |
| Appearance | X | X | X | X | X |
| pH | X | X | X | X | X |
| Osmolality | X | NS | NS | NS | X |
| Subvisible Particulates | X | NS | NS | NS | X |

Abbreviations used in Tables 38A-38B:

CE-LDS = Capillary Electrophoresis in presence of Lithium Dodecyl Sulfate;

ELISA = Enzyme Linked Immunosorbent Assay;

cIEF-Capillary Isoelectric Focusing;

SE-HPLC = Size Exclusion High Performance Liquid Chromatography;

NS = Not Scheduled (indicates analysis is not required for this time point).

3.2. Results

The results of all the tests for a representative lot stored for 60 months at 2-8° C., and for 6 months at 25° C., are presented in Tables 39A-39B, and Table 40 respectively. Additional details for assay potency, purity, and protein stability (monomers and acidic and basic variants) are provided in the summary below.

TABLE 39A

Stability Data, Retifanlimab DP Lot (2-8° C.)

| Test | | Time (Months) | | | | |
|---|---|---|---|---|---|---|
| | | 0 | 1 | 3 | 6 | 9 |
| Protein Concentration (mg/mL0 | | 25.1 | 24.8 | 25.0 | 25.0 | 25.2 |
| Potency, PD-1 Binding (%) | | 101 | 93 | 99 | 103 | 92 |
| SE-HPLC | % Monomer | 98.3 | 98.2 | 98.0 | 97.8 | 97.8 |
| | % HMW | 1.7 | 1.7 | 1.9 | 2.1 | 2.2 |
| | % LMW | 0.1 | 0.1 | 0.1 | 0.1 | 0.1 |
| Reduced CE-LDS | | 97.6 | 97.2 | 97.3 | 97.5 | 97.6 |
| Non-Reduced CE-LDS | | 97.9 | 98.3 | 97.7 | 97.5 | 98.2 |
| cIEF | % MCP | 68.3 | 68.6 | 67.3 | 71.7 | 67.8 |
| | % AV | 21.8 | 21.6 | 22.6 | 18.5 | 23.6 |
| | % BV | 9.8 | 9.8 | 10.1 | 9.8 | 8.6 |
| Appearance, Clarity | | SO | SO | SO | SO | SO |
| Appearance, Color | | PY | PY | PY | PY | PY |
| Appearance, Visible Particles | | FFP | FFP | FFP | FFP | FFP |
| pH | | 5.2 | 5.1 | 5.1 | 5.1 | 5.2 |
| Osmolality (mOsm/kg $H_2O$) | | 295 | NS | NS | 307 | NS |
| Subvisible Particulates | P ≥ 2 μm | 4,191 | NS | NS | 3,096 | NS |
| | P ≥ 10 μm | 44 | NS | NS | 32 | NS |
| | P ≥ 25 μm | 5 | NS | NS | 12 | NS |
| Sterility | | No growth | NS | NS | NS | NS |

TABLE 39B

Stability Data, Retifanlimab DP Lot (2-8° C.)

| Test | | 12 | 18 | 24 | 36 | 48 | 60 |
|---|---|---|---|---|---|---|---|
| Protein Concentration (mg/mL0 | | 25.0 | 24.4 | 24.3 | 25.3 | 25.5 | 25.1 |
| Potency, PD-1 Binding (%) | | 87 | 101 | 107 | 92 | 94 | 94 |
| SE-HPLC | % Monomer | 97.7 | 97.6 | 97.5 | 97.3 | 97.2 | 97.2 |
| | % HMW | 2.2 | 2.3 | 2.4 | 2.5 | 2.6 | 2.7 |
| | % LMW | 0.1 | 0.1 | 0.1 | NA | NA | NA |
| Reduced CE-LDS | | 97.0 | 97.6 | 95.8 | 97.0 | 97.2 | 97.3 |
| Non-Reduced CE-LDS | | 97.5 | 97.6 | 97.4 | 96.9 | 97.8 | 96.5 |
| cIEF | % MCP | 67.8 | 67.2 | 67.1 | 66.3 | 65.7 | 67.2 |
| | % AV | 23.9 | 23.7 | 24.1 | 25.8 | 25.0 | 25.9 |
| | % BV | 8.3 | 9.1 | 8.8 | 7.9 | 9.3 | 6.9 |
| Appearance, Clarity | | SO | SO | SO | SO | SO | SO |
| Appearance, Color | | PY | PY | PY | PY | CL | PY |
| Appearance, Visible Particles | | FFP | FFP | FFP | PFP | PFP | PFP |
| pH | | 5.1 | 5.1 | 5.2 | 5.2 | 5.1 | 5.1 |
| Osmolality (mOsm/kg $H_2O$) | | 303 | — | 302 | 305 | 291 | 290 |
| Su | P ≥ 2 μm | 2,737 | NS | 3,579 | 3,671 | 3,315 | 3,749 |
| | P ≥ 10 μm | 13 | NS | 20 | 37 | 77 | 35 |
| | P ≥ 25 μm | 1 | NS | 2 | 1 | 1 | 1 |
| Sterility | | No growth | NS | No growth | No growth | No growth | No growth |

TABLE 40

Stability Data, Retifanlimab DP Lot (25 ± 2° C.)

| Test | | 0 | 1 | 3 | 5 | 6 |
|---|---|---|---|---|---|---|
| Protein Concentration (mg/mL0 | | 25.1 | 24.7 | 24.9 | 25.1 | 25.0 |
| Potency, PD-1 Binding (%) | | 101 | 96 | 96 | 100 | 99 |
| SE-HPLC | % Monomer | 98.3 | 98.2 | 97.8 | 97.4 | 97.3 |
| | % HMW | 1.7 | 1.8 | 2.0 | 2.4 | 2.5 |
| | % LMW | 0.1 | 0.1 | 0.1 | 0.2 | 0.2 |
| Reduced CE-LDS | | 97.6 | 97.1 | 97.3 | 97.7 | 97.5 |
| Non-Reduced CE-LDS | | 97.9 | 98.2 | 98.1 | 96.3 | 97.3 |
| cIEF | % MCP | 68.3 | 68.1 | 63.7 | NR | 65.2 |
| | % AV | 21.8 | 22.8 | 28.0 | NR | 27.5 |
| | % BV | 9.8 | 9.1 | 8.4 | NR | 7.2 |
| Appearance, Clarity | | SO | SO | SO | SO | SO |
| Appearance, Color | | PY | PY | PY | PY | PY |
| Appearance, Visible Particles | | FFP | FFP | FFP | FFP | FFP |
| pH | | 5.2 | 5.1 | 5.2 | 5.1 | 5.1 |
| Osmolality (mOsm/kg $H_2O$) | | 295 | — | — | — | 308 |
| Subvisible Particulates | P ≥ 2 μm | 4,191 | — | — | — | 3,219 |
| | P ≥ 10 μm | 44 | — | — | — | 26 |
| | P ≥ 25 μm | 5 | — | — | — | 10 |

Abbreviations used in Tables 39A-39B and Table 40:
SE-HPLC:
Mono = monomer,
HMW = high molecular weight species,
LMW = low molecular weight species;
MCP = main charge peak,
AV = acidic variants,
BV = basic variants;
SO = slightly opalescent;
PY = pale yellow;
CL = colorless
FFP = essentially free from visible foreign particles;
PFP = practically free from visible particles;
NS = not scheduled; indicates test is not required for this time point;
NR = no result generated due to error The stability data for all DP lots investigated comply within acceptable limits through 60 months at the intended long-term storage condition of 2-8° C. Slight decreases in purity were observed by purity methods SE-HPLC, reduced CE-LDS, and non-reduced CE-LDS. Heterogeneity by cIEF also had a slight decrease in main peak and corresponding increase in acidic variants. No additional changes exceeding the variability of the analytical procedures were observed for other monitored parameters.

At the accelerated storage condition of 25±2° C., slight decreases in purity were observed by purity methods SE-HPLC (≤1%), reduced CE-LDS (≤1%), and non-reduced CE-LDS (≤2.5%). These changes in purity under accelerated conditions are not unexpected for proteins and the results were well within acceptable limits. Heterogeneity by cIEF had moderate increases in acidic variants (≤17.5% increase). The acidic variants contain mainly deamidation products. No changes exceeding the variability of the analytical procedure were observed for any of the other monitored parameters under accelerated storage conditions, demonstrating a robust stability of retifanlimab DP.

3.3. Stability Conclusions

The above analyses of quantitative data from stability-indicating methods for multiple lots supports a shelf-life of at least 24 months at the recommended storage condition of 2-8° C. for retifanlimab pharmaceutical compositions of the disclosure. The representative stability data shown in Tables 39A-39B and Table 40 indicates that all other tests, qualitative and semi- or non-quantitative, also remained within acceptable limits through at least 24 months and support a shelf-life at least about 24 months, with an upper limit of at least about 36 to at least about 60 months.

Example 4

Materials and Methods 4.1. Protein Concentration by A280

The protein concentration of retifanlimab was determined by a SoloVPE system (SoloVPE Variable Pathlength UV System from C Technologies, Inc.). The SoloVPE system employs a Slope Spectroscopy method which is based on the Beer-Lambert Law and the slope derived from the linear regression of absorbance 280 nm measurements made at multiple path lengths. The protein concentration was calculated using the following Slope Spectroscopy equation:

Protein Concentration (mg/mL)=$c=M/\alpha$ where c is the Concentration, M is the Slope of the regression line, and a is the Extinction Coefficient [1.43 (mg/mL)$^{-1}$ cm$^{-1}$] that was calculated based on the retifanlimab amino acid sequence.

4.2. Subvisible Particulates by HIAC Liquid Particle Counting

Subvisible particulate matter in the drug product was detected, sized, and counted utilizing the method described in USP<788> and Ph. Eur. 2.9.19. An electronic liquid-borne particle-counting system using a light obscuration sensor was employed. Particles were counted in three size ranges, ≥2 µm (characterization information only), ≥10 and ≥25 µm using an electronic liquid-borne particle-counting system using a light obscuration sensor (HIAC). Ten vials (10 mL/vial) of drug product are pooled for analysis.

4.3. Appearance

Appearance was assessed visually per Ph. Eur. 2.2.1 and 2.2.2 under visible light meeting minimum intensity requirements, in front of both a white and a black background. Sample aliquots were assessed in clear glass vials. Attributes examined include color of solution and clarity of solution. The degree of coloration was determined using Ph. Eur. certified color standards. The degree of clarity was determined using Ph. Eur. certified reference suspension standards.

4.1 pH Testing

The pH of a solution is was measured potentiometrically using a calibrated pH meter, following compendial methods [USP<791>, Ph. Eur. 2.2.3]. Prior to testing samples the pH meter was 3 point calibrated using certified pH standards, starting with a pH 7 buffer standard, and then proceeding to a pH 4 and then pH 10 buffer standard. Following the calibration a system suitability check was performed using two certified pH buffers at pH 5 and pH 8.

4.4. Monomeric Purity by Size Exclusion High Performance Liquid Chromatography
(SE-HPLC)

Size exclusion high performance liquid chromatography (SE-HPLC) was used as a measure of product purity and to measure impurities, particularly product aggregates. The assay includes retifanlimab Reference Standard as a control sample for identity of the monomer peak and for system suitability. Samples were injected onto a size exclusion HPLC column and are eluted isocratically with sodium phosphate/sodium sulfate buffer. Eluted proteins were detected using ultraviolet (UV) absorbance at 280 nm. The reportable result was the product purity, calculated as the area percent of the product monomer peak (compared to all peaks excluding the peaks of excipients). Also reported was the total percent of all species with apparent molecular weight greater than the monomer (called High Molecular Weight species, or HMW), the percent of dimer (which is one potential component of the HMW species), and the total percent of all species with apparent molecular weight lower than the monomer (called Low Molecular Weight species, or LMW).

4.5. Charge Heterogeneity and Identity by cIEF

The charge heterogeneity and identity of retifanlimab was evaluated by capillary isoelectric focusing (cIEF). cIEF is performed using an iCE3 System with an Alcott 720NV Autosampler (ProteinSimple). Retifanlimab Reference Standard and test article samples were prepared containing carrier ampholytes and pI markers, and were loaded into a capillary cartridge for analysis. The electrolytic tanks at each end of the capillary were filled with anolyte and catholyte solutions. Voltage was applied and the samples were focused at their pI. A camera took a UV light absorption image of the entire capillary column every 30 seconds, allowing real time monitoring of the focusing step. The resulting separation pattern image was captured and analyzed with chromatography data system software. The test article electrophoretic profile was compared to the Reference Standard electrophoretic profile. The reportable results of the assay was the average main charge peak % area, the average acidic variants % area, and the average basic variants % area, of duplicate preparations.

To confirm identity, if required, the pI of the main peak of the test article must be within 0.5 pI units of the pI of the main peak of the retifanlimab Reference Standard, and the test article profile must compare qualitatively to that of the Reference Standard, within a given sample set.

4.6. Purity by Reduced CE-LDS

Reduced lithium dodecyl sulfate-capillary electrophoresis (CE-LDS) provided quantitative information on product purity, as well as qualitative information on the nature of impurities, adducts, product fragments, and covalently linked species. Samples were denatured and reduced by heating in LDS sample buffer containing reducing agent 2-mercaptoethanol (βME). Samples were then electrophoresed using a Sciex (ABSciex, Beckman) PA800/PA800 Plus instrument. Test article and Reference Standard samples were loaded onto a capillary cartridge and product purity is determined by UV detection. Once electrophoresis was complete, data were analyzed with electrophoresis software. The reportable result for the test article was the % Purity, defined as the sum of the percent of the peaks corresponding to light chain (LC) and heavy chain (HC), recorded to the nearest 0.1%.

4.7. Purity by Non-Reduced CE-LDS

Non-reduced lithium dodecyl sulfate-capillary electrophoresis (CE-LDS) provided quantitative information on product purity, as well as qualitative information on the nature of impurities, adducts, product fragments, and covalently linked species. Samples were mixed with LDS sample buffer (without reducing agent) and heated. Samples were then electrophoresed using a Sciex (ABSciex, Beckman) PA800/PA800 Plus instrument. Test article and Reference Standard samples were loaded onto a capillary cartridge and product purity was determined by a UV detector. Once electrophoresis was complete, data were analyzed with electrophoresis software. The reportable result for the test article was the % Purity (=% Intact retifanlimab, relative to all peaks detected), recorded to the nearest 0.1%.

4.8. Potency by PD-1 Binding ELISA

An indirect enzyme-linked immunosorbent assay (ELISA) that quantitates binding activity of retifanlimab to PD-1 was used to assess the potency. Recombinant human PD-1 was coated to the solid phase (96-well assay plates). Retifanlimab sample was allowed to bind to the immobilized PD-1. A dilution series of the test article and of the retifanlimab Reference Standard was tested in this manner, in order to generate dose-response curves. Detection of retifanlimab bound to the immobilized PD-1 was accomplished with an Alkaline Phosphatase (AP) conjugated anti-human kappa antibody (aHuk-AP), which binds to the retifanlimab. Quantification of bound probe antibody aHuk-AP was achieved by addition of a colorimetric AP substrate. Oxidation of the added AP substrate by the conjugated AP yielded a colored product that was measured by spectrophotometry. The absorbance response detected is proportional to the amount of retifanlimab present. Data were fitted to a constrained four-parameter logistic model to assess the absorbance as a function of retifanlimab concentration. The reportable result, the PD-1 potency of the test article relative to the retifanlimab Reference Standard and expressed as a percentage, was calculated using the following formula:

Relative Potency=100%×EC$_{50}$ INCMGA00012 Reference Standard/EC$_{50}$ test article.

4.9. Potency and Identity by PD-1 Blockade ELISA

PD-1 receptor binding and signaling bioassay was used to assess the identity and potency of retifanlimab samples. A PD-1 blockade bioassay was used to determine the potency of retifanlimab antibody by its ability to block the PD-1 receptor (presented on Jurkat cell) from binding to the PD-L1 ligand (presented on U2OS cell). Blockade of this interaction prevents the SHP1 recruitment pathway that is initiated in the absence of PD-1 antibody and produces a chemiluminescence signal in the Jurkat engineered cells. The disruption of the PD 1/PD-L1 complex and hence SHP1 recruitment prevents the formation of active galactosidase enzyme and can directly be quantified by inhibition of a downstream chemiluminescent signal and measured with a luminescence reader. Data were fitted to a constrained four-parameter logistic model to assess the luminescence as a function of retifanlimab log concentration. The reportable result, the PD-1 potency of the test article relative to the Retifanlimab Reference Standard and expressed as a percentage, was calculated using the following formula:

Relative Potency=100%×EC50 Retifanlimab Reference Standard/EC50 test article

4.10. Microbial Challenge Testing

Retifanlimab was diluted in 0.9% normal saline or 5% dextrose in water at two concentration levels, 10 mg/mL and 1.4 mg/mL, to bracket the concentration range of retifanlimab after being diluted in IV bags. The microbial challenge test was performed in duplicates by inoculating approximately 10-100 CFU/mL of five USP <51> microorganisms plus a typical skin contaminant into the diluted retifanlimab preparation.

The suitability of the microbial count method (membrane filtration method) in combination with retifanlimab DP and the microorganisms was demonstrated before performing the microbial challenge test. Absence of microbial growth was defined according to USP <51> as not more than 0.5 log 10 CFU/mL increase compared to the T0 value.

The study was conducted at recommended storage temperatures for twice the recommended storage duration. Therefore, the diluted retifanlimab preparation was first stored at 2-8° C. for 48 hours immediately followed by room temperature (20-25° C.) for 12 hours, resulting in a total storage time of 60 hours. At each time point, the diluted retifanlimab preparations were evaluated for their bacteriostatic/fungistatic properties and relative resistance to microbial proliferation.

4.11. Osmolality

Osmolality was measured with a freezing point depression osmometer using methods defined in the compendia [USP<785>, Ph. Eur. 2.2.35]. NIST-traceable standards were used for calibration at each measurement. System suitability was determined prior to measuring test articles by measuring a NIST-traceable standard.

All publications and patents mentioned in this specification are herein incorporated by reference to the same extent as if each individual publication or patent application was specifically and individually indicated to be incorporated by reference in its entirety.

The present disclosure is not to be limited in terms of the particular embodiments described in this application. Many modifications and variations may be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the disclosure and/or the appended claims. It is to be understood that this disclosure is not limited to particular methods, compounds, or compositions, which may of course vary. It is also to be understood that the terminology used herein is for the purpose of describing particular embodiments only, and is not intended to be limiting.

---

What is claimed is:

1. A pharmaceutical composition comprising:
   (a) about 10 mg/mL to about 100 mg/mL retifanlimab;
   (b) about 5 mM to about 30 mM acetate, wherein the acetate comprises acetic acid and an acetate salt;
   (c) about 50 mg/mL to about 130 mg/mL of sucrose;
   (d) about 0.02 mg/mL to about 0.6 mg/mL of polysorbate 80 ("PS80");
   (e) water; and
   wherein the composition has a pH of about 4.0 to about 6.5.

2. The pharmaceutical composition of claim 1, wherein said acetate salt comprises sodium acetate.

3. The pharmaceutical composition of claim 1, wherein said composition comprises:
   (a) about 7.5 mM to about 20 mM acetate, about 50 mg/mL to about 130 mg/ml of sucrose, about 0.05 mg/mL to about 0.6 mg/mL of PS80, and water, wherein the composition has a pH of about 4.0 to about 6.5;
   (b) about 9 mM to about 11 mM acetate, about 76 mg/mL to about 104 mg/ml of sucrose, about 0.08 mg/mL to about 0.53 mg/mL of PS80, and water, wherein the composition has a pH of about 4.5 to about 5.7; or (c) about 9 mM to about 11 mM acetate, about 80 mg/mL to about 100 mg/mL of sucrose, about 0.08 mg/mL to about 0.15 mg/mL of PS80, and water, wherein the composition has a pH of about 4.5 to about 5.7.

4. The pharmaceutical composition of claim 1, wherein said retifanlimab is present at a concentration of about 20 mg/mL to about 30 mg/mL.

5. The pharmaceutical composition of claim 1, wherein said retifanlimab is present at a concentration of about 25 mg/mL.

6. The pharmaceutical composition of claim 1, wherein said acetate comprises glacial acetic acid at a concentration of about 0.05 mg/mL to about 0.35 mg/mL and sodium acetate trihydrate at a concentration of about 0.80 mg/mL to about 2.0 mg/mL.

7. The pharmaceutical composition of claim 1, wherein said acetate comprises glacial acetic acid at a concentration of about 0.18 mg/mL and sodium acetate trihydrate at a concentration of about 0.95 mg/mL.

8. The pharmaceutical composition of claim 1, wherein said sucrose is present at a concentration of about 80 mg/mL to about 100 mg/mL.

9. The pharmaceutical composition of claim 1, wherein said sucrose is present at a concentration of about 90 mg/mL.

10. The pharmaceutical composition of claim 1, wherein said PS80 is present at a concentration of about 0.08 mg/mL to about 0.15 mg/mL.

11. The pharmaceutical composition of claim 1, wherein said PS80 is present at a concentration of about 0.1 mg/mL.

12. The pharmaceutical composition of claim 1, wherein said composition has a pH of about 4.5 to about 5.7.

13. The pharmaceutical composition of claim 1, wherein said composition has a pH of about 5.1.

14. The pharmaceutical composition of claim 1, wherein said composition comprises about 25 mg/mL of retifanlimab, about 0.18 mg/mL of glacial acetic acid, about 0.95 mg/mL of sodium acetate trihydrate, about 90 mg/mL of sucrose, about 0.1 mg/mL of PS80, and water, wherein the composition has a pH of about 4.8 to about 5.4.

15. The pharmaceutical composition of claim 1, wherein said composition has a shelf-life of at least about 18 months at about 2° C. to about 8° C.

16. The pharmaceutical composition of claim 1, wherein said composition has a shelf-life of about 24 months at about 2° C. to about 8° C.

17. The pharmaceutical composition of claim 1, wherein said composition has a shelf-life of about 36 months at about 2° C. to about 8° C.

18. The pharmaceutical composition of claim 1, wherein said composition has a shelf-life of about 48 months at about 2° C. to about 8° C.

19. The pharmaceutical composition of claim 1, wherein said composition has a shelf-life of about 60 months at about 2° C. to about 8° C.

20. The pharmaceutical composition of claim 1, wherein said composition has an osmolality of about 200 to about 400 mOsm/kg $H_2O$.

21. The pharmaceutical composition of claim 1, wherein said composition has an osmolality of about 225 to about 400 mOsm/kg $H_2O$.

22. The pharmaceutical composition of claim 1, wherein said composition has an osmolality of about 250 to about 375 mOsm/kg $H_2O$.

23. The pharmaceutical composition of claim 1, wherein said composition has an osmolality of about 260 to about 340 mOsm/kg $H_2O$.

24. The pharmaceutical composition of claim 1, wherein said composition maintains monomeric purity of said retifanlimab for about for at least about 3 months at 25° C.

25. The pharmaceutical composition of claim 1, wherein said composition maintains monomeric purity of said retifanlimab for about for at least about 18 months at 2° C. to about 8° C.

26. The pharmaceutical composition of claim 1, wherein said composition maintains the heterogeneity profile of said retifanlimab for about for at least about 3 months at 25° C.

27. The pharmaceutical composition of claim 1, wherein said composition maintains the heterogeneity profile of said retifanlimab for about for at least about 18 months at about 2° C. to about 8° C.

28. The pharmaceutical composition of claim 1, wherein said water is sterile, nonpyrogenic, distilled water.

29. The pharmaceutical composition of claim 1, wherein said composition is sterile.

30. A container comprising the pharmaceutical composition of claim 1, wherein said container comprises about 10 mL volume of said pharmaceutical composition.

31. The container of claim 30, wherein said about 10 mL volume of said pharmaceutical composition comprises:
a) about 250 mg retifanlimab;
b) about 1.8 mg glacial acetic acid
c) about 9.5 mg sodium acetate trihydrate;
d) about 900 mg sucrose;
e) about 1 mg PS80; and
f) water; and
wherein said composition has a pH of about 4.8 to about 5.4.

32. A container comprising the pharmaceutical composition of claim 1, wherein said container comprises about 15 mL volume of said pharmaceutical composition.

33. The container of claim 32, wherein said about 15 mL volume of said pharmaceutical composition comprises:
(a) about 375 mg retifanlimab;
(b) about 2.7 mg glacial acetic acid
(c) about 14.25 mg sodium acetate trihydrate;
(d) about 1350 mg sucrose;
(e) about 1.5 mg PS80; and
(f) water; and
wherein said composition has a pH of about 4.8 to about 5.4.

34. A container comprising the pharmaceutical composition of claim 1, wherein said container comprises about 20 mL volume of said pharmaceutical composition.

35. The container of claim 34, wherein said about 20 mL volume of said pharmaceutical composition comprises:
(a) about 500 mg retifanlimab;
(b) about 3.6 mg glacial acetic acid
(c) about 19 mg sodium acetate trihydrate;
(d) about 1800 mg sucrose;
(e) about 2 mg PS80; and
(f) water; and
wherein said composition has a pH of about 4.8 to about 5.4.

36. A kit comprising the pharmaceutical composition of claim 1, and optionally further comprising instructions for administration of the pharmaceutical composition to a subject in need thereof.

37. A kit comprising a container comprising a pharmaceutical composition, said composition comprising:

(a) about 21 mg/mL to about 29 mg/mL of retifanlimab, about 0.16 mg/mL to about 0.20 mg/mL of glacial acetic acid, about 0.86 mg/mL to about 1.1 mg/mL of sodium acetate trihydrate, about 76 mg/mL to about 104 mg/mL of sucrose, about 0.08 mg/mL to about 0.53 mg/mL of PS80, and water, wherein the composition has a pH of about 4.5 to about 5.7; or (b) about 22.5 mg/mL to about 27.5 mg/mL of retifanlimab, about 0.16 mg/mL to about 0.20 mg/mL of glacial acetic acid, about 0.86 mg/mL to about 1.1 mg/mL of sodium acetate trihydrate, about 76 mg/mL to about 104 mg/mL of sucrose, about 0.08 mg/mL to about 0.53 mg/mL of PS80, and water, wherein the composition has a pH of about 4.5 to about 5.7; or (c) about 250 mg retifanlimab, about 1.8 mg glacial acetic acid, about 9.5 mg sodium acetate trihydrate, about 900 mg sucrose, about 1 mg PS80, and wherein said composition has a pH of about 4.8 to about 5.4; or (d) about 375 mg retifanlimab, about 2.7 mg glacial acetic acid, about 14.25 mg sodium acetate trihydrate, about 1350 mg sucrose, about 1.5 mg PS80, and wherein said composition has a pH of about 4.8 to about 5.4; or (e) about 500 mg retifanlimab, about 3.6 mg glacial acetic acid, about 19 mg sodium acetate trihydrate, about 1800 mg sucrose, about 2 mg PS80, and wherein said composition has a pH of about 4.8 to about 5.4; and optionally further comprising instructions for administration of the pharmaceutical composition to a subject in need thereof.

38. The kit of claim 36, wherein said composition comprises about 25 mg/mL of retifanlimab, about 0.18 mg/mL of glacial acetic acid, about 0.95 mg/mL of sodium acetate trihydrate, about 90 mg/mL of sucrose, about 0.1 mg/mL of PS80, and water, wherein the composition has a pH of about 4.8 to about 5.4.

39. The kit of claim 36, wherein said composition comprises about 250 mg retifanlimab, about 1.8 mg glacial acetic acid, about 9.5 mg sodium acetate trihydrate, about 900 mg sucrose, about 1 mg PS80, and wherein said composition has a pH of about 4.8 to about 5.4.

40. The kit of claim 36, wherein said composition comprises about 375 mg retifanlimab, about 2.7 mg glacial acetic acid, about 14.25 mg sodium acetate trihydrate, about 1350 mg sucrose, about 1.5 mg PS80, and wherein said composition has a pH of about 4.8 to about 5.4.

41. The kit of claim 36, wherein said composition about 500 mg retifanlimab, about 3.6 mg glacial acetic acid, about 19 mg sodium acetate trihydrate, about 1800 mg sucrose, about 2 mg PS80, and wherein said composition has a pH of about 4.8 to about 5.4.

42. A sealed package comprising the pharmaceutical composition of claim 1, and optionally further comprising instructions for administration of the pharmaceutical composition to a subject in need thereof.

43. A method of treating cancer, wherein the cancer expresses PD-L1, comprising administering retifanlimab to a subject in need thereof using the pharmaceutical composition according to claim 1.

44. The method of claim 43, wherein said method comprises:
(a) diluting the pharmaceutical composition in a container in 0.9% sodium chloride to obtain a dosing solution;
(b) inverting the container to mix the diluted solution; and
(c) attaching the container containing the dosing solution to a device for administration to the subject.

45. The method of claim 44, wherein the container is an IV bag containing 0.9% sodium chloride.

46. The method of claim 43, wherein said method comprises:
(a) diluting the pharmaceutical composition in a container in 5% dextrose in water (D5W) to obtain a dosing solution;
(b) inverting the container to mix the diluted solution; and
(c) attaching the container containing the dosing solution to a device for administration to the subject.

47. The method of claim 46, wherein the container is an IV bag containing 5% D5W.

48. The method of claim 44, wherein said dosing solution maintains monomeric purity of said retifanlimab for about 6 hours at 25° C. or for about 24 hours at about 2° C. to about 8° C.

49. The method of claim 43, wherein said administration is by IV infusion for at least about 30 minutes.

50. The method of claim 43, wherein said administration is by IV infusion for at least about 60 minutes.

51. The method of claim 43, wherein the pharmaceutical composition is diluted to obtain a flat dose of about 375 mg.

52. The method of claim 43, wherein the pharmaceutical composition is diluted to obtain a flat dose of about 500 mg.

53. The method of claim 43, wherein administration of the pharmaceutical composition is once every 2 weeks.

54. The method of claim 43, wherein administration of the pharmaceutical composition is once every 3 weeks.

55. The method of claim 43, wherein administration of the pharmaceutical composition is once every 4 weeks.

56. The method of claim 43, wherein said cancer is selected from the group consisting of: adrenal gland cancer, AIDS-associated cancer, alveolar soft part sarcoma, anal cancer, squamous cell carcinoma of the anal canal (SCAC), bladder cancer, bone cancer, brain and spinal cord cancer, breast cancer, HER2+ breast cancer or Triple-Negative Breast Cancer (TNBC), carotid body tumor, cervical cancer, HPV-related cervical cancer, chondrosarcoma, chordoma, chromophobe renal cell carcinoma, clear cell carcinoma, colon cancer, colorectal cancer, desmoplastic small round cell tumor, ependymoma, endometrial cancer, unselected endometrial cancer, MSI-high endometrial cancer, dMMR endometrial cancer, DNA polymerase ε (POLE) exonuclease domain mutation positive endometrial cancer, Ewing's sarcoma, extraskeletal myxoid chondrosarcoma, gallbladder or bile duct cancer, cholangiocarcinoma bile duct cancer, gastric cancer, gastroesophageal junction (GEJ) cancer, gestational trophoblastic disease, germ cell tumor, glioma, glioblastoma, head and neck cancer, squamous cell carcinoma of head and neck (SCCHN), a hematological malignancy, a hepatocellular carcinoma, islet cell tumor, Kaposi's Sarcoma, kidney cancer, renal cell carcinomas (RCC), clear cell RRC, papillary RCC and chromophobe RCC, leukemia, acute myeloid leukemia, liposarcoma/malignant lipomatous tumor, liver cancer, hepatocellular carcinoma liver cancer (HCC), lymphoma, diffuse large B-cell lymphoma (DLBCL), non-Hodgkin's lymphoma (NHL), lung cancer, small cell lung cancer (SCLC), non-small cell lung cancer (NSCLC), medulloblastoma, melanoma, uveal melanoma, meningioma, mesothelioma, mesothelial pharyngeal cancer, multiple endocrine neoplasia, multiple myeloma, myelodysplastic syndrome, neuroblastoma, neuroendocrine tumors, ovarian cancer, pancreatic cancer, papillary thyroid carcinoma, parathyroid tumor, pediatric cancer, peripheral nerve sheath tumor, pharyngeal cancer, pheochromocytoma, pituitary tumor, prostate cancer, metastatic castration resistant prostate cancer (mCRPC), posterious uveal melanoma, renal metastatic cancer, rhabdoid tumor, rhabdomyosarcoma, sarcoma, skin cancer, Merkel cell carcinoma, a small round blue cell tumor of childhood, neuroblastoma, rhabdomyosarcoma, soft-tissue sarcoma, squamous cell cancer, stomach cancer, synovial sarcoma, testicular cancer, thymic carcinoma, thymoma, thyroid cancer, urothelial cancer, and uterine cancer.

57. The method of claim 56, wherein said cancer is anal cancer, breast cancer, colorectal cancer, endometrial cancer, gastric cancer, GEJ cancer, head and neck cancer, kidney cancer, liver cancer, lung cancer, lymphoma, melanoma, multiple myeloma, ovarian cancer, pancreatic cancer, prostate cancer, and skin cancer, and urothelial cancer.

58. The method of claim 56, wherein said cancer is SCAC.

59. The method of claim 56, wherein said lung cancer is NSCLC.

60. The method of claim 56, wherein said endometrial cancer, is MSI-high endometrial cancer, dMMR endometrial cancer, or POLE exonuclease domain mutation positive endometrial cancer.

61. The method of claim 56, wherein said skin cancer is melanoma, or Merkel cell carcinoma.

62. The method of claim 56, wherein said head and neck cancer is SCCHN.

63. The method of claim 56, wherein said prostate cancer is mCRPC.

64. The method of claim 56, wherein said kidney cancer is RCC or clear cell RCC.

65. The method of claim 56, wherein said cancer is urothelial cancer.

66. The method of claim 43, wherein said subject is a human subject.

\* \* \* \* \*